United States Patent
Kabadi et al.

(10) Patent No.: US 11,369,692 B2
(45) Date of Patent: Jun. 28, 2022

(54) MATERIALS AND METHODS FOR TREATMENT OF DUCHENNE MUSCULAR DYSTROPHY

(71) Applicant: Vertex Pharmaceuticals Incorporated, Boston, MA (US)

(72) Inventors: Ami Meda Kabadi, Cambridge, MA (US); Chad Albert Cowan, Cambridge, MA (US); Ante Sven Lundberg, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 645 days.

(21) Appl. No.: 15/763,328

(22) PCT Filed: Oct. 28, 2016

(86) PCT No.: PCT/IB2016/001679
§ 371 (c)(1),
(2) Date: Jun. 22, 2018

(87) PCT Pub. No.: WO2017/072590
PCT Pub. Date: May 4, 2017

(65) Prior Publication Data
US 2019/0374655 A1 Dec. 12, 2019

Related U.S. Application Data

(60) Provisional application No. 62/324,064, filed on Apr. 18, 2016, provisional application No. 62/247,484, filed on Oct. 28, 2015.

(51) Int. Cl.
*C12N 15/63* (2006.01)
*A61K 48/00* (2006.01)
*A61P 25/14* (2006.01)
*A61P 21/00* (2006.01)
*A61K 38/46* (2006.01)
*C12N 9/22* (2006.01)
*C12N 15/113* (2010.01)
*C12N 15/90* (2006.01)

(52) U.S. Cl.
CPC ........ *A61K 48/0058* (2013.01); *A61K 38/465* (2013.01); *A61P 21/00* (2018.01); *A61P 25/14* (2018.01); *C12N 9/22* (2013.01); *C12N 15/113* (2013.01); *C12N 15/907* (2013.01)

(58) Field of Classification Search
CPC ... A61K 48/0058; A61K 38/465; A61P 25/14; A61P 21/00; C12N 9/22; C12N 15/113; C12N 15/907
See application file for complete search history.

(56) References Cited

U.S. PATENT DOCUMENTS

| | | |
|---|---|---|
| 2015/0024500 A1 | 1/2015 | Yu et al. |
| 2017/0362635 A1 | 12/2017 | Chamberlain et al. |
| 2018/0320197 A1 | 11/2018 | Gersbach et al. |
| 2019/0048337 A1* | 2/2019 | Hsu ...................... C12N 15/102 |

FOREIGN PATENT DOCUMENTS

| | | | |
|---|---|---|---|
| CN | 103930550 A | 7/2014 | |
| WO | 2013170385 A1 | 11/2013 | |
| WO | WO 2014/197748 A2 | 12/2014 | |
| WO | WO-2014197748 A2 * | 12/2014 | ............... C12N 9/22 |
| WO | 2016020399 A1 | 2/2016 | |
| WO | 2016025469 A1 | 2/2016 | |
| WO | 2016115543 A2 | 7/2016 | |
| WO | 2016161380 A1 | 10/2016 | |
| WO | 2016174056 A1 | 11/2016 | |
| WO | 2017062862 A2 | 4/2017 | |
| WO | 2017095967 A2 | 6/2017 | |

OTHER PUBLICATIONS

Score report for Gersbach WO-2014197748-A2 published Dec. 2014. (Year: 2014).*
International Search Report for Application No. PCT/IB2016/001679, dated Feb. 9, 2017.
Written Opinion for Application No. PCT/IB2016/001679, dated Feb. 9, 2017.
Hongmei, Lisa Li et al., "Precise Correction of the Dystrophin Gene in Duchenne Muscular Dystrophy Patient Induced Pluripotent Stem Cells by TALEN and CRISPR-Cas9," Stem Cell Reports, vol. 4. No. 1, Jan. 1, 2015 (Jan. 1, 2015), pp. 143-154, XP055233644, United States ISSN: 2213-6711. DOI: 10.1016jj.stemcr.2014.10.013.
Ousterout, David G. et al, "Multiplex CRISPR/Cas9-based genome editing for correction of dystrophin mutations that cause Duchenne muscular dystrophy," Nature Communications, vol. 6., Feb. 18, 2015 (Feb. 18, 2015), pp. 1-13. XP055196515, DOI: 10.1038/ncomms7244.
Amoasii et al., "Single-cut genome editing restores dystrophin expression in a new mouse model of muscular dystrophy," Science Translational Medicine, 9(418): eaan8081 (11 pages), 2017.
Bengtsson et al., "Progress and prospects of gene therapy clinical trials for the muscular dystrophies," Human Molecular Genetics, 25(R1): R9-R17, 2015.
Kabadi et al., "Multiplex CRISPR/Cas9-based genome engineering from a single lentiviral vector," Nucleic Acids Research, 42(19): e147 (11 pages), 2014.
Li et al., "Precise Correction of the Dystrophin Gene in Duchenne Muscular Dystrophy Patient Induced Pluripotent Stem Cells by TALEN and CRISPR-Cas9," Stem Cell Reports, 4:143-154, 2015.
Long et al., "Prevention of muscular dystrophy in mice by CRISPR/Cas9-mediated editing of germline DNA," Science, 345(6201): 1184-1188, 2014.
Wei et al., "Prevention of Muscle Wasting by CRISPR/Cas9-mediated Disruption of Myostatin In Vivo," Molecular Therapy, 24(11):1889-1891, 2016.

* cited by examiner

*Primary Examiner* — Catherine S Hibbert
(74) *Attorney, Agent, or Firm* — McNeill Baur PLLC

(57) ABSTRACT

The present application provides materials and methods for treating a patient with Duchenne Muscular Dystrophy (DMD) both ex vivo and in vivo. In addition, the present application provides materials and methods for editing a dystrophin gene in a cell by genome editing.

3 Claims, 76 Drawing Sheets
Specification includes a Sequence Listing.

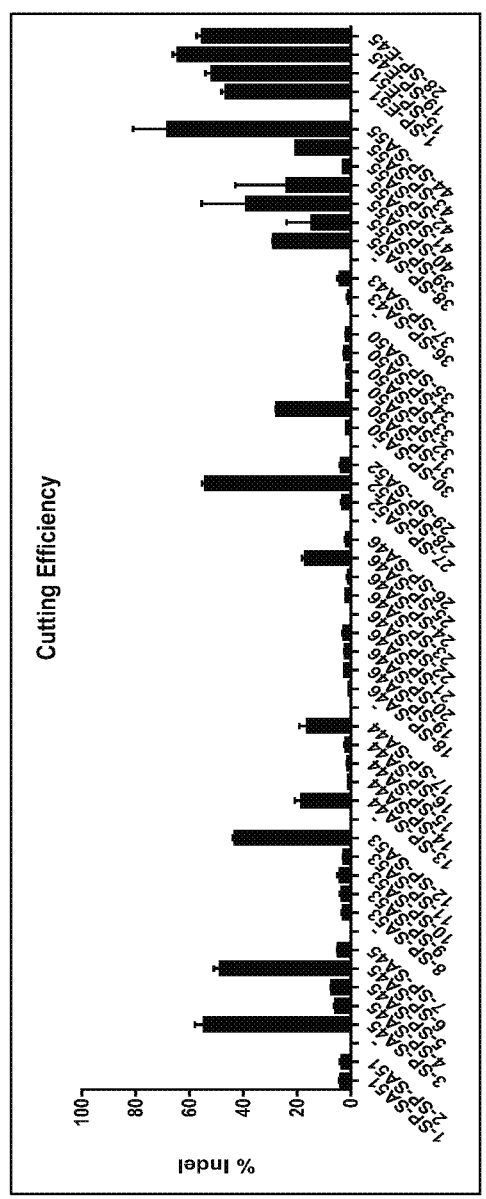

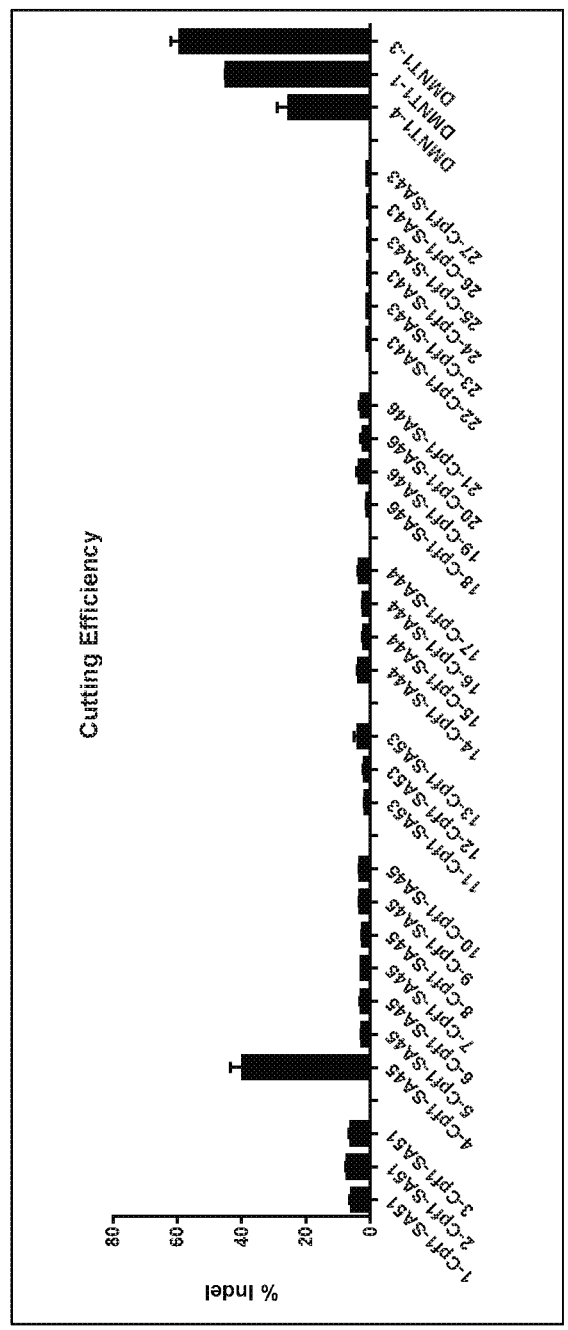

FIGURE 5A

| gRNA name | SEQ ID NO | gRNA sequence | Avg % Indel | Indel SEM | Avg % Splice Acceptor Knock Out | Splice Acceptor Knock Out SEM |
|---|---|---|---|---|---|---|
| 1-SP-SA51 | 145442 | AAAATATTTTAGCTCCTACT |  | 0.000 |  | 0.000 |
| 2-SP-SA51 | 145443 | TGCAAAAACCCAAAATATTT |  | 0.000 |  | 0.000 |
| 3-SP-SA45 | 186216 | TGGTATCTTACAGGAACTCC |  | 0.015 | 11.6 | 0.006 |
| 4-SP-SA45 | 186217 | TTGGTATCTTACAGGAACTC | 1.3 | 0.001 | 0.3 | 0.000 |
| 5-SP-SA45 | 186218 | TGCCATCTGGAGTTCCTGT | 5.6 | 0.002 | 2.5 | 0.001 |
| 6-SP-SA45 | 186219 | TTGCCTTTTTGGTATCTTAC |  | 0.011 | 12.9 | 0.004 |
| 7-SP-SA45 | 186220 | TTTGCCTTTTTGGTATCTTA | 0.5 | 0.000 |  | 0.000 |
| 8-SP-SA53 | 125451 | TGATTCTGAATTCTTTCAAC |  | 0.000 |  | 0.000 |
| 9-SP-SA53 | 125452 | TTTCCTTTTATTCTAGTTGA |  | 0.000 |  | 0.000 |
| 10-SP-SA53 | 125453 | AATTCTTTCAACTAGAATAA | 2.5 | 0.001 | 0.5 | 0.000 |
| 11-SP-SA53 | 125455 | ATTTATTTTTCCTTTTATTC |  | 0.000 |  | 0.000 |
| 12-SP-SA53 | 125454 | ATTCTTTCAACTAGAATAAA |  | 0.010 | 7.4 | 0.004 |
| 13-SP-SA44 | 237600 | AGATCTGTCAAATCGCCTGC | 26.7 | 0.017 | 16.1 | 0.011 |
| 14-SP-SA44 | 237599 | CAGATCTGTCAAATCGCCTG |  | 0.000 |  | 0.000 |
| 15-SP-SA44 | 237602 | GTCAAATCGCCTGCAGGTAA | 0.4 | 0.000 | 0.1 | 0.000 |
| 16-SP-SA44 | 237603 | GATCCATATGCTTTTACCTG |  | 0.000 |  | 0.000 |
| 17-SP-SA44 | 237601 | ATCCATATGCTTTTACCTGC | 21.6 | 0.011 | 2.5 | 0.002 |
| 18-SP-SA46 | 178873 | TTGTTCTTCTAGCCTGGAGA |  | 0.000 |  | 0.000 |
| 19-SP-SA46 | 178869 | ATTCTTTTGTTCTTCTAGCC |  | 0.000 |  | 0.000 |
| 20-SP-SA46 | 178875 | TTCTTCTAGCCTGGAGAAAG | 0.6 | 0.001 | 0.1 | 0.000 |
| 21-SP-SA46 | 178870 | TTCTTCTTTCTCCAGGCTAG |  | 0.000 |  | 0.000 |
| 22-SP-SA46 | 178871 | TCTTTTGTTCTTCTAGCCTG |  | 0.000 |  | 0.000 |
| 23-SP-SA46 | 178868 | AAGATATTCTTTTGTTCTTC |  | 0.000 |  | 0.000 |
| 24-SP-SA46 | 178872 | TTATTCTTCTTTCTCCAGGC |  | 0.000 |  | 0.000 |
| 25-SP-SA46 | 178874 | AATTTTATTCTTCTTTCTCC | 14.7 | 0.008 | 2.5 | 0.001 |
| 26-SP-SA46 | 178876 | CAATTTTATTCTTCTTTCTC |  | 0.000 |  | 0.000 |
| 27-SP-SA52 | 136213 | AATCCTGCATTGTTGCCTGT | 0.4 | 0.000 | 0.2 | 0.000 |
| 28-SP-SA52 | 136214 | TAAGGGATATTTGTTCTTAC |  | 0.008 | 15.1 | 0.005 |
| 29-SP-SA52 | 136215 | CTAAGGGATATTTGTTCTTA |  | 0.000 |  | 0.000 |
| 30-SP-SA50 | 155685 | ATGCTTTTCTGTTAAAGAGG | 0.4 | 0.000 | 0.1 | 0.000 |
| 31-SP-SA50 | 155687 | TGTATGCTTTTCTGTTAAAG | 49.0 | 0.010 |  | 0.008 |
| 32-SP-SA50 | 155686 | TCTTCTAACTTCCTCTTTAA | 0.3 | 0.000 | 0.1 | 0.000 |
| 33-SP-SA50 | 155689 | ATGTGTATGCTTTTCTGTTA |  | 0.000 |  | 0.000 |
| 34-SP-SA50 | 155684 | TTTTCTGTTAAAGAGGAAGT |  | 0.000 |  | 0.000 |
| 35-SP-SA50 | 155688 | GTGTATGCTTTTCTGTTAAA |  | 0.000 |  | 0.000 |
| 36-SP-SA43 | 252293 | TTTTATATTACAGAATATAA |  | 0.000 |  | 0.000 |
| 38-SP-SA55 | 114755 | CTGAACATTTGGTCCTTTGC | 39.2 | 0.021 | 7.0 | 0.003 |
| 39-SP-SA55 | 114751 | CATTTGGTCCTTTGCAGGGT | 2.5 | 0.021 | 1.0 | 0.000 |
| 40-SP-SA55 | 114753 | CTCGCTCACTCACCCTGCAA |  | 0.021 |  | 0.013 |

FIGURE 5B

| | | | | | | | |
|---|---|---|---|---|---|---|---|
| 41-SP-SA55 | 114756 | TCTGAACATTGGTCCTTTG | 0.6 | 0.021 | | | 0.000 |
| 42-SP-SA55 | 114758 | TGGTCCTTTGCAGGGTGAGT | 14.1 | 0.021 | 2.1 | | 0.000 |
| 43-SP-SA55 | 114762 | TCTCGCTCACTCACCCTGCA | 26.2 | 0.021 | 16.4 | | 0.003 |
| 44-SP-SA55 | 114764 | TGAACATTGGTCCTTTGCA | | 0.021 | 8.4 | | 0.001 |
| 1-SP-E51 | 1410430 | CCTACTCAGACTGTTACTC | | 0.021 | 2.0 | | 0.001 |
| 15-SP-E51 | 1410444 | CCAGAGTAACAGTCTGAGT | | 0.021 | 8.2 | | 0.003 |
| 19-SP-E45 | 1410448 | GGAACTCCAGGATGGCATT | | 0.021 | 4.4 | | 0.002 |
| 28-SP-E45 | 1410457 | CCGCTGCCCAATGCCATCC | | 0.021 | 3.7 | | 0.001 |

FIGURE 6

| gRNA name | SEQ ID NO | gRNA sequence | Avg % Indel | Indel SEM | Avg % Splice Acceptor Knock Out | Splice Acceptor Knock Out SEM |
|---|---|---|---|---|---|---|
| 1-NM-SA51 | 1410400 | AGTCTGAGTAGGAGCTAAAATATT | 0.1 | 0.000 | 0.0 | 0.000 |
| 2-NM-SA44 | 1410401 | CTTGATCCATATGCTTTTACCTGC | 0.0 | 0.000 | 0.0 | 0.000 |
| 3-NM-SA52 | 1410402 | ATATTTGTTCTTACAGGCAACAAT | 0.6 | 0.000 | 0.1 | 0.000 |
| 1-SA-SA51 | 485512 | TGAGTAGGAGCTAAAATATT | 0.8 | 0.001 | 0.1 | 0.000 |
| 2-SA-SA45 | 490807 | TTGGTATCTTACAGGAACTC | 10.8 | 0.005 | 2.9 | 0.001 |
| 3-SA-SA53 | 482860 | TGATTCTGAATTCTTTCAAC | 0.0 | 0.000 | 0.0 | 0.000 |
| 4-SA-SA53 | 482861 | TTTCCTTTTATTCTAGTTGA | 0.0 | 0.000 | 0.0 | 0.000 |
| 5-SA-SA46 | 489814 | TTCTTCTAGCCTGGAGAAAG | 26.0 | 0.013 | 4.4 | 0.002 |
| 7-SA-SA55 | 481421 | TCTGAACATTTGGTCCTTTG | 36.7 | 0.024 | 7.6 | 0.006 |
| 8-SA-SA55 | 481420 | AACATTTGGTCCTTTGCAGG | 35.4 | 0.039 | 22.4 | 0.025 |
| 1-ST-SA53 | 534494 | CTGATTCTGAATTCTTTCAA | 0.1 | 0.000 | 0.0 | 0.000 |
| 2-ST-SA53 | 534495 | TTTTCCTTTTATTCTAGTTG | 0.1 | 0.000 | 0.0 | 0.000 |
| 3-ST-SA46 | 537307 | TTCTTTTGTTCTTCTAGCCT | 0.1 | 0.000 | 0.0 | 0.000 |
| 4-ST-SA46 | 537308 | GTTCTTCTAGCCTGGAGAAA | 1.6 | 0.002 | 0.4 | 0.000 |
| 5-ST-SA50 | 536097 | ATCTTCTAACTTCCTCTTTA | 0.5 | 0.001 | 0.1 | 0.000 |
| 19-SP-E45 | 1410448 | GGAACTCCAGGATGGCATT | 35.4 | 0.040 | 2.0 | 0.003 |
| 15-SP-E51 | 1410444 | CCAGAGTAACAGTCTGAGT | 30.0 | 0.042 | 4.3 | 0.006 |

Δ52 PCR Analysis

Δ44 PCR Analysis

FIGURE 10C

|  | Δ52 cell line generation | | Δ44 cell line generation | |
|---|---|---|---|---|
|  | gRNA 1-SP-152 + 2-SP-153 | gRNA 2-SP-152 + 2-SP-153 | gRNA 2-SP-144 + 3-SP-145 | gRNA 2-SP-144 + 4-SP-145 |
| # of clones | 128 | 133 | 132 | 124 |
| # of deletions | 24 | 33 | 7 | 9 |
| Deletion Efficiency (%) | 18.8 | 24.8 | 5.3 | 7.3 |
| Overall # of clones | 261 | | 256 | |
| Overall # of deletions | 57 | | 16 | |
| Overall Deletion Efficiency (%) | 21.8 | | 6.3 | |

FIGURE 11A gRNA 1-SP-I52 + 2-SP-I53 tactcaaggcattcagacagtggtttaagtaatgtagggtgggcaggaactttggtaagaccca
++++++++++++++++++++++++++++++++++++++++++++++++++++++++++++++++
atgagttccgtaagtctgtcaccaaattcattacatcccacccgtccttgaaaccattctgggt
                        ▬▬▬▬▬▬▬▬▬▬▬▬▬
                                    Right gRNA tactcaaggcattcagacagtggtttaagtaatgtagggtgggcaggaactttggtaagaccca

TACTCAAGGCATTCAGACAGTGGTTTAAGTA▬▬▬▬▬GGTGGGCAGGAACTTTGGTAAGACCCA

TACTCAAGGCATTCAGACAGTGGT▬▬▬▬▬▬▬▬▬▬▬▬GGGCAGGAACTTTGGTAAGACCCA

FIGURE 11B gRNA 2-SP-I52 + 2-SP-I53 cagtggtttaagtaatccgagg gtagggtgggcaggaactttggtaagacccatctgactagacgctgtgcatattctttcttctga
++++++++++++++++++++++ +++++++++++++++++++++++++++++++++++++++++++++++++++++++++++++++
gtcaccaaattcattaggctcc catcccacccgtccttgaaaccattctgggtagactgatctgcgacacgtataagaaagaagact
            ▬▬  ▬▬
          Left gRNA
                Right gRNA cagtggtttaagtaatccgagg gtagggtgggcaggaactttggtaagacccatctgactagacgctgtgcatattctttcttctga CAGTGGTTTAAGTAATCCGAGG ▬AGGGTGGGCAGGAACTTTGGTAAGACCCATCTGACTAGACGCTGTGCATATTCTTTCTTCTGA

CAGTGGTTTAAGTAATCCGAGG ▬▬▬▬▬▬ACTTTGGTAAGACCCATCTGACTAGACGCTGTGCATATTCTTTCTTCTGA

CAGTGGTTTAAGTAATCCGAGG ▬▬▬▬▬AGGAACTTTGGTAAGACCCATCTGACTAGACGCTGTGCATATTCTTTCTTCTGA

CAGTGGTTTAAGTAATCCGAG▬▬TAGGGTGGGCAGGAACTTTGGTAAGACCCATCTGACTAGACGCTGTGCATATTCTTTCTTCTGA

CAGTGGTTTAAGTA▬▬▬▬▬▬▬▬▬▬▬▬▬▬▬▬▬▬▬▬▬▬▬▬▬▬▬▬▬▬▬▬▬▬▬▬▬▬▬▬TCTTTCTTCTGA

FIGURE 12A

| SEQ ID NO | gRNA Sequence | % Indel |
|---|---|---|
| 236915 | ATCGATGAAGGTATCTTACG | 70.2 |
| 236163 | AAGGTAGAAACAAGCATTCT | 29.3 |
| 236084 | ATCAATTTTTCTACGTACCG | 5.8 |
| 232401 | ACCTAGATGACACAGCGTCG | 27.5 |
| 230005 | TGTTCTGTAGATGTAGCGCC | 12.8 |
| 229558 | TACAGGAGACGTAATTGACG | 37.4 |
| 229557 | ACAGGAGACGTAATTGACGG | 54.9 |
| 229303 | ACACTCAGGCATTACTACGG | 44.8 |
| 228978 | ATGGGCTAGTTACGGCTTGA | 54.8 |
| 228448 | CCTATCACTAGTATTCGGTA | 51.1 |
| 227602 | CAGGGACGTTGTTAGACCGT | 28.9 |
| 226063 | GGGAGCTTATACAAGACCGT | 33.0 |
| 226062 | GGGGAGCTTATACAAGACCG | 22.8 |
| 225417 | ACTAGATGCTTGTCTACGGC | 16.4 |
| 225410 | AGCATCTAGTAATTGACGGT | 6.9 |
| 225047 | TCCGCCAAGCGCCTATTTAC | 37.9 |
| 224650 | ATGCTGAGGTCCGGATTAAG | 29.7 |
| 224549 | GGCGCCAAGATTCCCCTAGC | 24.0 |
| 224378 | GATTAATGAACGTGCGCACC | 13.9 |
| 224127 | TGTCCAACACTATGATCCGA | 8.5 |
| 224126 | GTCCAACACTATGATCCGAT | 41.7 |
| 223418 | GGTTTTCTCGTGACGAGCCA | 15.6 |
| 221914 | CCCCGTGTGTAGCAGCGCAA | 24.3 |
| 221143 | GACGAGTTGGCTCGGGATTA | 28.8 |
| 219974 | AATAATACGTGGACCTGCGC | 17.7 |
| 218293 | CCCGTCTTACCGGTCTTGAT | 40.6 |
| 218297 | CCGATCAAGACCGGTAAGAC | 26.9 |
| 218207 | ACGTAACCCTAGTTTCGCTC | 10.8 |
| 218173 | ACTCTAGCTTCGGACAACGT | 38.3 |
| 217734 | CACTGCTTTAGCTACGCTAT | 5.5 |
| 217322 | GATTCTGACGTGAGTACTAC | 24.3 |
| 217090 | GATTAGCATACAACCGCACT | 16.5 |
| 217082 | TAGGAGCCTAGTTATACGAA | 61.6 |
| 216165 | TCTGATGTGGACTAGTAACG | 27.0 |
| 215619 | TCTTCCCATGAACGAAATCG | 16.1 |
| 213660 | TTTAGGAATCGATTGTTTCG | 8.8 |
| 213620 | TATTCAAGTGCTAACGCGTG | 12.8 |
| 213618 | ATTCAAGTGCTAACGCGTGT | 8.4 |
| 213617 | TTCAAGTGCTAACGCGTGTG | 8.0 |

FIGURE 12B

| 213420 | AAGCTAAGTGAGGTTCGACC | 23.4 |
|---|---|---|
| 212990 | ATCATGTTTAGTTATGCCCG | |
| 211529 | TAAACCAGCGGATTACGGTG | 47.6 |
| 211528 | AAACCAGCGGATTACGGTGT | 28.8 |
| 211531 | TCACCCACACCGTAATCCGC | |
| 210516 | CGGACTAGCGGGTCAATATC | 50.6 |
| 210514 | TGATACATCGTGTTGTGCGT | |
| 208854 | ACGTGCAATTTTGGGCGCAC | |
| 208853 | CGTGCAATTTTGGGCGCACT | |
| 205628 | CAACGAGTATACAAAGATCG | 21.6 |
| 205319 | GCTAAGAAACCAATGTACGG | 48.9 |
| 203517 | GGCCCTTTAATTACGCACTG | 30.4 |
| 202709 | AAATGTAAATTCCACAACAA | 17.3 |
| 200544 | GATTATACACTAGGTTCGTC | 14.7 |
| 200019 | AACGTTAGGATCGCTGATTC | |
| 199808 | TACATTTTGGGCAGTAACGC | |
| 199078 | ACAACTGCCCTCTATACGGC | 15.3 |
| 198782 | TCTTAAAACGCGGTCCTCCT | |
| 198508 | GCTTTCCCCTACCATCGAGC | 13.4 |
| 198507 | CTTTCCCCTACCATCGAGCG | 45.2 |
| 198514 | AGAACCCCGCTCGATGGTAG | 51.7 |
| 198512 | AAGAACCCCGCTCGATGGTA | 14.3 |
| 198511 | GAAGAACCCCGCTCGATGGT | 38.1 |
| 196798 | CACTAGTAGATCACGATCAG | 31.9 |
| 196503 | ACCACCCGTGTTCTTTGCGG | 20.4 |
| 196502 | TACCACCCGTGTTCTTTGCG | 25.5 |
| 195761 | AAAAGCGTCGATCGAACTGT | |
| 195585 | ATCTACTCTAGTTGTACCGA | 18.7 |
| 195575 | TTGATTTGGTCGAGGCCCAA | 17.4 |
| 194966 | GGTTGCAGGTCCTGCCGAAC | 18.4 |
| 194292 | GCTTATACAACCACACCGTT | 62.9 |
| 193612 | GAAACAGCTTTTGGCCCGCG | 19.5 |
| 192745 | TCCTATTCTGATCACGGACG | 18.1 |
| 192221 | GCATGCCTGTTAATACGTTC | 43.1 |
| 191869 | TCAGCCTTACGTAGCGTTGC | 19.2 |
| 191741 | AAGCACCCATGAATCGGCCA | 27.4 |
| 191550 | TCAACTCACTTGCGGCCCTA | 38.1 |
| 191478 | GCGATTAATCCGGAGTGCTA | |
| 191477 | CGATTAATCCGGAGTGCTAA | |
| 191409 | TAATAACCCTACGTATCATC | 37.7 |
| 191324 | ACGCCAACTGTTAGAAGCGT | 18.4 |

FIGURE 12C

| 191323 | AACGCCAACTGTTAGAAGCG | 18.4 |
|---|---|---|
| 190635 | TAGTAGGTTAACACTCCGTG | 6.3 |
| 190493 | TCGGAGTGCCTAATTCGTGT | 3.8 |
| 189640 | ATGTATGACGCTCCCGAGTC | 4.4 |
| 189321 | AGATTCCCATTATTCGGTAC | 10.8 |
| 186914 | AGTGCATATCTAACTCCCGT | 32.0 |
| 186912 | AAGTGCATATCTAACTCCCG | 9.2 |
| 186670 | CAGGCCCCAATATACACGGA | 53.2 |
| 186673 | GTACAGCCCTCGGTGTATAT | 35.9 |
| 186301 | TTAGTGATCGTGGATACGAG | 45.0 |
| 186219 | TTGCCTTTTTGGTATCTTAC | 19.3 |
| 186220 | TTTGCCTTTTTGGTATCTTA | 5.8 |
| 186216 | TGGTATCTTACAGGAACTCC | 40.7 |
| 186217 | TTGGTATCTTACAGGAACTC | 5.3 |
| 186215 | ATCTTACAGGAACTCCAGGA | 79.0 |
| 186218 | TGCCATCCTGGAGTTCCTGT | 5.5 |
| 186212 | CAGGAACTCCAGGATGGCAT | 25.2 |
| 186209 | TCCAGGATGGCATTGGGCAG | 46.8 |
| 186213 | GCCGCTGCCCAATGCCATCC | 50.4 |
| 186206 | GTCAGAACATTGAATGCAAC | 8.3 |
| 186204 | CAGAACATTGAATGCAACTG | 59.2 |
| 186194 | AACAGATGCCAGTATTCTAC | 22.5 |
| 186189 | AATTGGGAAGCCTGAATCTG | 34.6 |
| 186186 | TGGGAAGCCTGAATCTGCGG | 56.4 |
| 186184 | AAGCCTGAATCTGCGGTGGC | 16.9 |
| 186188 | CCTCCTGCCACGCAGATTC | 37.0 |
| 186065 | CAACTGCAGCAGCACGCATT | 27.1 |
| 185720 | AAAACCTATCATCGGCTGTA | 23.5 |
| 185719 | AAACCTATCATCGGCTGTAA | 27.1 |
| 185718 | AACCTATCATCGGCTGTAAG | 54.6 |
| 185723 | TTCCCCTTACAGCCGATGAT | 51.8 |
| 185608 | AGGAGAAGACATACCAGTCG | 27.5 |
| 185607 | GGAGAAGACATACCAGTCGA | 56.9 |
| 185606 | GAGAAGACATACCAGTCGAG | 39.2 |
| 185604 | ACATACCAGTCGAGGGGTTC | 1.8 |
| 185603 | CATACCAGTCGAGGGGTTCT | 27.5 |
| 185602 | ATACCAGTCGAGGGGTTCTG | 76.8 |
| 185320 | AGTACGTAGAAACGTACATC | 8.3 |
| 185319 | GTACGTAGAAACGTACATCT | 65.7 |
| 185181 | CTGGTTCACACGGATATACT | 51.7 |
| 185180 | ACTGGTTCACACGGATATAC | 31.4 |

FIGURE 12D

| 185166 | CAAGCGGACGGGACAGATCC | 29.2 |
|---|---|---|
| 184987 | ATCTAGAGTAAGGACTCCGG | 68.6 |
| 184958 | CTACTACGTGTGGCCATCAA | 33.2 |
| 184954 | AATTCTTTTGCTACTACGTG | 14.9 |
| 184429 | GTAAGTGGATAGGCGGTTTT | 30.0 |
| 183819 | ATCTTAGTCCTATTATCCGT | 33.3 |
| 183822 | GCACATGGCCTACGGATAAT | 59.0 |
| 183811 | ACACTTTCCGTATTAGCACT | 21.2 |
| 183734 | ATCTGCCAGTAGGTAGTCCG | 58.3 |
| 183736 | ACCAACCTCGGACTACCTAC | 44.3 |
| 183581 | GCTTATGATCTCGAAGAGTC | 31.9 |
| 183534 | AAGCAGCTAATAGTGACGAC | 31.3 |
| 183533 | AGCAGCTAATAGTGACGACA | 47.5 |
| 183311 | GTGAATGTGGATACGGTTTC | 37.1 |
| 183270 | TTTAACGAATATGGGTCACG | 5.7 |
| 183269 | TTAACGAATATGGGTCACGT | 18.0 |
| 183144 | TATGCCGTTGGTTGATATCC | 29.1 |
| 183120 | ACTATTATGCTTGACCAAGC | 10.7 |
| 183054 | CAAAATGAGGCAGCCGTAAT | 28.6 |
| 182400 | AACATCTGCTAAGATGTCGA | 24.0 |
| 182061 | GTCAAACCATCGTAGTCAGT | 15.5 |
| 182060 | TCAAACCATCGTAGTCAGTC | 7.7 |
| 182059 | CAAACCATCGTAGTCAGTCG | 30.8 |
| 182062 | TCTTCCCCGACTGACTACGA | 34.2 |
| 182055 | GTATTTAAGGTGTACACGAT | 30.6 |
| 181660 | GACACCATAAGCTACGTGTA | 59.1 |
| 181658 | CATAAGCTACGTGTATGGAC | 53.7 |
| 181661 | CAGTCCATACACGTAGCTTA | 33.4 |
| 181240 | TGGAAAGAATTACTACCACG | 51.1 |
| 181160 | TTCATGACTTCGCATACCAC | 5.5 |
| 181032 | GGGCTGTGGGACTACATAAC | 16.9 |
| 181030 | CCAACCCAGGTATAGGTCAC | 32.7 |
| 180840 | CATACAGTCACGCCTTTTGT | 20.2 |
| 180766 | AAACCTGTACGTATACTACC | 41.3 |
| 180768 | GATCCAGGTAGTATACGTAC | 53.2 |
| 180731 | ACATGCTTATTGATACGCTC | 14.7 |
| 180730 | CATGCTTATTGATACGCTCT | 35.9 |
| 180695 | ACAGAGGAGCACGTTTAGGC | 34.6 |
| 180630 | CTAGGGCTCAGTTAGTTGAT | 33.2 |
| 180612 | CCCAGAAACTGAATTCGATG | 10.9 |
| 180609 | AACTGAATTCGATGTGGGAT | 7.9 |

FIGURE 12E

| 180516 | GGCCCCCCTGATCCACCATT | 52.3 |
|---|---|---|
| 180505 | GCCACAAAAGCGAAGTGCCC | 51.9 |
| 180439 | GCTAGCCAGTCCCTACCACG | 47.8 |
| 180438 | TGAGCAAAGTCCTCGTGGTA | 13.8 |
| 180381 | CTTCCTCCCAATCGGATGTA | 49.5 |
| 180389 | CTTACATCCGATTGGGAGGA | 32.3 |
| 180386 | GGACCTTACATCCGATTGGG | 54.1 |
| 180373 | GGGATTGCTGCCGATATTCA | 56.9 |
| 180371 | GATATTCACGGCCATATCAA | 45.5 |
| 180372 | ATTGATATGGCCGTGAATAT | 48.5 |
| 180355 | CACCTAGAAGTAGTCTCATC | 23.8 |
| 180266 | TCAGCTGAGTACGTGAACAC | 67.6 |
| 180265 | ATCAGCTGAGTACGTGAACA | 33.6 |
| 180207 | GCCAACATGTCTACCATACC | 53.9 |
| 180196 | ATTCTGATAATGACCTACGG | 52.8 |
| 180192 | ATAATGACCTACGGAGGGTA | 37.8 |
| 180194 | CCTCAGGCCATACCCTCCGT | 40.1 |
| 180175 | TATAAGTTGACCCTTCCCGA | 47.2 |

FIGURE 14A
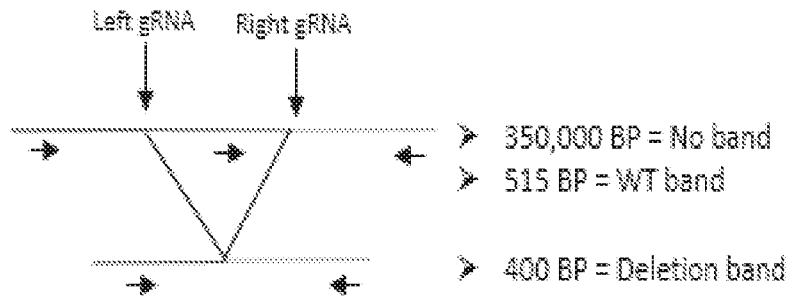
FIGURE 14B
Subset of promising clones
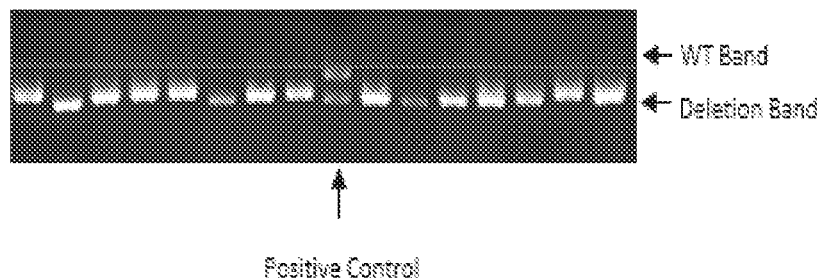
FIGURE 14C
| Positive Clones | 26/100 |
| % Positive Clones | 26% |

FIGURE 19A

| SEQ ID NO | Sequence | PAM | Cutting percentage estimate |
|---|---|---|---|
| 147118 | GTACATCTAGGAGGGAGCTC | TGG | 46 |
| 155566 | GCACAGCCAGCCCAGATGTA | GGG | 42 |
| 155568 | TCTCGCAGGAGCCCTACATC | TGG | 42 |
| 148128 | CTCCAGTGTCCCTGTCACAT | GGG | 37 |
| 152460 | ATGAGGTGCAAAGCAGCCAT | AGG | 37 |
| 136774 | TGGGAGAGTAACATCTGGTA | GGG | 33 |
| 141161 | AGGGATGTGAATGAATCAGT | AGG | 33 |
| 144187 | GGAGACAGGAGGGAGAAAGG | TGG | 33 |
| 150266 | GAGCAATGCAGACTAGGAAT | GGG | 33 |
| 144200 | GGAAAGGAGGAAATGGAAGA | GGG | 29 |
| 145692 | ACACACAGCTGGGTTATCAG | AGG | 29 |
| 148083 | GCAACCACACCACAAATACT | AGG | 29 |
| 149491 | AGCCTAGCCTACCTTCAACA | TGG | 29 |
| 149492 | AAGTGTTCTGACCATGTTGA | AGG | 29 |
| 151562 | TAAGACTACTGTAACAGTCC | AGG | 29 |
| 137443 | AGAGATGGCAAAAGGAACTT | TGG | 25 |
| 139634 | AGACAGCAGAAGAGGGTTAG | GGG | 25 |
| 139727 | AACATCCGAATGGAGAAGAG | AGG | 25 |
| 139793 | TTGCAGTGAAGTGTTGCTGG | GGG | 25 |
| 140099 | TGTAGTAATTGCTACGCTGT | AGG | 25 |
| 140846 | CCTCCCCTACATCCCTTAGA | GGG | 25 |

FIGURE 19B

| | | | |
|---|---|---|---|
| 140875 | TGGCATTGAAGATGAAGGAC | AGG | 25 |
| 141455 | GTACATCTCCCTGGCTTGTA | TGG | 25 |
| 142903 | AAGAAGGAAAGAAAGGGTAT | CGG | 25 |
| 142930 | TAACTTCTAAGGATCTTGGG | AGG | 25 |
| 144071 | GAATTGATGGGACAATGTGT | GGG | 25 |
| 144198 | AGGAAATGGAAGAGGGATGG | TGG | 25 |
| 145433 | TACTCTGGTGACACAACCTG | TGG | 25 |
| 146015 | ATGATGACTAAATATGCCAT | TGG | 25 |
| 146037 | GCCATCCCTGCGCCAGTCAT | GGG | 25 |
| 146066 | TATCTGTACACTGCTGGGAA | AGG | 25 |
| 146305 | GAGAGAATGCACAATAGACA | TGG | 25 |
| 148098 | ACTAGCCAAGAGCAGGCACC | AGG | 25 |
| 149229 | GCTCTCAACTCCTCACTGGA | GGG | 25 |
| 150627 | TCCAGAGACAAAGCTAGCTA | GGG | 25 |
| 150656 | TGGAAACAAGGAGTACCAAA | GGG | 25 |
| 150671 | GACTCTGATCCCCAGCTCAA | GGG | 25 |
| 150673 | CAGAGAAGGAACCCTTGAGC | TGG | 25 |
| 152763 | GAATTGACAGTTACAGATGT | GGG | 25 |
| 153531 | TAACAGGAAAGGCACTACAG | TGG | 25 |
| 136492 | AAGACAGCTATTGAAGTAAG | TGG | 21 |
| 137567 | GTTAGAAGTGGTTCCAAGGT | GGG | 21 |
| 137568 | TAGTGATGACAGTCCCACCT | TGG | 21 |
| 138502 | TCATCCATAAGCAGCAACTC | TGG | 21 |

FIGURE 19C

| 138514 | GAATGAGAAGTGGAGTCAGA | AGG | 21 |
|---|---|---|---|
| 139580 | CAGGTAGTACTCCTATTTCT | AGG | 21 |
| 139581 | AGTACTCCTTTCCTAGAAAT | AGG | 21 |
| 141151 | AAACAACAGGAACACACAGT | GGG | 21 |
| 141156 | TGGGTGGCAAATTCAGCCCA | GGG | 21 |
| 141507 | AATCAGAAAGGCCAGTCTCC | TGG | 21 |
| 141512 | AAAGGCCAGTCTCCTGGGGT | GGG | 21 |
| 141509 | TAGAACCCACCCCAGGAGAC | TGG | 21 |
| 141942 | CCAGCTGCTAGGAGTGCTGC | TGG | 21 |
| 141954 | TAGCGGCCCAGACTAAGACA | AGG | 21 |
| 142085 | CCAGTGCATGACTTGACACG | GGG | 21 |
| 142148 | GCATGCTCACCTCAATCTCA | GGG | 21 |
| 142901 | GGAAAGAAAGGGTATCGGAT | AGG | 21 |
| 143381 | GTTAGCTGGCTGTGATGGTG | TGG | 21 |
| 143418 | GAGGACGGGTCCAGACACAA | TGG | 21 |
| 144192 | GAGGGATGGTGGGAGACAGG | AGG | 21 |
| 144201 | AGGAAAGGAGGAAATGGAAG | AGG | 21 |
| 145652 | AACACAGTGATGAACAACTG | TGG | 21 |
| 146029 | GATGGAGAGGTCTAGCAATG | CGG | 21 |
| 146064 | ACATCTATCTGTACACTGCT | GGG | 21 |
| 146313 | GAAAGCGTATGAAAGGACAC | AGG | 21 |
| 146702 | GTTCCTCCAGTAACAGATTT | GGG | 21 |
| 146837 | TAGCTTTGTTGAATGAATGT | GGG | 21 |

FIGURE 19D

| 147207 | AGATGCAAGAGGAGAATCTG | TGG | 21 |
| --- | --- | --- | --- |
| 147385 | AATAATAAGAGCCAAGAAGT | AGG | 21 |
| 147386 | GCACTGGGCTGCCTACTTCT | TGG | 21 |
| 147395 | CAGCCCAGTGCAGAAGACAA | GGG | 21 |
| 148095 | ATCACAGCTGCATTTCTCCC | TGG | 21 |
| 148126 | GCTCCAGTGTCCCTGTCACA | TGG | 21 |
| 148129 | GAGGCTTCAGCCCATGTGAC | AGG | 21 |
| 148760 | GTAGGGTTAGTTTACTACTG | GGG | 21 |
| 149569 | AAATGCTAAGAAATTTAGAT | TGG | 21 |
| 149639 | CTGTGATCGGGATGATTGAG | AGG | 21 |
| 150481 | GCAAACAACGAGACAGCAGG | AGG | 21 |
| 150553 | TCTGGGAGTCTACTTGATCT | GGG | 21 |
| 150569 | GGTAAATGTGGCACAGGCAA | TGG | 21 |
| 150595 | AAAAAAGTAAGAGAGTGAGA | GGG | 21 |
| 150927 | CCATGATAGCAGCTGGGAGG | GGG | 21 |
| 151568 | AAGAGATGATGAGATTGTAC | AGG | 21 |
| 151593 | GTGGATGTCCAGCAGGGGTG | AGG | 21 |
| 151665 | CTGTACCCAAGTCCTCATCC | AGG | 21 |
| 152114 | TGATTGGATAAGAGCAACTT | TGG | 21 |
| 152120 | GATTACTCTGGCTGAAGAAT | AGG | 21 |
| 152347 | TACTTCAATATCTAAATATA | TGG | 21 |
| 152746 | AGTAGATCTGGAAAATCTAT | AGG | 21 |
| 153510 | AACTACCAAAAGGTTAAGAG | AGG | 21 |

FIGURE 19E

| | | | |
|---|---|---|---|
| 153549 | AAGGACCTGGCCTGGGACCA | GGG | 21 |
| 153980 | ATTGGAGGTGTCCTACCCAA | GGG | 21 |
| 153982 | ACCTTCTTCTCCCCTTGGGT | AGG | 21 |
| 154086 | AAGCTGGGGGATAAAGGTGT | TGG | 21 |
| 154381 | AAGGCTTGCATGGCAGATGG | AGG | 21 |
| 154967 | ACAAAACAAAACACAGGCTG | TGG | 21 |
| 154970 | AGGCTGTGGAGCTTGACATG | TGG | 21 |
| 155237 | AGTCTACAGATTGATGTCAA | TGG | 21 |
| 155531 | GCCAGCCATTGGCCAGGGGC | TGG | 21 |
| 155565 | TGCACAGCCAGCCCAGATGT | AGG | 21 |
| 155567 | CTCGCAGGAGCCCTACATCT | GGG | 21 |
| 155607 | TGTTGCATGACAACGGGATA | TGG | 21 |
| 136958 | AGTTACCGAAAGGGTTTTAC | TGG | 17 |
| 137226 | TATTGGGTCTTAACTGACTG | AGG | 17 |
| 137247 | CTTCTCCTCACCCAATGATT | GGG | 17 |
| 137249 | TTCCCACCACACCCAATCAT | TGG | 17 |
| 137301 | GACTCTGCAAGGAAGAGAGA | GGG | 17 |
| 137401 | GTGCATGACCATTATTTCCA | AGG | 17 |
| 137399 | TCTGCGCTCCTTGGAAATAA | TGG | 17 |
| 137474 | TACGTTCAAGAAGCTGGTCC | TGG | 17 |
| 137599 | TGTGGCTTCAGCAACAATGA | TGG | 17 |
| 137816 | CAGGGACAAGACCTCTTGAC | AGG | 17 |
| 137817 | CAGCCCCAGCTCCTGTCAAG | AGG | 17 |

FIGURE 19F

| | | | |
|---|---|---|---|
| 137910 | GAATGAGAAGAGCATTATAA | GGG | 17 |
| 138780 | AGTGCTACTCTGTTGAACAC | AGG | 17 |
| 139236 | CTGCATTGAGCAAGTCCGTC | GGG | 17 |
| 139370 | CCATCTCTCAGAATCCCATT | AGG | 17 |
| 139434 | ATTAGTTAGCAGAATTACGA | TGG | 17 |
| 139443 | TCAAGTTGAGAAGGGAAGCT | GGG | 17 |
| 139462 | GACATCATGTTGAAGGCCAT | GGG | 17 |
| 140845 | AGAGCTTGCATTCCCTCTAA | GGG | 17 |
| 140895 | AAGAGTCCTCCTAAGAGAGA | AGG | 17 |
| 140959 | GACATACTGACATACTTCTT | CGG | 17 |
| 140997 | TAACCAAAGGCCTCCGGAAG | TGG | 17 |
| 141058 | GAAGGCTGCAGGAAAGGCTA | GGG | 17 |
| 141081 | ATGTTTATGAGTGGGTGTGG | AGG | 17 |
| 141089 | GAGGAAGACAGCTGGGAAGA | AGG | 17 |
| 141511 | GAAAGGCCAGTCTCCTGGGG | TGG | 17 |
| 141792 | CTTATCAATGGCATTGCCTT | GGG | 17 |
| 141809 | CAAAAGTGGTACAAGCTAAC | TGG | 17 |
| 141993 | GAGGGCCCACTCCTGTTAAA | TGG | 17 |
| 141994 | CACCGAAGATGCCATTTAAC | AGG | 17 |
| 142090 | GTGCTAGGAAACGAAGAAAG | GGG | 17 |
| 142114 | ACTCCCTGAACGGTCAGCTG | AGG | 17 |
| 142133 | TGTTCTTGGGGTCAACGTGT | AGG | 17 |
| 142785 | TTAGAACAACCATAGAAGGA | GGG | 17 |

FIGURE 19G

| | | | | |
|---|---|---|---|---|
| 142843 | TGAACTCAGTGGGTTTATTT | GGG | | 17 |
| 142994 | CACAGGAAAAAAAGTCTTGC | TGG | | 17 |
| 143092 | TCTCATGTTGGAGATGACTG | GGG | | 17 |
| 143503 | GTGGAGAGGAGAGAGTAATT | TGG | | 17 |
| 144197 | GGAAATGGAAGAGGGATGGT | GGG | | 17 |
| 144641 | GAAGTTAAGGGTATATGATG | AGG | | 17 |
| 144649 | AGAGGAATTGTGATTCCATA | TGG | | 17 |
| 144695 | CTAGCATCCATTCTCTCTCC | TGG | | 17 |
| 145034 | GGTAGACTAGGCTACAGAAG | CGG | | 17 |
| 145201 | GATTGTGGTCAAGCCATCTC | TGG | | 17 |
| 145360 | ACAGTTGCCTAAGAACTGGT | GGG | | 17 |
| 145414 | GATGTTGGAGGTACCTGCTC | TGG | | 17 |
| 145582 | ACCAAGGTCCCAGAGTTCCT | AGG | | 17 |
| 145618 | CTTAAAAGAGGAATAATAAC | AGG | | 17 |
| 145933 | GGAAAGAAGAAAGTCAGGGA | GGG | | 17 |
| 146023 | ATTAGCTGAAGCATATTCAG | AGG | | 17 |
| 146056 | GTTCTTCAGGTGGTGCATGC | TGG | | 17 |
| 146058 | ACAGATAGATGTTCTTCAGG | TGG | | 17 |
| 146287 | ATGGAGAGAGGTAAGTCTGG | AGG | | 17 |
| 146372 | AATCCTCCAAAACCTAATAG | TGG | | 17 |
| 146603 | AGCCATTTCCCATGCTCCTT | AGG | | 17 |
| 146659 | AGTCTCTGAGGTGGTTAGAG | AGG | | 17 |
| 147672 | AAGTTAGACCTTAGTAAGTT | GGG | | 17 |

FIGURE 19H

| | | | |
|---|---|---|---|
| 147808 | AGCAATGGGAGCTCTTCAGT | GGG | 17 |
| 148065 | ATGCCAGTGCCTCTCTGTAG | TGG | 17 |
| 149010 | GTGGAAGAGAATTCAGGTAT | TGG | 17 |
| 149631 | GATGCCATGAAACATTCCTG | GGG | 17 |
| 150153 | ATGGCTTAATGCCCTTCCTG | GGG | 17 |
| 150155 | ACTCAACCTGCCCCCAGGAA | GGG | 17 |
| 150594 | GAAAAAAGTAAGAGAGTGAG | AGG | 17 |
| 150638 | AGAGGAAGTATGTAAAGAAA | TGG | 17 |
| 150669 | AGACTCTGATCCCCAGCTCA | AGG | 17 |
| 150672 | AGAGAAGGAACCCTTGAGCT | GGG | 17 |
| 150697 | CCTCATTCATTCCCAGGTAA | TGG | 17 |
| 150699 | TCATTGAATCCCCATTACCT | GGG | 17 |
| 150930 | TAGCCATGATAGCAGCTGGG | AGG | 17 |
| 151589 | TTAGTGGTGGATGTCCAGCA | GGG | 17 |
| 151604 | GACCCCCAAGATTTTGTTAC | TGG | 17 |
| 151652 | ATTTTTCTTATTGTTGTCTT | TGG | 17 |
| 151713 | CAGAGAATTCCCCTTGCCCC | CGG | 17 |
| 151715 | CACTATTCCTTCCGGGGGCA | AGG | 17 |
| 151726 | GTGGTTAAAAATATATCCAT | GGG | 17 |
| 151740 | GCTCACTCACTAAAACTTCA | AGG | 17 |
| 151769 | GGGAGCCATTCCCTTGACAT | GGG | 17 |
| 151771 | GCTGACAGCATCCCATGTCA | AGG | 17 |
| 151782 | GGCAAGTCTGAACTCACACA | GGG | 17 |

FIGURE 19I

| | | | |
|---|---|---|---|
| 151786 | CACTGCAGTTGCAGCTGCAG | TGG | 17 |
| 152068 | GGTTTATCAAGCCAAATGCC | TGG | 17 |
| 152070 | GAATAGAACACCCAGGCATT | TGG | 17 |
| 152071 | AGAACGCGAATAGAACACCC | AGG | 17 |
| 152082 | TTTATGTCCAATCAGTTACC | AGG | 17 |
| 152095 | TAAAGAAGTAATAAAGGGAA | TGG | 17 |
| 152125 | GGGTTTTAGAGGGATTACTC | TGG | 17 |
| 152256 | ATCCCTAGAATCTAACACAC | AGG | 17 |
| 152285 | ATGGCTTCTTATCCCCCTGA | TGG | 17 |
| 152521 | TACTGTAGTTAGAAGAAAAA | TGG | 17 |
| 152620 | TGGGACACTGGCTAGAGGAA | AGG | 17 |
| 153253 | AATTAAACTCAGGAGATGTG | GGG | 17 |
| 153496 | CCCCAAAGCACAACCCTAAC | TGG | 17 |
| 153548 | GAAGGACCTGGCCTGGGACC | AGG | 17 |
| 153550 | AGTAGGGGGTCCCTGGTCCC | AGG | 17 |
| 153632 | TCCTCAAAGTCTAATACGTC | AGG | 17 |
| 153961 | CTTATTAGCATGCCTCGTAT | AGG | 17 |
| 154101 | GCTGGGGAGGAGATTATCTC | TGG | 17 |
| 154107 | GCAGAGCAGGCTGGAAGCTG | GGG | 17 |
| 154132 | TACAGGCAGAGAAAGGACTC | AGG | 17 |
| 154177 | ACAGCCATGTCCCTTTATTT | AGG | 17 |
| 154179 | CACAGACAATACCTAAATAA | AGG | 17 |
| 154388 | AGGACTTTGCATGGGTCTGA | AGG | 17 |

FIGURE 19J

| | | | | |
|---|---|---|---|---|
| 154437 | TTCTAAGCTATAACATCCTC | GGG | | 17 |
| 154493 | GGCCAGCATCAGCATAACCT | AGG | | 17 |
| 154630 | TCTATACTTTGCGAAGAACT | GGG | | 17 |
| 154727 | CTAGCCTACAGGATGATGAG | TGG | | 17 |
| 155368 | TAAAAGAAGCCCTACAATCT | GGG | | 17 |
| 155456 | GGAGGACCACAAGCTGACTT | GGG | | 17 |
| 155498 | AGGAACAATGCACACATCCC | TGG | | 17 |
| 155545 | CTGGCTGGATCAGGAATACA | AGG | | 17 |
| 155554 | AGGCCCACTGCCTGCAATTC | AGG | | 17 |
| 155563 | CAGGAGCCCTACATCTGGGC | TGG | | 17 |
| 136516 | AACTCTGGTCATCTGTGACA | TGG | | 12 |
| 136766 | TGGTAGGGGTAGCAGATTGG | GGG | | 12 |
| 136837 | AGGAATCAATGCTATTTCTA | AGG | | 12 |
| 136867 | CACTAGCTGAGCAAAGATGG | AGG | | 12 |
| 136889 | AAATAGCAACCCTATGAAAT | AGG | | 12 |
| 137176 | ACAACCTGAGGTATTATGGT | AGG | | 12 |
| 137266 | AGAGCCTTCCTTGGGAGACA | TGG | | 12 |
| 137343 | CAAAAGTGAGTGTATTAGTC | AGG | | 12 |
| 137558 | GGCCTCAGGAAAAGCTGAAC | AGG | | 12 |
| 137584 | TAGGGAAACGACAAAGAAAG | TGG | | 12 |
| 137619 | TCCAAGGCTAGGATAGACTT | GGG | | 12 |
| 137729 | AGTGGCAGAACTTCTAACAT | AGG | | 12 |
| 137827 | GGAGCTGGGGCTGTGAGTAA | AGG | | 12 |

FIGURE 19K

| | | | |
|---|---|---|---|
| 137860 | GCCCAATGCTACTGCCATAT | TGG | 12 |
| 137992 | ACTACAATGAAGGGAAACAG | TGG | 12 |
| 138013 | TTACCTCACTCCCGTTAAAA | TGG | 12 |
| 138271 | GGGGCTTAAAACCTGGATGT | TGG | 12 |
| 138273 | TACTCATCAACCCAACATCC | AGG | 12 |
| 138437 | TACAGGCTCTTGCCTCAGTG | AGG | 12 |
| 138506 | ATCTCAAGGTAAAACTTCAG | CGG | 12 |
| 138604 | ACATATTCCTCAGGGCTCTT | GGG | 12 |
| 138609 | TCAGGGCTCTTGGGTGACCA | GGG | 12 |
| 138648 | AGCATAACCTGAAGGGCCCT | AGG | 12 |
| 138700 | ACTAACATCTAAGTTAATAA | AGG | 12 |
| 138819 | CAATGTCCTCTAAGTGTTCA | TGG | 12 |
| 138913 | CCACTCTGGACATCAGACTT | GGG | 12 |
| 139106 | TATTACATGATGCCGAGGTT | TGG | 12 |
| 139256 | AATTAATACTGAAAAAATTG | AGG | 12 |
| 139275 | TGTATAGATTCCTCTGAATA | GGG | 12 |
| 139290 | AGTGAAATGTAACTATTTGA | GGG | 12 |
| 139461 | GGACATCATGTTGAAGGCCA | TGG | 12 |
| 139635 | AAGACAGCAGAAGAGGGTTA | GGG | 12 |
| 139733 | CCCCTTATATGTACGTCCAA | AGG | 12 |
| 139846 | TACAGTATGACAGCTTTTAA | AGG | 12 |
| 139860 | GACATACTTGTCTATTCCCT | AGG | 12 |
| 139868 | TAATTCTTATCATATAAAAA | TGG | 12 |

FIGURE 19L

| | | | |
|---|---|---|---|
| 139879 | CACTTGCACTGCGGCATGAA | AGG | 12 |
| 139928 | ATAATGTAAACAGCTCGGTT | AGG | 12 |
| 140011 | AGACAGAATAGGTGTTACTG | AGG | 12 |
| 140741 | CAAGGAAGTGTTGATGGATT | TGG | 12 |
| 140764 | AATGAAGTTAGAGAAAGATG | AGG | 12 |
| 140839 | ACAAGCTAGAAACAATGTGT | TGG | 12 |
| 140844 | CAGAGCTTGCATTCCCTCTA | AGG | 12 |
| 140863 | TGCAGGCAGGCTCTAAAAGC | TGG | 12 |
| 140867 | GGCCAAGAGCCAAGAAATGC | AGG | 12 |
| 140883 | ATTGGAAGATGCTACACTAC | TGG | 12 |
| 140909 | TGATTACATTGGGCGCACTG | GGG | 12 |
| 140942 | GATATGGACATCTTTGGCGG | GGG | 12 |
| 140965 | CATACTTCTTCGGGTGGGTT | CGG | 12 |
| 140987 | ACCAGGCTCCTGTGTCCTTG | TGG | 12 |
| 140991 | CTGTGTCCTTGTGGCAGACA | TGG | 12 |
| 141158 | TACTGATTCATTCACATCCC | TGG | 12 |
| 141448 | CTGGCTTGTATGGGGGTAAT | AGG | 12 |
| 141451 | CATCTCCCTGGCTTGTATGG | GGG | 12 |
| 141452 | ACATCTCCCTGGCTTGTATG | GGG | 12 |
| 141510 | TCAGAAAGGCCAGTCTCCTG | GGG | 12 |
| 141553 | GTTATGGAACCTGTATTCTT | TGG | 12 |
| 141552 | GGCACCATTCCAAAGAATAC | AGG | 12 |
| 141580 | GAGAATATTCCAGAATCTAG | AGG | 12 |

FIGURE 19M

| | | | |
|---|---|---|---|
| 141599 | ATGACAACACCTGAGAGTGA | GGG | 12 |
| 141602 | ACACCTGAGAGTGAGGGTAT | GGG | 12 |
| 141719 | GATCATTGCCTCCCACCCTC | TGG | 12 |
| 141721 | CAGATGAGCCCCCAGAGGGT | GGG | 12 |
| 141733 | TGTCAGAGAGGAGAATATTT | TGG | 12 |
| 141753 | TTCTCTATTATTTCTTCCCT | GGG | 12 |
| 141937 | CAGCAGCACTCCTAGCAGCT | GGG | 12 |
| 141998 | ATCTTCGGTGTGTCCTTACA | TGG | 12 |
| 142058 | CCACGGGAATTTCCATAAGG | GGG | 12 |
| 142077 | CACTGGATGTGGGCTACTCC | AGG | 12 |
| 142092 | AAGTGCTAGGAAACGAAGAA | AGG | 12 |
| 142105 | CGTTCAGGGAGTTCTTAAGC | TGG | 12 |
| 142111 | AGGGCCTCAGCTGACCGTTC | AGG | 12 |
| 142127 | GGTCAACGTGTAGGGGCAGA | GGG | 12 |
| 142165 | GAAATCAGTCCCAAATGCCT | AGG | 12 |
| 142208 | AGACTTCCTGCATATCTCTC | AGG | 12 |
| 142225 | CAGACGACAGAGTGTGCCCA | AGG | 12 |
| 142461 | TCTCTAGAGCAACTGTCTGA | GGG | 12 |
| 142477 | TCACCATGATGTACCTACCA | GGG | 12 |
| 142519 | CTCTACACAAATGGTTTCCA | TGG | 12 |
| 142663 | TTTGCATGTACGATAATAAC | AGG | 12 |
| 142802 | CGAATGGCCATGTAAATATT | GGG | 12 |
| 142932 | TCCTAACTTCTAAGGATCTT | GGG | 12 |

FIGURE 19N

| 143098 | CTGGGGTTGGAGGAAAAAGT | TGG | 12 |
| --- | --- | --- | --- |
| 143100 | GAGGAAAAAGTTGGGACATA | CGG | 12 |
| 143105 | TGGAGGTGCTGCACTGACCC | TGG | 12 |
| 143397 | CCAGAAGTTCAAGAGCAACC | TGG | 12 |
| 143441 | ACTAGAAGAGGACATTTACT | GGG | 12 |
| 143485 | AGAAGTAGATTGTAGTGAGA | GGG | 12 |
| 143486 | AAGAAGTAGATTGTAGTGAG | AGG | 12 |
| 143963 | CCAACAAATGTACATGTCTC | TGG | 12 |
| 144017 | GTGTAAGAAGTTGAGGGGGG | TGG | 12 |
| 144076 | ATTGTCCCATCAATTCTTCC | AGG | 12 |
| 144074 | TATAGCCCTGGAAGAATTGA | TGG | 12 |
| 144117 | CCACACATTGCACTGTTACC | TGG | 12 |
| 144152 | ATCCTGAACACCTGGCCAAA | CGG | 12 |
| 144185 | GACAGGAGGGAGAAAGGTGG | AGG | 12 |
| 144235 | GGAAGGAAAGCAGGAAAAAG | GGG | 12 |
| 144269 | AAGGAAGGAGAGAACAAAGA | AGG | 12 |
| 144495 | GAACATGTAGAATAAGTTGG | AGG | 12 |
| 144548 | AGAGTCCAGTTCACCTTGTT | TGG | 12 |
| 144667 | TAAAACGAGAAGGGCAATCC | AGG | 12 |
| 144718 | CAGAGAAGTTGAAAACTATG | AGG | 12 |
| 144782 | TGAGCTGCCACTAAGTACCT | GGG | 12 |
| 144999 | GAGACTACTGAGCACATCAA | TGG | 12 |
| 145008 | GGACTCACAAACCCGTCACA | AGG | 12 |

FIGURE 19O

| | | | |
|---|---|---|---|
| 145009 | AGTCCACACTTCCTTGTGAC | GGG | 12 |
| 145022 | TATTATCTGGTAACTTCTGC | AGG | 12 |
| 145030 | AGCTATGTCAATGGTAGACT | AGG | 12 |
| 145086 | AGATAAACTTGGGCTCAGGT | AGG | 12 |
| 145106 | ACAATGTAACTTCAAAACCT | GGG | 12 |
| 145200 | AGGAAACGAAGATCCAGAGA | TGG | 12 |
| 145356 | AGAAACAGTTGCCTAAGAAC | TGG | 12 |
| 145357 | ACCATTTCCCACCAGTTCTT | AGG | 12 |
| 145408 | CTGCTCTGGCAGATTTCAAC | CGG | 12 |
| 145421 | ACCTCCAACATCAAGGAAGA | TGG | 12 |
| 145432 | GCAGTTTCCTTAGTAACCAC | AGG | 12 |
| 145444 | GAGTAGGAGCTAAAATATTT | TGG | 12 |
| 145583 | GTTCTCTGCCCTAGGAACTC | TGG | 12 |
| 145622 | TAACAGGGTAAATGTCATAA | GGG | 12 |
| 145658 | GTGGTGAGAAACTGGAGATA | AGG | 12 |
| 145697 | TTATCAGAGGTGAGTGGTGA | GGG | 12 |
| 145726 | GCTGCAAAAGACATCTCAAC | AGG | 12 |
| 145831 | AAGGAGCTAAATATCCAGAG | AGG | 12 |
| 145846 | GGAACTAACTGCAGAACACC | AGG | 12 |
| 145897 | ATGATCATTTCCACCTCATT | AGG | 12 |
| 145929 | AAGAAGGAAAGAAGAAAGTC | AGG | 12 |
| 145986 | GTCAGGAAGCCAGGCAGTAA | GGG | 12 |
| 146024 | GAAGCATATTCAGAGGATGA | TGG | 12 |

FIGURE 19P

| | | | | |
|---|---|---|---|---|
| 146033 | ATCTGCCCATGACTGGCGCA | GGG | | 12 |
| 146038 | TGAGATTATCTGCCCATGAC | TGG | | 12 |
| 146049 | GAAGAGAAGACCAGAAATAC | TGG | | 12 |
| 146073 | TACACTGCTGGGAAAGGGAG | GGG | | 12 |
| 146089 | TTGAGCACCTCCTATACTCC | AGG | | 12 |
| 146116 | TTAACAGCCACCCATTAGAA | TGG | | 12 |
| 146117 | CTCCATTCTTCCATTCTAAT | GGG | | 12 |
| 146118 | CCTCCATTCTTCCATTCTAA | TGG | | 12 |
| 146139 | TTTTCACGAGAAGATAATGG | AGG | | 12 |
| 146233 | ATTGGAGGCATCTTGAGGTA | AGG | | 12 |
| 146304 | AGAGAATGCACAATAGACAT | GGG | | 12 |
| 146312 | GAAAGGACACAGGTTTGAAA | TGG | | 12 |
| 146604 | GTTGTCATCCCTAAGGAGCA | TGG | | 12 |
| 146628 | GCCCAGGCATGAACAGACTT | GGG | | 12 |
| 146637 | CAAGATAGGGGCATAAGAAA | CGG | | 12 |
| 146883 | CTCCAATGTTGCTTACATGG | AGG | | 12 |
| 147001 | CCTTTACCAAACCATCTTCA | GGG | | 12 |
| 147002 | GATAACATCTACCCTGAAGA | TGG | | 12 |
| 147232 | TCCACTCCTTGAATATGGAT | TGG | | 12 |
| 147270 | GGTTATAAGTTGAGACGGTG | TGG | | 12 |
| 147320 | TTTGCGTACAAGTGTTTAAC | AGG | | 12 |
| 147407 | ACCACGCTATTGATGAAGGG | TGG | | 12 |
| 147489 | TAGCTTATCATCTCCTCTGG | TGG | | 12 |

FIGURE 19Q

| | | | | |
|---|---|---|---|---|
| 147575 | CATACCACTCTGGTGTGGAT | AGG | | 12 |
| 147648 | GTGAAAAGGTGTAGCCACTA | TGG | | 12 |
| 147762 | CCCATGTTGTAGCATAGGAA | AGG | | 12 |
| 147807 | GAGCAATGGGAGCTCTTCAG | TGG | | 12 |
| 148058 | TCCTCATTGCAATATTTGTG | GGG | | 12 |
| 148072 | GCTTCATCAAGATCCTCTTC | TGG | | 12 |
| 148097 | CTAGCCAAGAGCAGGCACCA | GGG | | 12 |
| 148101 | TCTTTGCACTAGCCAAGAGC | AGG | | 12 |
| 148167 | GTGTCAGAGATGAGATTCCT | TGG | | 12 |
| 148357 | ACAAAAGAGATCAAAATCAA | GGG | | 12 |
| 148568 | CATTCAAAGTAAATATTGAT | AGG | | 12 |
| 148759 | AGTAGGGTTAGTTTACTACT | GGG | | 12 |
| 148826 | ACTTGTGAAGATCTTCAGGA | AGG | | 12 |
| 148837 | ACATCTGGTAATATTAAGTT | GGG | | 12 |
| 148852 | GGCTATGGTTTGGGGGTTTT | GGG | | 12 |
| 148900 | AAATGTCTACTACATGTTTG | TGG | | 12 |
| 148978 | CAGGGGCTACAGATATGTAA | AGG | | 12 |
| 148996 | ACATCTGTGATGATACTGGT | AGG | | 12 |
| 148998 | TGTGATGATACTGGTAGGAT | AGG | | 12 |
| 149131 | ATTGATCCTATTGGGTAATT | GGG | | 12 |
| 149228 | TGCTCTCAACTCCTCACTGG | AGG | | 12 |
| 149230 | CTTGCACACTCCCTCCAGTG | AGG | | 12 |
| 149238 | AGTGTGCAAGCAAACGAGGT | GGG | | 12 |

FIGURE 19R

| | | | |
|---|---|---|---|
| 149424 | TAAGTTCCCACTTTGAGCTG | CGG | 12 |
| 149529 | GAAATAAAGAAATATACAGA | GGG | 12 |
| 149584 | AGACTACAGCACAGTTGGAC | TGG | 12 |
| 149648 | AAGTGGATGTGACCAGGGAA | TGG | 12 |
| 149702 | CCAAATGCTGAATAGCTGCA | TGG | 12 |
| 149772 | TCACTCCATTGGGGTGACAC | TGG | 12 |
| 149866 | GCAGTCATCTTGGAACCTGG | AGG | 12 |
| 150053 | AAGGATTGGTAATTTATCGT | GGG | 12 |
| 150104 | CCTGAACTAGAGATAATCAT | TGG | 12 |
| 150159 | TTAATGCCCTTCCTGGGGGC | AGG | 12 |
| 150160 | CAGTCACTCAACCTGCCCCC | AGG | 12 |
| 150290 | TGGTTTTTCAGTGATCTCTG | TGG | 12 |
| 150311 | CCTTTAAATAGTCTTACCCA | AGG | 12 |
| 150363 | TACTGAAGAGTACATGTGAC | AGG | 12 |
| 150696 | TGCCTTCCTCATTCATTCCC | AGG | 12 |
| 150693 | CCATTACCTGGGAATGAATG | AGG | 12 |
| 150856 | CTGTACCCCCCATTGTATCC | TGG | 12 |
| 150993 | TCTGCACTGTCCCAGCAGAG | AGG | 12 |
| 150995 | CTCATGGAAAACCTCTCTGC | TGG | 12 |
| 151042 | AGGCCTTAGTGGCTTACATG | TGG | 12 |
| 151439 | CGCTCCTTACCTCCCAAACT | AGG | 12 |
| 151520 | TTCACACAGCTAAGATGCAT | AGG | 12 |
| 151539 | TGCATAGTGTTACAAGTGAA | AGG | 12 |

FIGURE 19S

| | | | | |
|---|---|---|---|---|
| 151668 | CAGGGCCTGGATGAGGACTT | GGG | | 12 |
| 151725 | AGTGGTTAAAAATATATCCA | TGG | | 12 |
| 151767 | AGCATCCCATGTCAAGGGAA | TGG | | 12 |
| 151781 | AGGCAAGTCTGAACTCACAC | AGG | | 12 |
| 152083 | TTATGTCCAATCAGTTACCA | GGG | | 12 |
| 152080 | AACAGGCCCTGGTAACTGAT | TGG | | 12 |
| 152118 | CTGAAGAATAGGTAACTGAT | TGG | | 12 |
| 152166 | ATGGCTGAAGCACTGAGTTG | GGG | | 12 |
| 152167 | TATGGCTGAAGCACTGAGTT | GGG | | 12 |
| 152168 | GTATGGCTGAAGCACTGAGT | TGG | | 12 |
| 152286 | CAGGAGATGTCACCATCAGG | GGG | | 12 |
| 152572 | TGAGTGTGCATCCCTTGGTA | TGG | | 12 |
| 152573 | TCAGCAATAAGCCATACCAA | GGG | | 12 |
| 152583 | ATGAGTGGATAGACCTGCGT | GGG | | 12 |
| 152593 | AGTAAAACCCAGTGTGAGCA | AGG | | 12 |
| 152684 | TACCCTTTTGACGGCCGAAG | GGG | | 12 |
| 152841 | AGAATTGGTCCTAGAGTATA | TGG | | 12 |
| 152986 | CACATTCAAAGAGGTTGGAA | GGG | | 12 |
| 153008 | CATACAGCTTGAGGAATCTC | TGG | | 12 |
| 153023 | AGTTTTTCTTGTCTTTCAGC | TGG | | 12 |
| 153055 | TGTGCAGGTTCAAAGGAAAA | GGG | | 12 |
| 153173 | GCATGGGCTGGCAAGCACTT | TGG | | 12 |
| 153201 | CAAGACACAGTCAAGAATGA | GGG | | 12 |

FIGURE 19T

| | | | |
|---|---|---|---|
| 153427 | ACCCTACCGCTCAAAATGGA | AGG | 12 |
| 153533 | TGCTCACTGGTTAACAGGAA | AGG | 12 |
| 153581 | GGAGTGACAACAGAAAGCCC | TGG | 12 |
| 153608 | GAGTCTCTCCAGCTGCTCCA | AGG | 12 |
| 153682 | ACCACAACAGGAAAGGGTGT | GGG | 12 |
| 153901 | TAAATACAAATAATTCAATT | GGG | 12 |
| 153960 | ATCGGAAGGAAGCCTATACG | AGG | 12 |
| 153977 | TAGTGTGGAACATGCATTGG | AGG | 12 |
| 153991 | ACCCAAGGGGAGAAGAAGGT | GGG | 12 |
| 154109 | TTGCAGAGCAGGCTGGAAGC | TGG | 12 |
| 154113 | AGCTCTCCCACTTGCAGAGC | AGG | 12 |
| 154154 | GGCTGAGTGCTAAGGGGAAA | TGG | 12 |
| 154238 | TCAACTAGAAAACTCTGGGC | CGG | 12 |
| 154474 | CCTTGCTGCACACAGCAGAA | GGG | 12 |
| 154703 | GCAGTTTTCCAAGAGAGGGC | GGG | 12 |
| 154719 | ATCATCCTGTAGGCTAGATT | AGG | 12 |
| 154736 | GATATCTGACAGCTGGCTGT | TGG | 12 |
| 154973 | GCTAGAAAGCAAGCAAGCAA | GGG | 12 |
| 155109 | GACATAGGAGAAGACAAGAG | TGG | 12 |
| 155133 | TGAAAGATGAGTATCTCTCA | TGG | 12 |
| 155144 | ATCAGTGAGACTAGAGGAGT | GGG | 12 |
| 155190 | TATTGTCTATAGTGTGGTCA | GGG | 12 |
| 155200 | AGAACAACTAAGCAGGGAGA | TGG | 12 |

FIGURE 19U

| | | | |
|---|---|---|---|
| 155213 | TCTCAAATGTCAGTGTGCAC | AGG | 12 |
| 155215 | AGTGTGCACAGGATTCACCT | GGG | 12 |
| 155367 | ATGCACTGTCCCCAGATTGT | AGG | 12 |
| 155370 | TTAAAAGAAGCCCTACAATC | TGG | 12 |
| 155457 | GGGAGGACCACAAGCTGACT | TGG | 12 |
| 155532 | TCCAGCCAGCCATTGGCCAG | GGG | 12 |
| 155606 | GTTGCATGACAACGGGATAT | GGG | 12 |
| 136261 | TACTCAAGGCATTCAGACAG | TGG | 8 |
| 136286 | TTGACAGGTGAGAAATCTCA | GGG | 8 |
| 136406 | ATATGATGTTCTACCACATG | AGG | 8 |
| 136414 | TGAAGATGAAGAGATGAAAG | TGG | 8 |
| 136512 | AGAGTTTCACATTCTAACAC | TGG | 8 |
| 136534 | TGACTTCATCTGAGGTTTCT | GGG | 8 |
| 136536 | TTGACTTCATCTGAGGTTTC | TGG | 8 |
| 136558 | TCAGCACTAGGCACTATTCT | AGG | 8 |
| 136607 | AAAAGCTGTTCATTGTGGTC | AGG | 8 |
| 136633 | TGTGAAACCTGTTCTCTAGT | TGG | 8 |
| 136787 | AAAGGACCAGAGGTCATATG | AGG | 8 |
| 136800 | TGTTTGTTATGACTAAAGCT | AGG | 8 |
| 136827 | CATGGATTCTATCATTCTAG | AGG | 8 |
| 136865 | TTCCACTAGCTGAGCAAAGA | TGG | 8 |
| 136938 | TCAGAAGGTAAAAGAGTTTA | CGG | 8 |
| 136955 | TAGCCTTTCTAGTTACCGAA | AGG | 8 |

FIGURE 19V

| | | | |
|---|---|---|---|
| 136971 | TCTCACTGAGCATCTTCTTC | TGG | 8 |
| 136968 | GAAGAAGATGCTCAGTGAGA | TGG | 8 |
| 136981 | TTTGGCCACTCTATTTGGAG | AGG | 8 |
| 136988 | TAAGTGGAAGACAATGAGGA | TGG | 8 |
| 136992 | ATGAGAAGTGAGGAAGTAAG | TGG | 8 |
| 137018 | TGTTCTACTAGCACCTCCAT | CGG | 8 |
| 137089 | CAAAGTCAGGAAATTTAGCG | TGG | 8 |
| 137122 | GTGTTATAAAGTTCAAAGAA | AGG | 8 |
| 137148 | GTTGTGTCACTCATTGAGCT | AGG | 8 |
| 137168 | AACAAACGAGTAGTGATGAC | AGG | 8 |
| 137205 | CACTTGGGTATGAGGAGCAG | TGG | 8 |
| 137218 | TGGCCACCATGAGAATATGC | AGG | 8 |
| 137215 | AGGCCTGCATATTCTCATGG | TGG | 8 |
| 137246 | ACTTCTCCTCACCCAATGAT | TGG | 8 |
| 137248 | TCCCACCACACCCAATCATT | GGG | 8 |
| 137267 | GAGCCTTCCTTGGGAGACAT | GGG | 8 |
| 137264 | AAGAAGTCCCATGTCTCCCA | AGG | 8 |
| 137286 | CATCCCAGTGTGCGGTCTAG | TGG | 8 |
| 137316 | AACATCTCTTGCACCTTCCT | TGG | 8 |
| 137381 | CATCTTAAGAGGCCAGCCCA | TGG | 8 |
| 137407 | GGAGCGCAGAATTTAACTGG | AGG | 8 |
| 137444 | GAGATGGCAAAAGGAACTTT | GGG | 8 |
| 137445 | AGATGGCAAAAGGAACTTTG | GGG | 8 |

FIGURE 19W

| | | | |
|---|---|---|---|
| 137596 | ATCATTGTTGCTGAAGCCAC | AGG | 8 |
| 137629 | ATGTGTACTAGCTGAGTGCT | TGG | 8 |
| 137652 | TATGCTGTGATAGACTCTTT | TGG | 8 |
| 137774 | ATTATATTCTGAATCAGTCA | TGG | 8 |
| 137796 | CCTCAAGGCCTGAAAGGCTA | AGG | 8 |
| 137800 | AGGCCTGAAAGGCTAAGGGG | AGG | 8 |
| 137821 | CAAGACCTCTTGACAGGAGC | TGG | 8 |
| 137834 | GATGAGAGGAGAGTGAGTCG | AGG | 8 |
| 137855 | CATTGGGCTTGCTTGTCTAT | TGG | 8 |
| 137864 | GCCATATTGGTCAACCTCCT | AGG | 8 |
| 137862 | CCCTAGGAGGTTGACCAATA | TGG | 8 |
| 137881 | TATAAAAAAATAATAATAA | TGG | 8 |
| 137888 | TTGCTGAGAATTCCCATATG | TGG | 8 |
| 137894 | CAAAGACTTCATATCAAGTA | TGG | 8 |
| 137901 | CAGCTGAACTTTGGCAGATT | TGG | 8 |
| 137909 | AGAATGAGAAGAGCATTATA | AGG | 8 |
| 138252 | CGGGGCCTGTCAAGGGGTGA | GGG | 8 |
| 138257 | GTCAAGGGGTGAGGGGCAAG | GGG | 8 |
| 138272 | GGGCTTAAAACCTGGATGTT | GGG | 8 |
| 138392 | ACCAAACACACAATATTCCA | AGG | 8 |
| 138496 | TTATGGATGAGCAAAGATTG | TGG | 8 |
| 138518 | ATGAGAACCAGAATGAGAAG | TGG | 8 |
| 138569 | GGTGAGTCCACTGATGGATC | TGG | 8 |

FIGURE 19X

| | | | |
|---|---|---|---|
| 138574 | AAGGTATAGCTGCTATATTG | TGG | 8 |
| 138577 | TTAAATCATACATTTCATAA | AGG | 8 |
| 138735 | GGAAGCTGCAGCAGAAAAGT | TGG | 8 |
| 138741 | TGTGAATGCCGAGAGAGGTG | AGG | 8 |
| 138765 | TGTCTTAGTGGTCTGGATAG | AGG | 8 |
| 138851 | AAGGAGAGGAAGAGAGATGA | GGG | 8 |
| 138844 | TCATCTCTCTTCCTCTCCTT | GGG | 8 |
| 138854 | ATGAGGGAATGGCTGATCAG | TGG | 8 |
| 138907 | AAGCCTAGGAAACACCACTC | TGG | 8 |
| 138973 | CCAGTATGAATGGTGTGAGA | CGG | 8 |
| 139065 | TAGCTCCACATGAGAACACG | TGG | 8 |
| 139079 | GAAACGGAGGACTACTAGAG | TGG | 8 |
| 139104 | ATCATTTGTACTCCAAACCT | CGG | 8 |
| 139154 | GCTGCATGGGAGGCTGACAC | AGG | 8 |
| 139163 | CAGCCTCCCATGCAGCTGGC | AGG | 8 |
| 139164 | AGCCTCCCATGCAGCTGGCA | GGG | 8 |
| 139285 | TTGTAATTTATCTTCTGCTT | TGG | 8 |
| 139294 | AATTAGGAGGAGTATGTACC | AGG | 8 |
| 139330 | ACAGTAGGGAATGTGCCTCA | TGG | 8 |
| 139346 | AACTTTCAATGCAGTTGGGG | AGG | 8 |
| 139353 | CTGCGTGTGCGAGCATGCAT | GGG | 8 |
| 139383 | TTTATATGGGACCAGGTTCA | GGG | 8 |
| 139384 | TATGGCACCTTCCCTGAACC | TGG | 8 |

FIGURE 19Y

| | | | |
|---|---|---|---|
| 139389 | GTTCAGGGAAGGTGCCATAG | AGG | 8 |
| 139395 | CAACATGAACTGTAACTTAG | AGG | 8 |
| 139425 | CAGAGTGGTTGAGAAAGAGT | GGG | 8 |
| 139440 | GGCTGTGATCAAGTTGAGAA | GGG | 8 |
| 139450 | AAGCTGGGGCCAGAATGTGA | GGG | 8 |
| 139449 | TGTTCTGAGCCCTCACATTC | TGG | 8 |
| 139456 | GAACACTAGATGCCCAAATA | AGG | 8 |
| 139473 | GAAGAATGCCACAATAAAAG | TGG | 8 |
| 139482 | TTTTCCATTTCTTTCTTGGA | AGG | 8 |
| 139490 | GAGATACAAGAGGCTTTTCT | TGG | 8 |
| 139511 | GACAGTTTTTACAAGCAATG | GGG | 8 |
| 139538 | TTCTTACATTCCTACTCTAA | AGG | 8 |
| 139613 | CTACAGGTAGTATCAGCGAA | TGG | 8 |
| 139633 | GACAGCAGAAGAGGGTTAGG | GGG | 8 |
| 139644 | CCTCTTCTGCTGTCTTCACA | TGG | 8 |
| 139639 | CCATGTGAAGACAGCAGAAG | AGG | 8 |
| 139672 | TATAAGAATTCAAATACCTT | AGG | 8 |
| 139732 | AATGGTGTAATGGTTACCTT | TGG | 8 |
| 139752 | CATTTTCTCAGCAGTTGTCT | GGG | 8 |
| 139778 | CATTTGTGAAGATCATTTCT | TGG | 8 |
| 139792 | CTTGCAGTGAAGTGTTGCTG | GGG | 8 |
| 139832 | AAAGGCCACTGTGCTCCTAT | AGG | 8 |
| 139872 | AATGGGTCTACATTAGCACA | TGG | 8 |

FIGURE 19Z

| | | | |
|---|---|---|---|
| 139888 | GAAAGGAGCCCAGCTTGAGG | GGG | 8 |
| 139907 | AACTTTATGTACTGTTTGAT | AGG | 8 |
| 139994 | AATATAGCAGAAAGAGACAA | AGG | 8 |
| 140064 | GATATTTATTAAGGCCAAAC | TGG | 8 |
| 140071 | CATAAATGGATAGATATTAG | GGG | 8 |
| 140113 | GCTAGATATTGCACATGGGA | TGG | 8 |
| 140128 | GTAAGTACAGAACCATTGAG | GGG | 8 |
| 140129 | TGTAAGTACAGAACCATTGA | GGG | 8 |
| 140157 | ACACTGGAAAAGGAGGATAT | GGG | 8 |
| 140158 | AACACTGGAAAAGGAGGATA | TGG | 8 |
| 140724 | TAAGGAATAAGTGTTAGAAT | AGG | 8 |
| 140796 | CAAGGAATAAAAGTGGGGTC | TGG | 8 |
| 140859 | CAGGCTCTAAAAGCTGGAAA | AGG | 8 |
| 140870 | TGCCTGCATTTCTTGGCTCT | TGG | 8 |
| 140874 | GGCATTGAAGATGAAGGACA | GGG | 8 |
| 140899 | TCACCTCCTTCTCTCTTAGG | AGG | 8 |
| 140914 | CTTGACACGGAGAGATAGCC | TGG | 8 |
| 140961 | TACTGACATACTTCTTCGGG | TGG | 8 |
| 140993 | GGCAGACATGGTTTAACCAA | AGG | 8 |
| 141003 | AAGGCCTCCGGAAGTGGGAA | AGG | 8 |
| 141005 | AGTGGGAAAGGTGTATTGTT | GGG | 8 |
| 141015 | CCAAAAGACCATTTGAATTG | AGG | 8 |
| 141118 | CTTCTATTGTTACCATGGAG | AGG | 8 |

FIGURE 19AA

| | | | |
|---|---|---|---|
| 141131 | AGTAAAGGAGGTGGTGCAGA | GGG | 8 |
| 141134 | AGGAGGTGGTGCAGAGGGAG | AGG | 8 |
| 141135 | GGAGGTGGTGCAGAGGGAGA | GGG | 8 |
| 141150 | AAAACAACAGGAACACACAG | TGG | 8 |
| 141177 | TTTTCTGTTTTAGGATTGAG | GGG | 8 |
| 141178 | CTTTTCTGTTTTAGGATTGA | GGG | 8 |
| 141196 | CAGGTAAATGACCTTCAGAA | TGG | 8 |
| 141197 | TCCATCTACTGCCATTCTGA | AGG | 8 |
| 141317 | TACAAGTGAAGTCTATGGCA | TGG | 8 |
| 141453 | TACATCTCCCTGGCTTGTAT | GGG | 8 |
| 141465 | TCTTTGTATATATTGCAAAG | AGG | 8 |
| 141470 | TACAAAGAAATTTTTAGTTG | TGG | 8 |
| 141508 | ATCAGAAAGGCCAGTCTCCT | GGG | 8 |
| 141545 | TTCCTCATCTCTAGCTTGCT | AGG | 8 |
| 141571 | GTTGTCTGATGCCTTCTCTA | AGG | 8 |
| 141572 | GATGCAGTTAACCTTAGAGA | AGG | 8 |
| 141588 | CCGTATAAAAGGTTCAATCA | AGG | 8 |
| 141601 | AACACCTGAGAGTGAGGGTA | TGG | 8 |
| 141632 | TTAAAATAACCTCCACTATA | AGG | 8 |
| 141711 | CAGTCTCGTATCTGAACCCC | AGG | 8 |
| 141724 | CATTGCCTCCCACCCTCTGG | GGG | 8 |
| 141725 | AGCTCAGATGAGCCCCCAGA | GGG | 8 |
| 141726 | CAGCTCAGATGAGCCCCCAG | AGG | 8 |

FIGURE 19BB

| 141755 | TCTGTGAAAATAGATACCCA | GGG | | 8 |
| --- | --- | --- | --- | --- |
| 141789 | TAGAATCTGGCACTTATCAA | TGG | | 8 |
| 141798 | TGAAAGGGAGAAACTCAGAG | AGG | | 8 |
| 141804 | GGCGTTTTTCTTGTTTTGAA | AGG | | 8 |
| 141825 | GGTAAGCATCATGAATTTTA | TGG | | 8 |
| 141922 | TCATTTCCAAAGGGGAATCT | AGG | | 8 |
| 141935 | AGCAGCACTCCTAGCAGCTG | GGG | | 8 |
| 141953 | AGCGGCCCAGACTAAGACAA | GGG | | 8 |
| 141996 | CTCCTGTTAAATGGCATCTT | CGG | | 8 |
| 142009 | GGGAGGGCAAGGAAGCTTTC | TGG | | 8 |
| 142015 | TTTCTGGAGCCGCTTTTATA | AGG | | 8 |
| 142026 | GGGGGGTGATTAGGTCATGC | GGG | | 8 |
| 142072 | GCTAAAGTTCGTTGCCTTCC | TGG | | 8 |
| 142080 | TCAAGTCATGCACTGGATGT | GGG | | 8 |
| 142083 | ATCCAGTGCATGACTTGACA | CGG | | 8 |
| 142089 | AGGAAACGAAGAAAGGGGAC | TGG | | 8 |
| 142091 | AGTGCTAGGAAACGAAGAAA | GGG | | 8 |
| 142096 | AATGACCCTTCAGAAGTGCT | AGG | | 8 |
| 142132 | GTTCTTGGGGTCAACGTGTA | GGG | | 8 |
| 142146 | TGCATGCTCACCTCAATCTC | AGG | | 8 |
| 142162 | TCTTTAAGTAAGTAAACCCT | AGG | | 8 |
| 142192 | TGCTCCTTTATCAAGTACTT | GGG | | 8 |
| 142213 | GGGTCAAACACACCTGTTTG | TGG | | 8 |

FIGURE 19CC

| | | | |
|---|---|---|---|
| 142214 | GAAAGTCAGTGGCCACAAAC | AGG | 8 |
| 142231 | GGAGGGCACCTTCTGTTGAG | AGG | 8 |
| 142249 | ATAGATTCAAATTTTTCAGT | TGG | 8 |
| 142271 | ATTTGTACCATCAATTGGAA | AGG | 8 |
| 142322 | GAGGTTGGCATAACCATCAA | AGG | 8 |
| 142374 | TTAAAGCTTCTCTATATTTC | AGG | 8 |
| 142424 | TAAAATCTGGAAAGAGAATG | TGG | 8 |
| 142467 | TCAGACAGTTGCTCTAGAGA | AGG | 8 |
| 142462 | TTCTCTAGAGCAACTGTCTG | AGG | 8 |
| 142473 | AGGAATGGCTGCTTGGACCC | TGG | 8 |
| 142480 | GGACCCTGGTAGGTACATCA | TGG | 8 |
| 142483 | GGTAGGTACATCATGGTGAG | AGG | 8 |
| 142485 | TAATTTGTGAAGTTGTTACC | AGG | 8 |
| 142642 | TTCTGGACATGATTTCACAG | GGG | 8 |
| 142643 | ATTCTGGACATGATTTCACA | GGG | 8 |
| 142788 | AGGGCAATATCTACAAGTTT | GGG | 8 |
| 142792 | ATCTACAAGTTTGGGCCATG | GGG | 8 |
| 142820 | CAAGAAAGGCAACATTGGTA | AGG | 8 |
| 142830 | TTGATTATCATTGCTAGAAC | TGG | 8 |
| 142893 | GTGCATTATTAAGAGTATCT | TGG | 8 |
| 142904 | TTAGCTAAGAAGGAAAGAAA | GGG | 8 |
| 142926 | ATTGAGTGTTTTAACTGAAT | AGG | 8 |
| 142956 | TGGGGCTGCCAGAAAAGCAC | TGG | 8 |

FIGURE 19DD

| | | | | |
|---|---|---|---|---|
| 142964 | CAAACAGGAGCTGACACAGC | TGG | | 8 |
| 142982 | AGTACAGACATAGTGCCTGG | AGG | | 8 |
| 143124 | TGACAGCATTCTCACTACAG | TGG | | 8 |
| 143364 | CTGAGGTGACATGATCTCTT | GGG | | 8 |
| 143406 | CCAGGATGGAGGATCCCTTG | AGG | | 8 |
| 143455 | AAATCAAACTTGAGTAAGTG | TGG | | 8 |
| 143465 | TTTATGTAGAATTTCTCAGA | GGG | | 8 |
| 143531 | CATAGATTAACTTGATATGG | GGG | | 8 |
| 143626 | AACAAAAATTAAAAAGGGAT | AGG | | 8 |
| 143692 | GAGACACTAGAGTAATAATT | TGG | | 8 |
| 143724 | TAACATTACCCTAACATTAA | AGG | | 8 |
| 143947 | GTTGAAGATAATAGTGGATT | TGG | | 8 |
| 143964 | CCAGAGACATGTACATTTGT | TGG | | 8 |
| 144002 | GCAAACATGGTTTATTTCCA | TGG | | 8 |
| 144016 | GATGTGTAAGAAGTTGAGGG | GGG | | 8 |
| 144035 | TCCCAAGAGGTCTGGGGGTC | TGG | | 8 |
| 144057 | TGTAATAGCCACTTTCTGCT | GGG | | 8 |
| 144068 | ATGTGTGGGTAAAGTGGCAT | TGG | | 8 |
| 144069 | GGGACAATGTGTGGGTAAAG | TGG | | 8 |
| 144116 | CACACATTGCACTGTTACCT | GGG | | 8 |
| 144134 | CCAATCTGGAAAGGTCTTAC | TGG | | 8 |
| 144131 | CCAGTAAGACCTTTCCAGAT | TGG | | 8 |
| 144136 | ATCTGGAAAGGTCTTACTGG | AGG | | 8 |

FIGURE 19EE

| | | | |
|---|---|---|---|
| 144141 | TATTGAATAAAGAATTGAGT | TGG | 8 |
| 144183 | CAGGAGGGAGAAAGGTGGAG | GGG | 8 |
| 144199 | AGGAGGAAATGGAAGAGGGA | TGG | 8 |
| 144209 | AAGAGGACAAAAGAGGAGTG | AGG | 8 |
| 144212 | AATATTAAAGAGGACAAAAG | AGG | 8 |
| 144215 | ACAAGAAAGGAATATTAAAG | AGG | 8 |
| 144239 | AGGAAGAGAGGAAGGAAAGC | AGG | 8 |
| 144268 | AGGAAGGAGAGAACAAAGAA | GGG | 8 |
| 144278 | TAAATCTGACCCTTAAGGAA | AGG | 8 |
| 144357 | AATCAAGCAATACATACTAA | AGG | 8 |
| 144372 | CAAAGTCTAAAGCTAGTGAA | AGG | 8 |
| 144379 | ATGTCCTTATACCCCTTCTG | TGG | 8 |
| 144380 | TGAAATATTTGCCACAGAAG | GGG | 8 |
| 144414 | AATAAATGTGGATAGCTTGA | TGG | 8 |
| 144478 | CTGGGACGCATGTGGCTCAC | AGG | 8 |
| 144591 | AATCATTCTCTGATTAAATC | AGG | 8 |
| 144603 | TCCAGAGAGCTCTAATTGAT | AGG | 8 |
| 144632 | GAGGTTGAATAGAGAGGACT | GGG | 8 |
| 144638 | TGATGAGGAAGAAATTGATG | AGG | 8 |
| 144678 | CCAGGCATTAAAGAATGAGT | TGG | 8 |
| 144709 | TTGTGTGGGTGATGCTGTTG | GGG | 8 |
| 144711 | TATTGTGTGGGTGATGCTGT | TGG | 8 |
| 144712 | CAACTTCTCTGATATTGTGT | GGG | 8 |

FIGURE 19FF

| | | | | |
|---|---|---|---|---|
| 144713 | TCAACTTCTCTGATATTGTG | TGG | | 8 |
| 144721 | GTTGAAAACTATGAGGTTTA | AGG | | 8 |
| 144729 | AGATGTGAACTCAGGCAGTT | TGG | | 8 |
| 144732 | CAATGATGAGATGTGAACTC | AGG | | 8 |
| 144747 | TTACTGTGAGGTAGATAGAG | AGG | | 8 |
| 144790 | AGTGGCAGCTCAATAGAAGT | TGG | | 8 |
| 144814 | TAAGAAGGATAAGTAAGTAT | GGG | | 8 |
| 144860 | CCTATTCAGCAAGCAAGAGA | AGG | | 8 |
| 144853 | CTTCTCTTGCTTGCTGAATA | GGG | | 8 |
| 144979 | TTAAAGACGATCTCTGTGAG | GGG | | 8 |
| 145002 | GTTTGTGAGTCCAGCATTTA | GGG | | 8 |
| 145010 | AAGTCCACACTTCCTTGTGA | CGG | | 8 |
| 145063 | GTCATCAGGATTAAGTTGGT | TGG | | 8 |
| 145064 | GTTTGTCATCAGGATTAAGT | TGG | | 8 |
| 145083 | AGCTAGATAAACTTGGGCTC | AGG | | 8 |
| 145095 | TACTCAAGGTCACACAGCTT | GGG | | 8 |
| 145157 | GCAAGTAATAACACAAGCTT | AGG | | 8 |
| 145227 | AAGTGAGGCAGACAGAGTAA | GGG | | 8 |
| 145362 | GCCTAAGAACTGGTGGGAAA | TGG | | 8 |
| 145423 | GGAAGATGGCATTTCTAGTT | TGG | | 8 |
| 145495 | AAAGTTTTCAGACCTTGCCA | GGG | | 8 |
| 145585 | TTCTCTGCCCTAGGAACTCT | GGG | | 8 |
| 145587 | CCCTAGGAACTCTGGGACCT | TGG | | 8 |

FIGURE 19GG

| | | | | |
|---|---|---|---|---|
| 145581 | CCAAGGTCCCAGAGTTCCTA | GGG | | 8 |
| 145671 | GTCAGTCAAAAGTCCGTGTG | TGG | | 8 |
| 145700 | AGAGGTGAGTGGTGAGGGGA | AGG | | 8 |
| 145716 | AATTATTGGACTATGTAGTT | TGG | | 8 |
| 145729 | TCTCAACAGGAGACTCACAC | TGG | | 8 |
| 145786 | ATTGAAAGGCAGTAACAGTG | AGG | | 8 |
| 145808 | AGCATTTTGTGTCACAGTCC | AGG | | 8 |
| 145812 | CAGTCCAGGAGAAGAAATCA | TGG | | 8 |
| 145850 | ACCAGGCTGACTGGCAAATG | TGG | | 8 |
| 145860 | TAGATACACAAGGTATACTG | AGG | | 8 |
| 145930 | AGAAGGAAAGAAGAAAGTCA | GGG | | 8 |
| 145969 | CAAGGCAAGACAAGGCAGGA | AGG | | 8 |
| 145978 | AGGCAGGAAGGAAGGAAGTC | AGG | | 8 |
| 146006 | TCTTTTTGAGTCTCAGGCCC | TGG | | 8 |
| 146016 | TGATGACTAAATATGCCATT | GGG | | 8 |
| 146027 | ATATTCAGAGGATGATGGAG | AGG | | 8 |
| 146047 | GACCAGAAATACTGGCCTGA | CGG | | 8 |
| 146085 | CTTGCATCTTGCACATGTCC | TGG | | 8 |
| 146126 | CTAGAACACAAAACATGCCT | AGG | | 8 |
| 146155 | ATGTATGTGTGTGGGGTTGG | GGG | | 8 |
| 146156 | AATGTATGTGTGTGGGGTTG | GGG | | 8 |
| 146157 | AAATGTATGTGTGTGGGGTT | GGG | | 8 |
| 146178 | TAGCTCTGAATCAGAAAGCA | GGG | | 8 |

FIGURE 19HH

| | | | |
|---|---|---|---|
| 146226 | AAAGTAATGTTCACTGACAT | TGG | 8 |
| 146248 | TGAAAACAGTACCAATCTAA | TGG | 8 |
| 146249 | GTAACACAATTCCATTAGAT | TGG | 8 |
| 146262 | CTGACTGTAAGTACACTATG | TGG | 8 |
| 146274 | CCATACGAATGTAGAACATG | AGG | 8 |
| 146327 | GAGAAAATGAGATTTTTGTC | TGG | 8 |
| 146371 | CAAAATCTTGCACCACTATT | AGG | 8 |
| 146380 | AGGATTTTGAAAGTGTCTAG | AGG | 8 |
| 146584 | ATCCATAATCTAGAACGAAC | GGG | 8 |
| 146590 | TAGAATTTTCAATGATGTTC | TGG | 8 |
| 146607 | TCCCTAAGGAGCATGGGAAA | TGG | 8 |
| 146611 | AGGATTTCCGCCAGCTGGAG | GGG | 8 |
| 146621 | TTAAGATTAAATAGGGTACA | CGG | 8 |
| 146669 | TCTAACCACCTCAGAGACTA | AGG | 8 |
| 146670 | CTAACCACCTCAGAGACTAA | GGG | 8 |
| 146701 | GGTTCCTCCAGTAACAGATT | TGG | 8 |
| 146779 | TTTTGTTAATTAAAAGGTGT | TGG | 8 |
| 146798 | GAAAATTTAATTGGTTTCAG | GGG | 8 |
| 146859 | CCTGTTGACATGGAATGATA | AGG | 8 |
| 146885 | ATTCTCCAATGTTGCTTACA | TGG | 8 |
| 146982 | AAGAATCACTGAGTAAATGA | TGG | 8 |
| 146998 | CATCTACCCTGAAGATGGTT | TGG | 8 |
| 147019 | AGTGGTTAAGCACATTGTCT | TGG | 8 |

FIGURE 19II

| | | | |
|---|---|---|---|
| 147085 | CATATAATGTTAGTTATAGA | AGG | 8 |
| 147106 | ATTCTGATCCTACAATGCAC | AGG | 8 |
| 147121 | TTTTGGTTGTACATCTAGGA | GGG | 8 |
| 147126 | GTAATGTCAGGAGACATTTT | TGG | 8 |
| 147150 | GCAGCTATTTGAGAGGTGGG | TGG | 8 |
| 147151 | TAAGCAGCTATTTGAGAGGT | GGG | 8 |
| 147209 | GACAAAAGTGTAGATGCAAG | AGG | 8 |
| 147229 | GTTTCTCCACTCCTTGAATA | TGG | 8 |
| 147230 | ACTTGACCAATCCATATTCA | AGG | 8 |
| 147234 | ATTGGTCAAGTCACTTGTTT | CGG | 8 |
| 147262 | CTTGCCTGTAATTATTCATC | AGG | 8 |
| 147275 | ATATGTCTGGTATAACTTTT | TGG | 8 |
| 147299 | ATGATTCTTGATTCTGCTTG | GGG | 8 |
| 147338 | TCCAGCTGTGTTCTCTCTGC | TGG | 8 |
| 147402 | ACCACCCTTCATCAATAGCG | TGG | 8 |
| 147412 | TCTAGCTGGTTATACTCAAA | TGG | 8 |
| 147460 | GTCTAAATCTCTTATTTGTT | TGG | 8 |
| 147477 | AAGATCCTCTACCATGTGTC | AGG | 8 |
| 147478 | GCTTGTGAGGGCCTGACACA | TGG | 8 |
| 147480 | CTGGTGGATGAGGCTTGTGA | GGG | 8 |
| 147484 | ATCATCTCCTCTGGTGGATG | AGG | 8 |
| 147620 | TACTCAACATCGTCAATCAT | CGG | 8 |
| 147621 | ACTCAACATCGTCAATCATC | GGG | 8 |

FIGURE 19JJ

| | | | |
|---|---|---|---|
| 147622 | CTCAACATCGTCAATCATCG | GGG | 8 |
| 147668 | CAATCCCATTTCTGGGTGTA | CGG | 8 |
| 147666 | CTAACCGTACACCCAGAAAT | GGG | 8 |
| 147675 | GGTTAGTCCCCAACTTACTA | AGG | 8 |
| 147699 | ATACTCTCTTCTGACATATT | GGG | 8 |
| 147723 | GCAATGATGTTTGGTAGCTT | AGG | 8 |
| 147732 | GATGCTCATTGATTTACACT | GGG | 8 |
| 147744 | TTGCACACTCATATTAACTG | CGG | 8 |
| 147766 | TCCTTTCCTATGCTACAACA | TGG | 8 |
| 147767 | CCTTTCCTATGCTACAACAT | GGG | 8 |
| 147800 | ATTGCCAGTGCTGGGGTACA | GGG | 8 |
| 147803 | TGCTGGGGTACAGGGAGCAA | TGG | 8 |
| 148020 | TAAAAGGGAATTCATAGACC | AGG | 8 |
| 148051 | ATTGCAATGAGGATGCAAGT | AGG | 8 |
| 148074 | GGGTGCATCGACTCCAGAAG | AGG | 8 |
| 148123 | TGTGACAGGGACACTGGAGC | TGG | 8 |
| 148127 | AGGCTTCAGCCCATGTGACA | GGG | 8 |
| 148138 | CCTCAGTAGCAACTGCAGTG | TGG | 8 |
| 148146 | GGAAGTGAAGGAGGCAGTAT | TGG | 8 |
| 148150 | TGCTATTTATAAGGAAGTGA | AGG | 8 |
| 148171 | CATCTCTGACACCGTATCTC | TGG | 8 |
| 148172 | ACGTAAATAGACCAGAGATA | CGG | 8 |
| 148213 | ATCAGGCTGGCCTTGAACTC | CGG | 8 |

FIGURE 19KK

| | | | | |
|---|---|---|---|---|
| 148313 | TTCCAAGGTCATTATGAAGA | CGG | | 8 |
| 148356 | TACAAAAGAGATCAAAATCA | AGG | | 8 |
| 148372 | AGAATTTGAGATGGTTTGGC | AGG | | 8 |
| 148374 | AAAAAGAATTTGAGATGGTT | TGG | | 8 |
| 148382 | TAAATAAAACATGGTTTCAG | TGG | | 8 |
| 148411 | CTTCAGAAACCATTTACTGT | GGG | | 8 |
| 148413 | ACTTCAGAAACCATTTACTG | TGG | | 8 |
| 148417 | TCTTTCTGAATAAACAGAGT | TGG | | 8 |
| 148437 | AGGGGAAATCCCATCAGATC | AGG | | 8 |
| 148548 | AAGATGACGTGAGTCTCTTA | TGG | | 8 |
| 148558 | TCACCAGTCTAAAGATAGAG | TGG | | 8 |
| 148734 | CCACAGAAAATATATACATT | AGG | | 8 |
| 148773 | GACGTAAAAGTGGAATTGAA | GGG | | 8 |
| 148774 | AAGTGGAATTGAAGGGCATA | TGG | | 8 |
| 148789 | AATCTTCCCCTATTGACAAT | GGG | | 8 |
| 148792 | CTATTGACAATGGGGGCCTG | TGG | | 8 |
| 148867 | TCAAATGAGGACTAGATCCC | AGG | | 8 |
| 148922 | TTTAGCTATATCCAGCACAC | AGG | | 8 |
| 148923 | GAAGTTCTCAACCTGTGTGC | TGG | | 8 |
| 148984 | TGAAGATAGATATTCATGTC | AGG | | 8 |
| 149000 | GTGATGATACTGGTAGGATA | GGG | | 8 |
| 149001 | TGATACTGGTAGGATAGGGA | TGG | | 8 |
| 149006 | TAGGGATGGGGGCAAAACAA | AGG | | 8 |

FIGURE 19LL

| | | | | |
|---|---|---|---|---|
| 149011 | AGTAAAGTGGAAGAGAATTC | AGG | | 8 |
| 149058 | GTTTGGAAAGAAGACTGTAT | GGG | | 8 |
| 149064 | TGTAAGACTGAAATCAACAT | AGG | | 8 |
| 149113 | GTACTGGGAAACTACTGGGC | AGG | | 8 |
| 149121 | CCAGTACATGAAATTAGTAC | TGG | | 8 |
| 149123 | GTACATGAAATTAGTACTGG | AGG | | 8 |
| 149128 | TTGGGTGGTTCTAACATGTA | AGG | | 8 |
| 149221 | CAGTGAGGAGTTGAGAGCAG | TGG | | 8 |
| 149248 | TGAGCACTGGAGCAGCATCT | AGG | | 8 |
| 149310 | TAGATGCTGGACAAGAGCTC | AGG | | 8 |
| 149409 | GGGTGGGGTGGGGCCATGGG | TGG | | 8 |
| 149440 | TGAGGGTGGGGTTTTCGCTG | GGG | | 8 |
| 149470 | AGGTGCTCCTCAACGTACAA | TGG | | 8 |
| 149487 | GACCATGTTGAAGGTAGGCT | AGG | | 8 |
| 149522 | GATTTACAATGGTTCGGCTT | AGG | | 8 |
| 149538 | CAATTATCTCCTTTTGTCAA | GGG | | 8 |
| 149574 | TTTTCAAGATATAGAATTGT | CGG | | 8 |
| 149588 | GACTGGTTTAGACTAAAACT | AGG | | 8 |
| 149600 | TAGTATACGTCTAAAATCTT | GGG | | 8 |
| 149624 | CAATAATAGTATATTACTAT | TGG | | 8 |
| 149632 | ATCATCCCGATCACAGCCCC | AGG | | 8 |
| 149649 | CAAACAGCTAAGCCATTCCC | TGG | | 8 |
| 149706 | ATCATAATACAATATTGTCA | AGG | | 8 |

FIGURE 19MM

| | | | | |
|---|---|---|---|---|
| 149742 | AAGGATCAGAAACGAAATTT | AGG | | 8 |
| 149745 | ATTTAGTCATTCACATTGGG | AGG | | 8 |
| 149787 | AGAAAGCAGAATTTCAGAGT | GGG | | 8 |
| 149823 | TAATCTCATCCTCTTGGTTC | AGG | | 8 |
| 149857 | GATGACTGCCAGCAACAAAT | GGG | | 8 |
| 149858 | AGATGACTGCCAGCAACAAA | TGG | | 8 |
| 149863 | CTGGCAGTCATCTTGGAACC | TGG | | 8 |
| 149868 | CTCCTCACTAGTTGCCCTCC | AGG | | 8 |
| 149893 | AGCTCTGCTTGTACTTCATC | TGG | | 8 |
| 149900 | TCACATAACTGGAAGTTCAG | AGG | | 8 |
| 149950 | GGAGGACTAAGTAGGAAAAA | AGG | | 8 |
| 149992 | TGGTACCTACTAGTCTATCT | AGG | | 8 |
| 150154 | TGGCTTAATGCCCTTCCTGG | GGG | | 8 |
| 150156 | CACTCAACCTGCCCCCAGGA | AGG | | 8 |
| 150400 | AAGAATTGGAAGTGACCAAC | TGG | | 8 |
| 150415 | AGCTGAAGACAGGCGTGATG | TGG | | 8 |
| 150444 | GTACCATAGAAATTTTAAAA | GGG | | 8 |
| 150486 | GCTTGAGTGACAACTCCATG | TGG | | 8 |
| 150523 | CAGATATTCAGCAAACACAG | GGG | | 8 |
| 150598 | GAGTGAGAGGGTTGCAAGTT | GGG | | 8 |
| 150611 | TAGCCCTTAGCTCATTATGA | AGG | | 8 |
| 150607 | AAACCTTCATAATGAGCTAA | GGG | | 8 |
| 150608 | CAAACCTTCATAATGAGCTA | AGG | | 8 |

FIGURE 19NN

| | | | |
|---|---|---|---|
| 150616 | GGGAGCTAAGGAAATTTAGA | GGG | 8 |
| 150655 | GGAAACAAGGAGTACCAAAG | GGG | 8 |
| 150657 | CTGGAAACAAGGAGTACCAA | AGG | 8 |
| 150670 | GAGAAGGAACCCTTGAGCTG | GGG | 8 |
| 150691 | TACCTGGGAATGAATGAGGA | AGG | 8 |
| 150700 | TCATTCATTCCCAGGTAATG | GGG | 8 |
| 150725 | ATTCACCATTCTGCATGGCT | GGG | 8 |
| 150928 | GCCATGATAGCAGCTGGGAG | GGG | 8 |
| 151347 | CTTTGACCAATGATATGGTT | TGG | 8 |
| 151361 | TGGGGATCTAATGTACATTA | TGG | 8 |
| 151459 | CTGAAAAGTGAGTAGGTATG | AGG | 8 |
| 151490 | AGTAAGTAGTTCACAGTATC | TGG | 8 |
| 151492 | AGTTCACAGTATCTGGTATA | AGG | 8 |
| 151525 | TAGGAGAGAAGAAATGAATG | AGG | 8 |
| 151569 | AGAGATGATGAGATTGTACA | GGG | 8 |
| 151570 | GAGATGATGAGATTGTACAG | GGG | 8 |
| 151597 | CCAGCAGGGGTGAGGTGGGA | AGG | 8 |
| 151602 | CTATCCAGTAACAAAATCTT | GGG | 8 |
| 151608 | TTTGTTACTGGATAGCTAAG | TGG | 8 |
| 151618 | CTGAAGAAAGGAATATATCA | GGG | 8 |
| 151621 | GAAAGGAATATATCAGGGGA | AGG | 8 |
| 151639 | ATATGCAGTATGGAATACAG | AGG | 8 |
| 151659 | CTTTGGGTCCCCTGAAAACA | GGG | 8 |

FIGURE 19OO

| | | | |
|---|---|---|---|
| 151662 | GGTCCCCTGAAAACAGGGCC | TGG | 8 |
| 151672 | TTGGGTACAGATAGCTCATT | TGG | 8 |
| 151676 | TCATTTGGAAGCTGATCCCT | AGG | 8 |
| 151702 | GGTAATGCTTATGGACCATG | GGG | 8 |
| 151703 | CTGTCAAAATACAGTCCCCA | TGG | 8 |
| 151708 | GGGAATTCTCTGTGATTCTC | AGG | 8 |
| 151718 | GAATTCCCCTTGCCCCGGA | AGG | 8 |
| 151723 | TTTTTAACCACTATTCCTTC | CGG | 8 |
| 151730 | CCATGGGCTCCCATCTCCAT | TGG | 8 |
| 151727 | CCAATGGAGATGGGAGCCCA | TGG | 8 |
| 151746 | GAGAAAGCTCACAAAATCTG | TGG | 8 |
| 151764 | TTAGATAGAAAGTAGAAAAA | TGG | 8 |
| 151768 | TGGGAGCCATTCCCTTGACA | TGG | 8 |
| 151770 | CTGACAGCATCCCATGTCAA | GGG | 8 |
| 151776 | CATGGGATGCTGTCAGCTAA | AGG | 8 |
| 151791 | TGCAGCTGCAACTGCAGTGC | AGG | 8 |
| 151793 | GCAACTGCAGTGCAGGAAAA | TGG | 8 |
| 151799 | GCGTGTGACTCCAGGCACCA | GGG | 8 |
| 151802 | ACAATTGTAACAGATTCCCC | TGG | 8 |
| 151836 | GATGGAGGCGATTGTGCTGT | GGG | 8 |
| 151837 | AGATGGAGGCGATTGTGCTG | TGG | 8 |
| 152012 | CTTCTCCAGCCTAGATGTTT | AGG | 8 |
| 152060 | TGGTAGAAATTACTAAACTA | TGG | 8 |

FIGURE 19PP

| | | | |
|---|---|---|---|
| 152069 | GTTTATCAAGCCAAATGCCT | GGG | 8 |
| 152106 | GGAGGCTATTCCAGTGGTTC | AGG | 8 |
| 152131 | ACTAGTGACATGAGCATATT | TGG | 8 |
| 152150 | GAGGACATTCCAGATGATGC | TGG | 8 |
| 152181 | CAAGAGAAACAAGTAACAGT | TGG | 8 |
| 152184 | TGTTACTTGTTTCTCTTGCC | TGG | 8 |
| 152197 | TCTCCCTACTTGTTTGCCT | AGG | 8 |
| 152192 | TGTACCTAGGCAAACAAGTA | GGG | 8 |
| 152193 | GTGTACCTAGGCAAACAAGT | AGG | 8 |
| 152280 | AGTTAAGTCAAATAGTGTAC | TGG | 8 |
| 152281 | TCAAATAGTGTACTGGAAAA | TGG | 8 |
| 152287 | GCAGGAGATGTCACCATCAG | GGG | 8 |
| 152387 | ACACTCTTAAGAGTTGTACC | AGG | 8 |
| 152396 | ACCACTTACTTAGCATAGAA | TGG | 8 |
| 152414 | TCTTCTTAAGGCTTCCTCCA | GGG | 8 |
| 152422 | GAGGAAGCCTTAAGAAGATT | AGG | 8 |
| 152492 | ACTGTTTCAGCGGGAGGTAT | AGG | 8 |
| 152565 | ACACTCAAGGAATAAATTGG | AGG | 8 |
| 152590 | TCTCAATCCACTTGCATCCA | TGG | 8 |
| 152595 | ATCCATGGCCTTGCTCACAC | TGG | 8 |
| 152596 | TCCATGGCCTTGCTCACACT | GGG | 8 |
| 152611 | AGCCAAGAAGCATGCTTAAG | TGG | 8 |
| 152665 | GACTGGTTGAAATTGCAGAT | GGG | 8 |

FIGURE 19QQ

| 152677 | AGGAAACTCTACCCTTTTGA | CGG | | 8 |
| --- | --- | --- | --- | --- |
| 152683 | CTACCCTTTTGACGGCCGAA | GGG | | 8 |
| 152678 | GTCCCCTTCGGCCGTCAAAA | GGG | | 8 |
| 152731 | CAGCACTTCATTTAATCTTA | AGG | | 8 |
| 152827 | CATGCAAAACGGAAAAGAAA | GGG | | 8 |
| 152872 | ACTTAGTAGCTGGGTGTTTT | TGG | | 8 |
| 152867 | AAAAACACCCAGCTACTAAG | TGG | | 8 |
| 152896 | AGAATACTTGGCAAAATGCC | TGG | | 8 |
| 152906 | ACATACCTAATATTTATCTT | AGG | | 8 |
| 152943 | TTCATGTTTAACTCTCCTGG | AGG | | 8 |
| 152945 | CACTTCATGTTTAACTCTCC | TGG | | 8 |
| 152962 | CCATGCATTCAAATGTTCCT | TGG | | 8 |
| 152971 | CGCAAATCTCTATGATTCTG | GGG | | 8 |
| 152973 | ACGCAAATCTCTATGATTCT | GGG | | 8 |
| 152974 | GACGCAAATCTCTATGATTC | TGG | | 8 |
| 153076 | CTTGTCATACTGAAGTGAAT | GGG | | 8 |
| 153098 | AATGAAGGGACATTGGAGAT | TGG | | 8 |
| 153182 | AAAATACTGAAGATGAGAGA | AGG | | 8 |
| 153206 | GAATGAGGGTTTAAGGAGAT | AGG | | 8 |
| 153251 | GAAATTAAACTCAGGAGATG | TGG | | 8 |
| 153285 | GAATTAAAGCTAGACACACC | TGG | | 8 |
| 153298 | TTTATGATGTGACAGAGTCA | TGG | | 8 |
| 153333 | CTGTTTTGTTGCCAGACCAT | GGG | | 8 |

FIGURE 19RR

| | | | |
|---|---|---|---|
| 153335 | TCAGATGAGTCCCCATGGTC | TGG | 8 |
| 153434 | GCCTTCCATTTTGAGCGGTA | GGG | 8 |
| 153518 | AAGGGAACTTCATCACAAAA | TGG | 8 |
| 153541 | TAACCAGTGAGCATTGTTGA | AGG | 8 |
| 153539 | GGTCCTTCAACAATGCTCAC | TGG | 8 |
| 153552 | TGAAGGCAGTAGGGGGTCCC | TGG | 8 |
| 153553 | CTTTCCATGAAGGCAGTAGG | GGG | 8 |
| 153565 | CACTTCTCACACTCATCAGA | AGG | 8 |
| 153572 | GATGAGTGTGAGAAGTGCTG | GGG | 8 |
| 153577 | GTGCTGGGGCCTCACCAGCC | AGG | 8 |
| 153579 | TGCTGGGGCCTCACCAGCCA | GGG | 8 |
| 153576 | ACAGAAAGCCCTGGCTGGTG | AGG | 8 |
| 153580 | TGACAACAGAAAGCCCTGGC | TGG | 8 |
| 153588 | AGATGTGTCACACTGTAGAA | AGG | 8 |
| 153615 | TCCAAGGCCTTGCAGTATCT | TGG | 8 |
| 153683 | ATAGAAACATGGCAGGGGAG | GGG | 8 |
| 153741 | TATTTAAAGTATTATTGAAA | TGG | 8 |
| 153855 | GAGCTAGTCAGTGACAGAGT | GGG | 8 |
| 153856 | AGAGCTAGTCAGTGACAGAG | TGG | 8 |
| 153882 | TTACTCAAAAGGTATAACTG | TGG | 8 |
| 153908 | GAGCTGATCCCAGAAAGCCA | TGG | 8 |
| 153926 | CTGTCAGTTGTATCTCAGCA | GGG | 8 |
| 153933 | GATATATGAGAATACTGAAG | AGG | 8 |

FIGURE 19SS

| | | | | |
|---|---|---|---|---|
| 153946 | CTTCCCATTTTGGCAGAATC | TGG | | 8 |
| 153953 | TGGGAAGAAAGCCTACACAT | CGG | | 8 |
| 153954 | TAGGCTTCCTTCCGATGTGT | AGG | | 8 |
| 153990 | TACCCAAGGGGAGAAGAAGG | TGG | | 8 |
| 153985 | TCCCACCTTCTTCTCCCCTT | GGG | | 8 |
| 154090 | AACCAATGGACAAAAGCTGG | GGG | | 8 |
| 154092 | TTAACCAATGGACAAAAGCT | GGG | | 8 |
| 154093 | CTTAACCAATGGACAAAAGC | TGG | | 8 |
| 154115 | CTTCCAGCCTGCTCTGCAAG | TGG | | 8 |
| 154136 | AAGGACTCAGGAAGACTCAC | AGG | | 8 |
| 154149 | TATAGGAAGGCTGAGTGCTA | AGG | | 8 |
| 154152 | TAGGAAGGCTGAGTGCTAAG | GGG | | 8 |
| 154159 | GGAAATGGGTAGCCCACTAA | GGG | | 8 |
| 154160 | AGATAGATTTGACCCTTAGT | GGG | | 8 |
| 154193 | AAGCAGAAAATATCTAGTAT | CGG | | 8 |
| 154370 | TTCTCAGGCCCAGCAGCTTG | TGG | | 8 |
| 154415 | GCAGAGCTGTTCAGTGTTCC | TGG | | 8 |
| 154423 | TCTGCAGGGCAAATACTGCC | TGG | | 8 |
| 154439 | AAGCTATAACATCCTCGGGG | TGG | | 8 |
| 154441 | GCTATAACATCCTCGGGGTG | GGG | | 8 |
| 154456 | CCAGTGCTGTGAATGCTAAA | GGG | | 8 |
| 154467 | CCCTTCTGCTGTGTGCAGCA | AGG | | 8 |
| 154487 | GGTAGTAGTTCTCAAAGCAT | AGG | | 8 |

FIGURE 19TT

| | | | |
|---|---|---|---|
| 154491 | TTCCTAGGTTATGCTGATGC | TGG | 8 |
| 154494 | TGCATCTCTGAAAAGTTCCT | AGG | 8 |
| 154502 | CAGAGATGCAAGTCTTGGCT | GGG | 8 |
| 154613 | GTTTCTGATTTACTAGCTCT | GGG | 8 |
| 154647 | AAATCACTACATTGGGGAAA | AGG | 8 |
| 154661 | ATGCCACATCGCATATCAAA | GGG | 8 |
| 154695 | TACAAGACCTTCTGATGCCT | AGG | 8 |
| 154722 | TGAAGCCTAATCTAGCCTAC | AGG | 8 |
| 154966 | ACAGCCACAAAACAAAACAC | AGG | 8 |
| 154996 | TTTAAAGATTAAGGAGCCTG | AGG | 8 |
| 155084 | GCCCTCAGCTCAAAGCTGTT | TGG | 8 |
| 155094 | CATTCCCAGACTCTCCATAC | TGG | 8 |
| 155102 | CCATACTGGCAGCAATGTGG | AGG | 8 |
| 155153 | AACAAGATGACGGAATATTA | AGG | 8 |
| 155155 | CTGAAGTAGGAACAAGATGA | CGG | 8 |
| 155170 | ATTTCTGGGAAAATTATTCC | AGG | 8 |
| 155176 | AATTTTCCCAGAAATACACC | AGG | 8 |
| 155173 | AGTGAGCCTGGTGTATTTCT | GGG | 8 |
| 155174 | AAGTGAGCCTGGTGTATTTC | TGG | 8 |
| 155203 | TTACAGAGAACAACTAAGCA | GGG | 8 |
| 155216 | GTGTGCACAGGATTCACCTG | GGG | 8 |
| 155225 | GATTGTGATTCAGTGGGTCT | AGG | 8 |
| 155232 | TGTTAGACACACAGAATCTG | AGG | 8 |

FIGURE 19UU

| 155274 | TGTTTATAAGAAAAATACAT | TGG | | 8 |
|---|---|---|---|---|
| 155282 | GGATTTCGGCGCCCTGGTTT | TGG | | 8 |
| 155283 | GTAGGAAGGCTCCAAAACCA | GGG | | 8 |
| 155285 | GGTAGGAAGGCTCCAAAACC | AGG | | 8 |
| 155314 | GTTTTCTGGCTGTCTCTGGT | AGG | | 8 |
| 155323 | ACACCAATAAATGATAACAT | AGG | | 8 |
| 155326 | CAAACTATGCATATGCGCTG | AGG | | 8 |
| 155397 | ATGATTGAAGCATTAAAGCA | TGG | | 8 |
| 155430 | TCTCATGGCAATGTTAATGC | TGG | | 8 |
| 155438 | CCTTCTATCAACAACTGAAG | AGG | | 8 |
| 155458 | TCCTCCCCCAAGTCAGCTTG | TGG | | 8 |
| 155463 | CAAGAAAAGAAAAATGGAT | TGG | | 8 |
| 155494 | GTGTGCATTGTTCCTGAAGA | GGG | | 8 |
| 155515 | CAACTTGGACAAGTTTTCTG | AGG | | 8 |
| 155524 | GGCTGGCTGCTGCCTGAGAG | TGG | | 8 |
| 155530 | CTCAGGCAGCAGCCAGCCCC | TGG | | 8 |
| 155533 | AGCAGCCAGCCCCTGGCCAA | TGG | | 8 |
| 155535 | GATCCAGCCAGCCATTGGCC | AGG | | 8 |
| 155549 | TGAATTGCAGGCAGTGGGCC | TGG | | 8 |
| 155550 | TGTCCTGAATTGCAGGCAGT | GGG | | 8 |
| 155551 | CTGTCCTGAATTGCAGGCAG | TGG | | 8 |
| 155555 | GCAGAGCTGTCCTGAATTGC | AGG | | 8 |
| 155603 | GGGATATGGGGAGTGTTCTC | TGG | | 8 |

FIGURE 19VV

| 155608 | TCAAAGTGTTGCATGACAAC | GGG | 8 |

MATERIALS AND METHODS FOR TREATMENT OF DUCHENNE MUSCULAR DYSTROPHY

TECHNICAL FIELD

The present application provides materials and methods for treating a patient with Duchenne Muscular Dystrophy (DMD), both ex vivo and in vivo. In addition, the present application provides materials and methods for editing a dystrophin gene in a cell by genome editing.

RELATED APPLICATIONS

This application claims the benefit of U.S. Provisional Application No. 62/247,484 filed Oct. 28, 2015 and U.S. Provisional Application No. 62/324,064 filed Apr. 18, 2016, both of which are incorporated herein in their entirety by reference.

INCORPORATION BY REFERENCE OF SEQUENCE LISTING

This application contains a Sequence Listing in computer readable form (filename: 160101PCT sequence listing_ST25: 286,928,896 bytes—ASCII text file; created Oct. 28, 2016), which is incorporated herein by reference in its entirety and forms part of the disclosure.

BACKGROUND

Duchenne Muscular Dystrophy (DMD) is a severe X-linked recessive neuromuscular disorder effecting approximately 1 in 4,000 live male births. Patients are generally diagnosed by the age of 4, and wheel chair bound by the age of 10. Most patients do not live past the age of 25 due to cardiac and/or respiratory failure. Existing treatments are palliative at best. The most common treatment for DMD is steroids, which are used to slow the loss of muscle strength. However, because most DMD patients start receiving steroids early in life, the treatment delays puberty and further contributes to the patient's diminished quality of life.

DMD is caused by mutations in the dystrophin gene (Chromosome X: 31,117,228-33,344,609 (Genome Reference Consortium—GRCh38/hg38)). With a genomic region of over 2.2 megabases in length, dystrophin is the second largest human gene. The dystrophin gene contains 79 exons that are processed into an 11,000 base pair mRNA that is translated into a 427 kDa protein. Functionally, dystrophin acts as a linker between the actin filaments and the extracellular matrix within muscle fibers. The N-terminus of dystrophin is an actin-binding domain, while the C-terminus interacts with a transmembrane scaffold that anchors the muscle fiber to the extracellular matrix. Upon muscle contraction, dystrophin provides structural support that allows the muscle tissue to withstand mechanical force. DMD is caused by a wide variety of mutations within the dystrophin gene that result in premature stop codons and therefore a truncated dystrophin protein. Truncated dystrophin proteins do not contain the C-terminus, and therefore cannot provide the structural support necessary to withstand the stress of muscle contraction. As a result, the muscle fibers pull themselves apart, which leads to muscle wasting.

Becker Muscular Dystrophy (BMD) is a less severe form of muscular dystrophy compared to DMD. While BMD is also caused by mutations within the dystrophin gene, BMD mutations maintain the dystrophin reading frame. BMD dystrophin proteins contain internal deletions, but also retain portions of both the N and C termini. Therefore, the BMD dystrophin protein is shorter than the wild type protein, but can still function as a linker between the actin filaments and the extracellular matrix. In fact, depending on the size of the internal deletion, BMD patients may have only minor symptoms. As a result, most research efforts have been focused on converting the severe DMD phenotype to a less severe BMD phenotype.

Genome engineering refers to the strategies and techniques for the targeted, specific modification of the genetic information (genome) of living organisms. Genome engineering is a very active field of research because of the wide range of possible applications, particularly in the areas of human health; the correction of a gene carrying a harmful mutation, for example, to explore the function of a gene. Early technologies developed to insert a gene into a living cell, such as transgenesis, were often limited by the random nature of the insertion of the new sequence into the genome. The new gene was usually positioned blindly, and may have inactivated or disturbed the functioning of other genes, or even caused severe unwanted effects. Furthermore, these technologies generally offered no degree of reproducibility, as there was no guarantee that the new sequence would be inserted at the same place in two different cells. More recent genome engineering strategies, such as ZFNs, TALENs, HEs and MegaTALs, enable a specific area of the DNA to be modified, thereby increasing the precision of the correction or insertion compared to early technologies, and offering some degree of reproducibility. Despite this, such recent genome engineering strategies have limitations.

Multiple studies suggest that genome engineering would be an attractive strategy for treating DMD. One of the earliest approaches involved engineering a mini-dystrophin gene that is less than 4 kb and can be packaged into an adeno-associated virus (AAV) vector. This is a replacement gene therapy that has been tested experimentally in mouse (Wang, B., J. Li, and X. Xiao, Proc Natl Acad Sci USA, 2000. 97(25): p. 13714-9) (Watchko, J., et al., Hum Gene Ther, 2002. 13(12): p. 1451-60) and dog models (Wang, Z., et al., Mol Ther, 2012. 20(8): p. 1501-7), and a phase I clinical trial suggested that there are problems associated with an immune response to the non-self synthetic epitopes (Mendell, J. R., et al., N Engl J Med, 2010. 363(15): p. 1429-37).

More recently, oligo-mediated exon skipping was used to restore the reading frame in the cells of DMD patients. In this strategy, short oligos block splicing signals found in pre-mRNA and facilitate skipping of a single exon. Skipping of a single exon allows the transcriptional machinery to bypass the premature stop codon and produce a protein with intact N and C termini. Phase I/II clinical trials have shown that weekly injections of anti-sense oligos induce exon skipping and dystrophin positive fibers (Cirak, S., et al., Lancet, 2011. 378(9791): p. 595-605). However, the major limitation of this type of treatment is that it requires repeat dosing over the lifetime of the patient because the drug targets the pre-mRNA rather than the genomic locus. Ongoing Phase II/III clinical trials are evaluating delivery of exon skipping oligos via AAV for sustained expression, as well as delivery of multiple anti-sense oligos for facilitating multi-exon skipping strategies.

Despite efforts from researchers and medical professionals worldwide who have been trying to address DMD, and despite the promise of genome engineering approaches, there still remains a critical need for developing safe and effective treatments for DMD, which is among the most prevalent and debilitating genetic disorders.

SUMMARY

The present disclosure presents an approach to address the genetic basis of DMD. By using genome engineering tools to create permanent changes to the genome that can restore the dystrophin reading frame and restore the dystrophin protein activity with as few as a single treatment, the resulting therapy can correct the underlying genetic defect causing the disease.

Provided herein are cellular, ex vivo and in vivo methods for creating permanent changes to the genome by deleting, inserting, or replacing (deleting and inserting) one or more exons or aberrant intronic splice acceptor or donor sites in the dystrophin gene by genome editing and restoring the dystrophin reading frame and restoring the dystrophin protein activity, which can be used to treat Duchenne Muscular Dystrophy (DMD). Also provided herein are components, kits and compositions for performing such methods. Also, provided are cells produced by such methods.

Provided herein is a method for editing a dystrophin gene in a human cell by genome editing, the method comprising the step of introducing into the human cell one or more deoxyribonucleic acid (DNA) endonucleases to effect one or more single-strand breaks (SSBs) or double-strand breaks (DSBs) within or near the dystrophin gene that results in a permanent deletion, insertion, or replacement of one or more exons or aberrant intronic splice acceptor or donor sites within or near the dystrophin gene and results in restoration of the dystrophin reading frame and restoration of the dystrophin protein activity. The human cell can be a muscle cell or muscle precursor cell.

Also provided herein is an ex vivo method for treating a patient (e.g., a human) with Duchenne Muscular Dystrophy (DMD), the method comprising the steps of: i) creating a DMD patient specific induced pluripotent stem cell (iPSC); ii) editing within or near a dystrophin gene of the iPSC; iii) differentiating the genome-edited iPSC into a Pax7+ muscle progenitor cell; and iv) implanting the Pax7+ muscle progenitor cell into the patient.

The step of creating a patient specific induced pluripotent stem cell (iPSC) can comprise: a) isolating a somatic cell from the patient; and b) introducing a set of pluripotency-associated genes into the somatic cell to induce the somatic cell to become a pluripotent stem cell. The somatic cell can be a fibroblast. The set of pluripotency-associated genes is one or more of the genes selected from the group consisting of OCT4, SOX2, KLF4, Lin28, NANOG and cMYC.

The step of editing within or near a dystrophin gene of the iPSC can comprise introducing into the iPSC one or more deoxyribonucleic acid (DNA) endonucleases to effect one or more single-strand breaks (SSBs) or double-strand breaks (DSBs) within or near the dystrophin gene that results in a permanent deletion, insertion, or replacement of one or more exons or aberrant intronic splice acceptor or donor sites within or near the dystrophin gene and results in restoration of the dystrophin reading frame and restoration of the dystrophin protein activity.

The step of differentiating the genome-edited iPSC into a Pax7+ muscle progenitor cell can comprise contacting the genome-edited iPSC with specific media formulations, including small molecule drugs; transgene overexpression; or serum withdrawal.

The step of implanting the Pax7+ muscle progenitor cell into the patient can comprise implanting the Pax7+ muscle progenitor cell into the patient by local injection into the desired muscle.

Also provided herein is an in vivo method for treating a patient (e.g., a human) with Duchenne Muscular Dystrophy (DMD), the method comprising the step of editing a dystrophin gene in a cell of the patient. The cell can be a muscle cell or muscle precursor cell.

The step of editing a dystrophin in a cell of the patient can comprise introducing into the cell of the patient one or more deoxyribonucleic acid (DNA) endonucleases to effect one or more single-strand breaks (SSBs) or double-strand breaks (DSBs) within or near the dystrophin gene that results in a permanent deletion, insertion, or replacement of one or more exons or aberrant intronic splice acceptor or donor sites within or near the dystrophin gene and results in restoration of the dystrophin reading frame and restoration of the dystrophin protein activity.

The one or more DNA endonucleases can be a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombinant of the naturally occurring molecule thereof, a codon-optimized thereof, modified version thereof, and combinations of any of the foregoing.

The method can comprise introducing into the cell one or more polynucleotides encoding the one or more DNA endonucleases. The method can comprise introducing into the cell one or more ribonucleic acids (RNAs) encoding the one or more DNA endonucleases. The one or more polynucleotides or one or more RNAs can be one or more modified polynucleotides or one or more modified RNAs. The one or more DNA endonuclease can be one or more proteins or polypeptides.

The method can further comprise introducing into the cell one or more guide ribonucleic acids (gRNAs). The one or more gRNAs are single-molecule guide RNA (sgRNAs). The one or more gRNAs or one or more sgRNAs is one or more modified gRNAs or one or more modified sgRNAs. The one or more DNA endonucleases can be pre-complexed with one or more gRNAs or one or more sgRNAs.

The method can further comprise introducing into the cell a polynucleotide donor template comprising at least a portion of the wild-type dystrophin gene or cDNA. The at least a portion of the wild-type dystrophin gene or cDNA can include at least a part of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA. The at least a portion of the wild-type dystrophin gene or cDNA can include exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA. The donor template can be a single or double stranded polynucleotide.

The method can further comprise introducing into the cell one or more guide ribonucleic acid (gRNAs). The one or more DNA endonucleases can be one or more Cas9 or Cpf1 endonucleases that effect a pair of single-strand breaks (SSBs) or double-strand breaks (DSBs), the first SSB or DSB break at a 5' locus and the second SSB or DSB break at a 3' locus, that results in a permanent deletion or replacement of one or more exons or aberrant intronic splice acceptor or donor sites between the 5' locus and the 3' locus within or near the dystrophin gene and results in restoration of the dystrophin reading frame and restoration of the dystrophin protein activity. One gRNA can create a pair of SSBs or DSBs. One gRNA can comprise a spacer sequence that is complementary to either the 5' locus, the 3' locus, or a segment between the 5' locus and 3' locus. A first gRNA can comprise a spacer sequence that is complementary to a segment of the 5' locus and the second gRNA can comprise a spacer sequence that is complementary to a segment of the 3' locus.

The one or more gRNAs can be one or more single-molecule guide RNAs (sgRNAs). The one or more gRNAs or one or more sgRNAs can be one or more modified gRNAs or one or more modified sgRNAs. The one or more DNA endonucleases can be pre-complexed with the one or more gRNAs or one or more sgRNAs.

There can be a deletion of the chromosomal DNA between the 5' locus and the 3' locus.

The deletion can be a single exon deletion. The single exon deletion can be a deletion of exon 2, exon 8, exon 43, exon 44, exon 45, exon 46, exon 50, exon 51, exon 52, or exon 53. The 5' locus can be proximal to a 5' boundary of a single exon selected from the group consisting of exon 2, exon 8, exon 43, exon 44, exon 45, exon 46, exon 50, exon 51, exon 52, and exon 53. The 3' locus can be proximal to a 3' boundary of a single exon selected from the group consisting of exon 2, exon 8, exon 43, exon 44, exon 45, exon 46, exon 50, exon 51, exon 52, and exon 53. The 5' locus can be proximal to a 5' boundary and the 3' locus can be proximal to the 3' boundary of a single exon selected from the group consisting of exon 2, exon 8, exon 43, exon 44, exon 45, exon 46, exon 50, exon 51, exon 52, and exon 53. Proximal to the boundary of the exon can include the surrounding splice donors and acceptors of the neighboring intron.

The deletion can be a multi-exon deletion. The multi-exon deletion can be a deletion of exons 45-53 or exons 45-55. The 5' locus can be proximal to a 5' boundary of multiple exons selected from the group consisting of exons 45-53 and exons 45-55. The 3' locus can be proximal to a 3' boundary of multiple exons selected from the group consisting of exons 45-53 and exons 45-55. The 5' locus can be proximal to a 5' boundary and a 3' locus can be proximal to the 3' boundary of multiple exons selected from the group consisting of exons 45-53 and exons 45-55. Proximal to the boundary of the exon can include the surrounding splice donors and acceptors of the neighboring intron.

There can be a replacement of the chromosomal DNA between the 5' locus and the 3' locus. The replacement can be a single exon replacement. The single exon replacement can be a replacement of exon 2, exon 8, exon 43, exon 44, exon 45, exon 46, exon 50, exon 51, exon 52, exon 53, or exon 70. The 5' locus can be proximal to a 5' boundary of a single exon selected from the group consisting of exon 2, exon 8, exon 43, exon 44, exon 45, exon 46, exon 50, exon 51, exon 52, exon 53, or exon 70. The 3' locus can be proximal to a 3' boundary of a single exon selected from the group consisting of exon 2, exon 8, exon 43, exon 44, exon 45, exon 46, exon 50, exon 51, exon 52, exon 53, or exon 70. The 5' locus can proximal to a 5' boundary and a 3' locus can be proximal to the 3' boundary of a single exon selected from the group consisting of exon 2, exon 8, exon 43, exon 44, exon 45, exon 46, exon 50, exon 51, exon 52, exon 53, or exon 70. Proximal to the boundary of the exon can include the surrounding splice donors and acceptors of the neighboring intron or neighboring exon.

The replacement can be a multi-exon replacement. The multi-exon replacement can be a replacement of exons 45-53 or exons 45-55. The 5' locus can be proximal to a 5' boundary of multiple exons selected from the group consisting of exons 45-53 or exons 45-55. The 3' locus can be proximal to a 3' boundary of multiple exons selected from the group consisting of exons 45-53 or exons 45-55. The 5' locus can proximal to a 5' boundary and a 3' locus can be proximal to the 3' boundary of multiple exons selected from the group consisting of exons 45-53 or exons 45-55. Proximal to the boundary of the exon can include the surrounding splice donors and acceptors of the neighboring intron or neighboring exon.

The method can further comprise introducing into the cell a polynucleotide donor template comprising at least a portion of the wild type dystrophin gene or cDNA and the replacement is by homology directed repair (HDR).

The at least a portion of the wild-type dystrophin gene or cDNA can include at least a part of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA. The at least a portion of the wild-type dystrophin gene or cDNA can include exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA.

The method can further comprise introducing into the cell one guide ribonucleic acid (gRNA) and a polynucleotide donor template comprising at least a portion of the wild-type dystrophin gene. The one or more DNA endonucleases can be one or more Cas9 or Cpf1 endonucleases that effect one single-strand break (SSB) or double-strand break (DSB) at a locus within or near the dystrophin gene that facilitates insertion of a new sequence from the polynucleotide donor template into the chromosomal DNA at the locus that results in permanent insertion or correction of one or more exons or aberrant intronic splice acceptor or donor sites within or near the dystrophin gene and results in restoration of the dystrophin reading frame and restoration of the dystrophin protein activity. The gRNA can comprise a spacer sequence that is complementary to a segment of the locus.

The method can further comprise introducing into the cell one or more guide ribonucleic acid (gRNAs) and a polynucleotide donor template comprising at least a portion of the wild-type dystrophin gene. The one or more DNA endonucleases can be one or more Cas9 or Cpf1 endonucleases that effect a pair of single-strand breaks (SSBs) or double-strand breaks (DSBs), the first at a 5' locus and the second at a 3' locus, within or near the dystrophin gene that facilitates insertion of a new sequence from the polynucleotide donor template into the chromosomal DNA between the 5' locus and the 3' locus that results in a permanent insertion or correction of one or more exons or aberrant intronic splice acceptor or donor sites between the 5' locus and the 3' locus within or near the dystrophin gene and results in restoration of the dystrophin reading frame and restoration of the dystrophin protein activity.

One gRNA can create a pair of SSBs or DSBs. One gRNA can comprise a spacer sequence that is complementary to either the 5' locus, the 3' locus, or a segment between the 5' locus and the 3' locus. A first gRNA can comprise a spacer sequence that is complementary to a segment of the 5' locus and the second gRNA can comprise a spacer sequence that is complementary to a segment of the 3' locus.

The one or more gRNAs can be one or more single-molecule guide RNAs (sgRNAs). The one or more gRNAs or one or more sgRNAs can be one or more modified gRNAs or one or more modified sgRNAs. The one or more DNA endonucleases can be pre-complexed with the one or more gRNAs or one or more sgRNAs.

There can be an insertion between the 5' locus and the 3' locus.

The insertion can be a single exon insertion. The single exon insertion can be an insertion of exon 2, exon 8, exon 43, exon 44, exon 45, exon 46, exon 50, exon 51, exon 52, exon 53, or exon 70. The 5' locus or 3' locus can be proximal to a boundary of a single exon selected from the group consisting of exon 2, exon 8, exon 43, exon 44, exon 45, exon 46, exon 50, exon 51, exon 52, exon 53, and exon 70. Proximal to the boundary of the exon can include the surrounding splice donors and acceptors of the neighboring intron or neighboring exon.

The insertion can be a multi-exon insertion. The multi-exon insertion can be an insertion of exons 45-53 or exons 45-55. The 5' locus or 3' locus can be proximal to a boundary of multiple exons selected from the group consisting of exons 45-53 or exons 45-55. Proximal to the boundary of the exon can include the surrounding splice donors and acceptors of the neighboring intro.

The at least a portion of the wild-type dystrophin gene or cDNA can include at least a part of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA. The at least a portion of the wild-type dystrophin gene or cDNA can include exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA.

The insertion or correction can be by homology directed repair (HDR).

The donor template can be a single or double stranded polynucleotide.

The Cas9 or Cpf1 mRNA, gRNA, and donor template can be each formulated into separate lipid nanoparticles or all co-formulated into a lipid nanoparticle.

The Cas9 or Cpf1 mRNA can be formulated into a lipid nanoparticle, and both the gRNA and donor template can be delivered to the cell by an adeno-associated virus (AAV) vector.

The Cas9 or Cpf1 mRNA can be formulated into a lipid nanoparticle, and the gRNA can be delivered to the cell by electroporation and donor template can be delivered to the cell by an adeno-associated virus (AAV) vector.

The dystrophin gene can be located on Chromosome X: 31,117,228-33,344,609 (Genome Reference Consortium—GRCh38/hg38).

Also provided herein is one or more guide ribonucleic acids (gRNAs) for editing a dystrophin gene in a cell from a patient with DMD. The one or more gRNAs and/or sgRNAs can comprise a spacer sequence selected from the group consisting of the nucleic acid sequences in SEQ ID Nos: 1-1,410,472 of the Sequence Listing. The one or more gRNAs can be one or more single-molecule guide RNAs (sgRNAs). The one or more gRNAs or one or more sgRNAs can be one or more modified gRNAs or one or more modified sgRNAs.

Provided herein are cells that have been modified by the preceding methods to permanently delete or correct one or more exons or aberrant intronic splice acceptor or donor sites within the dystrophin gene and restore the dystrophin reading frame and restore the dystrophin protein activity. Further provided herein are methods for ameliorating DMD by the administration of cells that have been modified by the preceding methods to a DMD patient.

It is understood that the inventions described in this specification are not limited to the examples summarized in this Summary. Various other aspects are described and exemplified herein.

BRIEF DESCRIPTION OF THE DRAWINGS

Various aspects of materials and methods for treatment of DMD disclosed and described in this specification can be better understood by reference to the accompanying figures, in which:

FIG. 4A describes the cutting efficiency of *S. pyogenes* gRNAs in HEK293 Ts targeting the splice acceptor of Exons 43, 44, 45, 46, 50, 51, 52, 53 and 55 of the dystrophin gene.

FIG. 4C describes the cutting efficiency of Cpf1 gRNAs in HEK293 Ts targeting the splice acceptors of Exons 43, 44, 45, 46, 50, 51, 52, 53 and 55 of the dystrophin gene.

FIGS. 5A-B describe cutting efficiencies and splice acceptor knock-out efficiencies of *S. pyogenes* gRNAs in HEK293 Ts targeting Exons 51, 45, 53, 44, 46, 52, 50, 43, and 55 of the dystrophin gene.

FIG. 6 describes cutting efficiencies and splice acceptor knock-out efficiencies of *N. meningitides* (NM), *S. thermophiles* (ST), and *S. aureus* (SA) gRNAs in HEK293 Ts targeting Exons 51, 45, 53, 44, 46, 52, 50, 43, and 55 of the dystrophin gene.

FIG. 10A, FIG. 10B, and FIG. 10C describe clonal analysis of clonal deletion events.

FIG. 11A and FIG. 11B describe sanger sequencing of Δ52 clones. SEQ ID NO: 1420000 corresponds to FIG. 11A. SEQ ID NO: 1420001 corresponds to FIG. 11B.

FIGS. 12A-E describe the cutting efficiencies of gRNAs selected via an in-vitro transcribed (IVT) gRNA screen.

FIG. 14A depicts a three primer PCR assay.

FIG. 14B depicts results from the three primer PCR assay.

FIG. 14C describes data generated from the three primer PCR assay.

FIGS. 19A-19VV describe the results of a large scale lentiviral screen.

BRIEF DESCRIPTION OF THE SEQUENCE LISTING

Figure 1A:
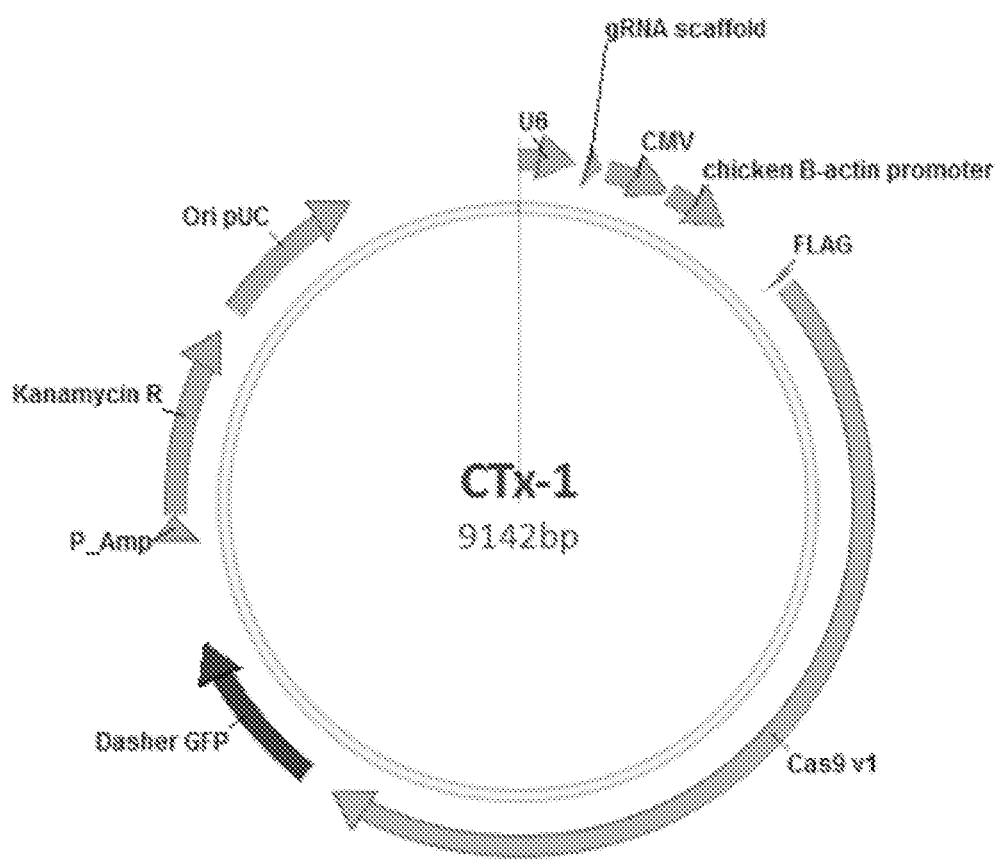
FIG. 1A is a plasmid (CTx-1) comprising a codon optimized gene for *S. pyogenes* Cas9 endonuclease. The CTx-1 plasmid also comprises a gRNA scaffold sequence, which includes a 20 bp spacer sequence from the sequences listed in SEQ ID NOs: 1-467,030 of the Sequence Listing or a 19 bp spacer sequence from the sequences listed in SEQ ID NOs: 1,410,430-1,410,472 of the Sequence Listing.

SEQ ID NOs: 1-467,030 is a list of gRNA 20 bp spacer sequences for targeting the dystrophin gene with a *S. pyogenes* Cas9 endonuclease.

SEQ ID NOs: 467,031-528,196 is a list of gRNA 20 bp spacer sequences for targeting the dystrophin gene with a *S. aureus* Cas9 endonuclease.

SEQ ID NOs: 528,197-553,198 is a list of gRNA 24 bp spacer sequences for targeting the dystrophin gene with a *S. thermophilus* Cas9 endonuclease.

SEQ ID NOs: 553,199-563,911 is a list of gRNA 24 bp spacer sequences for targeting the dystrophin gene with a *T. denticola* Cas9 endonuclease.

SEQ ID NOs: 563,912-627,854 is a list of gRNA 24 bp spacer sequences for targeting the dystrophin gene with a *N. meningitides* Cas9 endonuclease.

SEQ ID NOs: 627,855-1,410,399 is a list of gRNA 20-24 bp spacer sequences for targeting the dystrophin gene with an *Acidominoccocus*, a Lachnospiraceae, and a *Franciscella Novicida* Cpf1 endonuclease.

SEQ ID NOs: 1,410,400-1,410,402 is a list of gRNA 24 bp spacer sequences for targeting the dystrophin gene with a *N. meningitides* Cas9 endonuclease.

SEQ ID NOs: 1,410,403-1,410,429 is a list of gRNA 23 bp spacer sequences for targeting the dystrophin gene with an *Acidominoccocus*, a Lachnospiraceae, and a *Franciscella Novicida* Cpf1 endonuclease.

SEQ ID NOs: 1,410,430-1,410,472 is a list of gRNA 19 bp spacer sequences for targeting the dystrophin gene with a *S. pyogenes* Cas9 endonuclease.

DETAILED DESCRIPTION

Duchenne Muscular Dystrophy (DMD)

DMD is caused by mutations in the dystrophin gene (Chromosome X: 31,117,228-33,344,609 (Genome Reference Consortium—GRCh38/hg38)). With a genomic region of over 2.2 megabases in length, dystrophin is the second largest human gene. The dystrophin gene contains 79 exons that are processed into an 11,000 base pair mRNA that is translated into a 427 kDa protein. Functionally, dystrophin acts as a linker between the actin filaments and the extracellular matrix within muscle fibers. The N terminus of dystrophin is an actin-binding domain, while the C terminus interacts with a transmembrane scaffold that anchors the muscle fiber to the extracellular matrix. Upon muscle contraction, dystrophin provides structural support that allows the muscle tissue to withstand mechanical force. DMD is caused by a wide variety of mutations within the dystrophin gene that result in premature stop codons and therefore a truncated dystrophin protein. Truncated dystrophin proteins do not contain the C terminus, and therefore cannot provide the structural support necessary to withstand the stress of muscle contraction. As a result, the muscle fibers pull themselves apart, which leads to muscle wasting.

Therapeutic Approach

Provided herein are cellular, ex vivo and in vivo methods for using genome engineering tools to create permanent changes to the genome that can restore the dystrophin reading frame and restore dystrophin protein activity. Such methods use endonucleases, such as CRISPR/Cas9 nucleases, to permanently delete (excise), insert, or replace (delete and insert) exons (i.e., mutations in the coding and/or splicing sequences) in the genomic locus of the dystrophin gene. In this way, the present invention mimics the product produced by exon skipping, and/or restores the reading frame with as few as a single treatment (rather than deliver exon skipping oligos for the lifetime of the patient). Preclinical studies have been performed regarding expression of the C terminus of dystrophin by making targeted changes to the genome using Zinc-Finger-, TALE-, and CRISPR/Cas9-based nucleases. In one example, a large genomic region was deleted that is projected to treat over 60% of the patients with DMD.

Provided herein are methods for treating a patient with DMD. An example of such method is an ex vivo cell based therapy. For example, a DMD patient specific iPS cell line is created. Then, the chromosomal DNA of these iPS cells is corrected using the materials and methods described herein. Next, the corrected iPSCs are differentiated into Pax7+ muscle progenitor cells. Finally, the progenitor cells are implanted into the patient. There are many advantages to this ex vivo approach.

One advantage of an ex vivo cell therapy approach is the ability to conduct a comprehensive analysis of the therapeutic prior to administration. All nuclease based therapeutics have some level of off-target effects. Performing gene correction ex vivo allows one to fully characterize the corrected cell population prior to implantation. Aspects of the present disclosure include sequencing the entire genome of the corrected cells to ensure that the off-target cuts, if any, are in genomic locations associated with minimal risk to the patient. Furthermore, clonal populations of cells can be isolated prior to implantation.

Another advantage of ex vivo cell therapy relates to genetic correction in iPSCs compared to other primary cell sources. iPSCs are prolific, making it easy to obtain the large number of cells that will be required for a cell based therapy. Furthermore, iPSCs are an ideal cell type for performing clonal isolations. This allows screening for the correct genomic correction, without risking a decrease in viability. In contrast, other potential cell types, such as primary myoblasts, are viable for only a few passages and difficult to clonally expand. Also, patient specific DMD myoblasts will be unhealthy due to the lack of dystrophin protein. On the other hand, patient derived DMD iPSCs will not display a diseased phenotype, as they do not express dystrophin in this differentiation state. Therefore, manipulation of DMD iPSCs will be much easier, and will shorten the amount of time needed to make the desired genetic correction.

A further advantage of ex vivo cell therapy relates to implantation of myogenic Pax7+ progenitors versus myoblasts. Pax7+ cells are accepted as myogenic satellite cells. Pax7+ progenitors are mono-nuclear cells that sit on the periphery of the multi-nucleated muscle fibers. In response to injury, the progenitors divide and fuse to the existing fibers. In contrast, myoblasts fuse directly to the muscle fiber upon implantation and have minimal proliferative capacity in vivo. Therefore, myoblasts cannot aid in healing following repeated injury, while Pax7+ progenitors can function as a reservoir and help heal the muscle for the lifetime of the patient.

Another example of such method is an in vivo based therapy. In this method, the chromosomal DNA of the cells in the patient is corrected using the materials and methods described herein.

The advantage of in vivo gene therapy is the ease of therapeutic production and administration. The same therapeutic cocktail will have the potential to reach a subset of the DMD patient population (n>1). In contrast, the ex vivo cell therapy proposed requires a custom therapeutic to be developed for each patient (n=1). Ex vivo cell therapy development requires time, which certain advanced DMD patients may not have.

Also provided herein is a cellular method for editing the dystrophin gene in a human cell by genome editing. For example, a cell is isolated from a patient or animal. Then, the chromosomal DNA of the cell is corrected using the materials and methods described herein.

A number of types of genomic target sites can be present in addition to mutations in the coding and splicing sequences.

The regulation of transcription and translation implicates a number of different classes of sites that interact with cellular proteins or nucleotides. Often the DNA binding sites of transcription factors or other proteins can be targeted for mutation or deletion to study the role of the site, though they can also be targeted to change gene expression. Sites can be added through non-homologous end joining (NHEJ) or direct genome editing by homology directed repair (HDR). Increased use of genome sequencing, RNA expression and genome-wide studies of transcription factor binding have increased our ability to identify how the sites lead to developmental or temporal gene regulation. These control systems can be direct or can involve extensive cooperative regulation that can require the integration of activities from multiple enhancers. Transcription factors typically bind 6-12 bp-long degenerate DNA sequences. The low level of specificity provided by individual sites suggests that complex interactions and rules are involved in binding and the functional outcome. Binding sites with less degeneracy can provide simpler means of regulation. Artificial transcription factors can be designed to specify longer sequences that have less similar sequences in the genome and have lower potential for off-target cleavage. Any of these types of binding sites can be mutated, deleted or even created to enable changes in gene regulation or expression (Canver, M. C. et al., Nature (2015)).

Another class of gene regulatory regions having these features is microRNA (miRNA) binding sites. miRNAs are non-coding RNAs that play key roles in posttranscriptional gene regulation. miRNA can regulate the expression of 30% of all mammalian protein-encoding genes. Specific and potent gene silencing by double stranded RNA (RNAi) was discovered, plus additional small noncoding RNA (Canver, M. C. et al., Nature (2015)). The largest class of noncoding RNAs important for gene silencing are miRNAs. In mammals, miRNAs are first transcribed as long RNA transcripts, which can be separate transcriptional units, part of protein introns, or other transcripts. The long transcripts are called primary miRNA (pri-miRNA) that include imperfectly base-paired hairpin structures. These pri-miRNAs can be cleaved into one or more shorter precursor miRNAs (pre-miRNAs) by Microprocessor, a protein complex in the nucleus, involving Drosha.

Pre-miRNAs are short stem loops ~70 nucleotides in length with a 2-nucleotide 3'-overhang that are exported, into the mature 19-25 nucleotide miRNA:miRNA* duplexes. The miRNA strand with lower base pairing stability (the guide strand) can be loaded onto the RNA-induced silencing complex (RISC). The passenger guide strand (marked with *), can be functional, but is usually degraded. The mature miRNA tethers RISC to partly complementary sequence motifs in target mRNAs predominantly found within the 3' untranslated regions (UTRs) and induces posttranscriptional gene silencing (Bartel, D. P. Cell 136, 215-233 (2009); Saj, A. & Lai, E. C. Curr Opin Genet Dev 21, 504-510 (2011)).

miRNAs can be important in development, differentiation, cell cycle and growth control, and in virtually all biological pathways in mammals and other multicellular organisms. miRNAs can also be involved in cell cycle control, apoptosis and stem cell differentiation, hematopoiesis, hypoxia, muscle development, neurogenesis, insulin secretion, cholesterol metabolism, aging, viral replication and immune responses.

A single miRNA can target hundreds of different mRNA transcripts, while an individual transcript can be targeted by many different miRNAs. More than 28645 microRNAs have been annotated in the latest release of miRBase (v.21). Some miRNAs can be encoded by multiple loci, some of which can be expressed from tandemly co-transcribed clusters. The features allow for complex regulatory networks with multiple pathways and feedback controls. miRNAs can be integral parts of these feedback and regulatory circuits and can help regulate gene expression by keeping protein production within limits (Herranz, H. & Cohen, S. M. Genes Dev 24, 1339-1344 (2010); Posadas, D. M. & Carthew, R. W. Curr Opin Genet Dev 27, 1-6 (2014)).

miRNA can also be important in a large number of human diseases that are associated with abnormal miRNA expression. This association underscores the importance of the miRNA regulatory pathway. Recent miRNA deletion studies have linked miRNA with regulation of the immune responses (Stern-Ginossar, N. et al., Science 317, 376-381 (2007)).

miRNA also have a strong link to cancer and can play a role in different types of cancer. miRNAs have been found to be downregulated in a number of tumors. miRNA can be important in the regulation of key cancer-related pathways, such as cell cycle control and the DNA damage response, and can therefore be used in diagnosis and can be targeted clinically. MicroRNAs can delicately regulate the balance of angiogenesis, such that experiments depleting all microRNAs suppress tumor angiogenesis (Chen, S. et al., Genes Dev 28, 1054-1067 (2014)).

As has been shown for protein coding genes, miRNA genes can also be subject to epigenetic changes occurring with cancer. Many miRNA loci can be associated with CpG islands increasing their opportunity for regulation by DNA methylation (Weber, B., Stresemann, C., Brueckner, B. & Lyko, F. Cell Cycle 6, 1001-1005 (2007)). The majority of studies have used treatment with chromatin remodeling drugs to reveal epigenetically silenced miRNAs.

In addition to their role in RNA silencing, miRNA can also activate translation (Posadas, D. M. & Carthew, R. W. Curr Opin Genet Dev 27, 1-6 (2014)). Knocking out these sites can lead to decreased expression of the targeted gene, while introducing these sites can increase expression.

Individual miRNA can be knocked out most effectively by mutating the seed sequence (bases 2-8 of the microRNA), which can be important for binding specificity. Cleavage in this region, followed by mis-repair by NHEJ can effectively abolish miRNA function by blocking binding to target sites. miRNA could also be inhibited by specific targeting of the special loop region adjacent to the palindromic sequence. Catalytically inactive Cas9 can also be used to inhibit shRNA expression (Zhao, Y. et al., Sci Rep 4, 3943 (2014)). In addition to targeting the miRNA, the binding sites can also be targeted and mutated to prevent the silencing by miRNA.

Human Cells

For ameliorating DMD, as described and illustrated herein, the principal targets for gene editing are human cells. For example, in the ex vivo methods, the human cells can be somatic cells, which after being modified using the techniques as described, can give rise to Pax7+ muscle progenitor cells. For example, in the in vivo methods, the human cells can be muscle cells or muscle precursor cells.

By performing gene editing in autologous cells that are derived from and therefore already completely matched with the patient in need, it is possible to generate cells that can be safely re-introduced into the patient, and effectively give rise to a population of cells that can be effective in ameliorating one or more clinical conditions associated with the patient's disease.

Progenitor cells (also referred to as stem cells herein) are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell can derive from a multipotent cell that itself is derived from a multipotent cell, and so on. While each of these multipotent cells can be considered stem cells, the range of cell types that each can give rise to can vary considerably. Some differentiated cells also have the capacity to give rise to cells of greater developmental potential. Such capacity can be natural or may be induced artificially upon treatment with various factors. In many biological instances, stem cells can be also "multipotent" because they can produce progeny of more than one distinct cell type, but this is not required for "stem-ness."

Self-renewal can be another important aspect of the stem cell. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated," or "differentiating" is a relative term. A "differentiated cell" is a cell that has progressed further down the developmental pathway than the cell to which it is being compared. Thus, stem cells can differentiate into lineage-restricted precursor cells (such as a myocyte progenitor cell), which in turn can differentiate into other types of precursor cells further down the pathway (such as a myocyte precursor), and then to an end-stage differentiated cell, such as a myocyte, which plays a characteristic role in a certain tissue type, and may or may not retain the capacity to proliferate further.

Induced Pluripotent Stem Cells

In some examples, the genetically engineered human cells described herein can be induced pluripotent stem cells (iPSCs). An advantage of using iPSCs is that the cells can be derived from the same subject to which the progenitor cells are to be administered. That is, a somatic cell can be obtained from a subject, reprogrammed to an induced pluripotent stem cell, and then re-differentiated into a progenitor cell to be administered to the subject (e.g., autologous cells). Because the progenitors are essentially derived from an autologous source, the risk of engraftment rejection or allergic response can be reduced compared to the use of cells from another subject or group of subjects. In addition, the use of iPSCs negates the need for cells obtained from an embryonic source. Thus, in one aspect, the stem cells used in the disclosed methods are not embryonic stem cells.

Although differentiation is generally irreversible under physiological contexts, several methods have been recently developed to reprogram somatic cells to iPSCs. Exemplary methods are known to those of skill in the art and are described briefly herein below.

The term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. Reprogramming encompasses complete reversion of the differentiation state of a differentiated cell (e.g., a somatic cell) to a pluripotent state or a multipotent state. Reprogramming can encompass complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain examples described herein, reprogramming of a differentiated cell (e.g., a somatic cell) can cause the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a myogenic stem cell). Reprogramming is also distinct from promoting the self-renewal or proliferation of cells that are already pluripotent or multipotent, although the compositions and methods described herein can also be of use for such purposes, in some examples.

Many methods are known in the art that can be used to generate pluripotent stem cells from somatic cells. Any such method that reprograms a somatic cell to the pluripotent phenotype would be appropriate for use in the methods described herein.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, Cell 126(4): 663-76 (2006). iPSCs resemble ES cells, as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germ line transmission [see, e.g., Maherali and Hochedlinger, Cell Stem Cell. 3(6):595-605 (2008)], and tetraploid complementation.

Human iPSCs can be obtained using similar transduction methods, and the transcription factor trio, OCT4, SOX2, and NANOG, has been established as the core set of transcription factors that govern pluripotency; see, e.g., Budniatzky and Gepstein, Stem Cells Transl Med. 3(4):448-57 (2014); Barrett et al., Stem Cells Trans Med 3:1-6 sctm. 2014-0121 (2014); Focosi et al., Blood Cancer Journal 4: e211 (2014); and references cited therein. The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 7(5):618-30 (2010). Reprogramming can be achieved by introducing a combination of nucleic acids encoding stem cell-associated genes, including, for example, Oct-4 (also known as Oct-3/4 or Pouf51), Soxl, Sox2, Sox3, Sox 15, Sox 18, NANOG, Klfl, Klf2, Klf4, Klf5, NR5A2, c-Myc, 1-Myc, n-Myc, Rem2, Tert, and LIN28. Reprogramming using the methods and compositions described herein can further comprise introducing one or more of Oct-3/4, a member of the Sox family, a member of the Klf family, and a member of the Myc family to a somatic cell. The methods and compositions described herein can further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one aspect the reprogramming is not effected by a method that alters the genome. Thus, in such examples, reprogramming can be achieved, e.g., without the use of viral or plasmid vectors.

The efficiency of reprogramming (i.e., the number of reprogrammed cells) derived from a population of starting cells can be enhanced by the addition of various agents, e.g., small molecules, as shown by Shi et al., Cell-Stem Cell 2:525-528 (2008); Huangfu et al., Nature Biotechnology 26(7):795-797 (2008) and Marson et al., Cell-Stem Cell 3: 132-135 (2008). Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-IH,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzam ides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-CI-UCHA (e.g., 6-(3-chlorophenylureido) caproic hydroxamic acid), AOE (2-amino-8-oxo-9, 10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbxl5, Ecatl, Esgl, Eras, Gdf3, Fgf4, Cripto, Daxl, Zpf296, Slc2a3, Rexl, Utfl, and Natl. In one case, for example, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. Detection can involve, not only RT-PCR, but can also include detection of protein markers. Intracellular markers can be best identified via RT-PCR, or protein detection methods such as immunocytochemistry, while cell surface markers are readily identified, e.g., by immunocytochemistry.

The pluripotent stem cell character of isolated cells can be confirmed by tests evaluating the ability of the iPSCs to differentiate into cells of each of the three germ layers. As one example, teratoma formation in nude mice can be used to evaluate the pluripotent character of the isolated clones. The cells can be introduced into nude mice and histology and/or immunohistochemistry can be performed on a tumor arising from the cells. The growth of a tumor comprising cells from all three germ layers, for example, further indicates that the cells are pluripotent stem cells.

Creating DMD Patient Specific iPSCs

One step of the ex vivo methods of the present disclosure can involve creating a DMD patient specific iPS cell, DMD patient specific iPS cells, or a DMD patient specific iPS cell line. There are many established methods in the art for creating patient specific iPS cells, as described in Takahashi and Yamanaka 2006; Takahashi, Tanabe et al. 2007. In addition, differentiation of pluripotent cells toward the muscle lineage can be accomplished by technology developed by Anagenesis Biotechnologies, as described in International patent application publication numbers WO2013/030243 and WO2012/101114. For example, the creating step can comprise: a) isolating a somatic cell, such as a skin cell or fibroblast from the patient; and b) introducing a set of pluripotency-associated genes into the somatic cell in order to induce the cell to become a pluripotent stem cell. The set of pluripotency-associated genes can be one or more of the genes selected from the group consisting of OCT4, SOX2, KLF4, Lin28, NANOG, and cMYC.

Genome Editing

Genome editing generally refers to the process of modifying the nucleotide sequence of a genome, preferably in a precise or pre-determined manner. Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end-joining (NHEJ), as recently reviewed in Cox et al., Nature Medicine 21(2), 121-31 (2015). NHEJ directly joins the DNA ends resulting from a double-strand break, sometimes with the loss or addition of nucleotide sequence, which can disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-strand oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ", in which the genetic outcome is similar to NHEJ in that small deletions and insertions can occur at the cleavage site. MMEJ can make use of homologous sequences of a few basepairs flanking the DNA break site to drive a more favored DNA end joining repair outcome, and recent reports have further elucidated the molecular mechanism of this process; see, e.g., Cho and Greenberg, Nature 518, 174-76 (2015); Kent et al., Nature Structural and Molecular Biology, Adv. Online doi:10.1038/nsmb.2961 (2015); Mateos-Gomez et al., Nature 518, 254-57 (2015); Ceccaldi et al., Nature 528, 258-62 (2015). In some instances it may be possible to predict likely repair outcomes based on analysis of potential microhomologies at the site of the DNA break.

Each of these genome editing mechanisms can be used to create desired genomic alterations. A step in the genome editing process can be to create one or two DNA breaks, the latter as double-strand breaks or as two single-stranded breaks, in the target locus as close as near to the site of intended mutation. This can be achieved via the use of site-directed polypeptides, as described and illustrated herein.

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair or non-homologous end joining or alternative non-homologous end joining (A-NHEJ) or microhomology-mediated end joining). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that can be homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide, double-stranded oligonucleotide, or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence or polynucleotide donor template) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary structures (e.g., hairpins) and/or comprise unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

Type II CRISPR Systems crRNA biogenesis in a Type II CRISPR system in nature requires a trans-activating CRISPR RNA (tracrRNA). The tracrRNA can be modified by endogenous RNaseIII, and then hybridizes to a crRNA repeat in the pre-crRNA array. Endogenous RNaseIII can be recruited to cleave the pre-crRNA. Cleaved crRNAs can be subjected to exoribonuclease trimming to produce the mature crRNA form (e.g., 5' trimming). The tracrRNA can remain hybridized to the crRNA, and the tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science*, 337(6096):816-821 (2012) showed that the CRISPR/Cas9 system is useful for RNA-programmable genome editing, and international patent application publication number WO2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays can be processed into mature crRNAs without the requirement of an additional trans-activating tracrRNA. The Type V CRISPR array can be processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems can start with 20-24 nucleotides of spacer sequence followed by about 22 nucleotides of direct repeat. Also, Cpf1 can utilize a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Figure 1B:
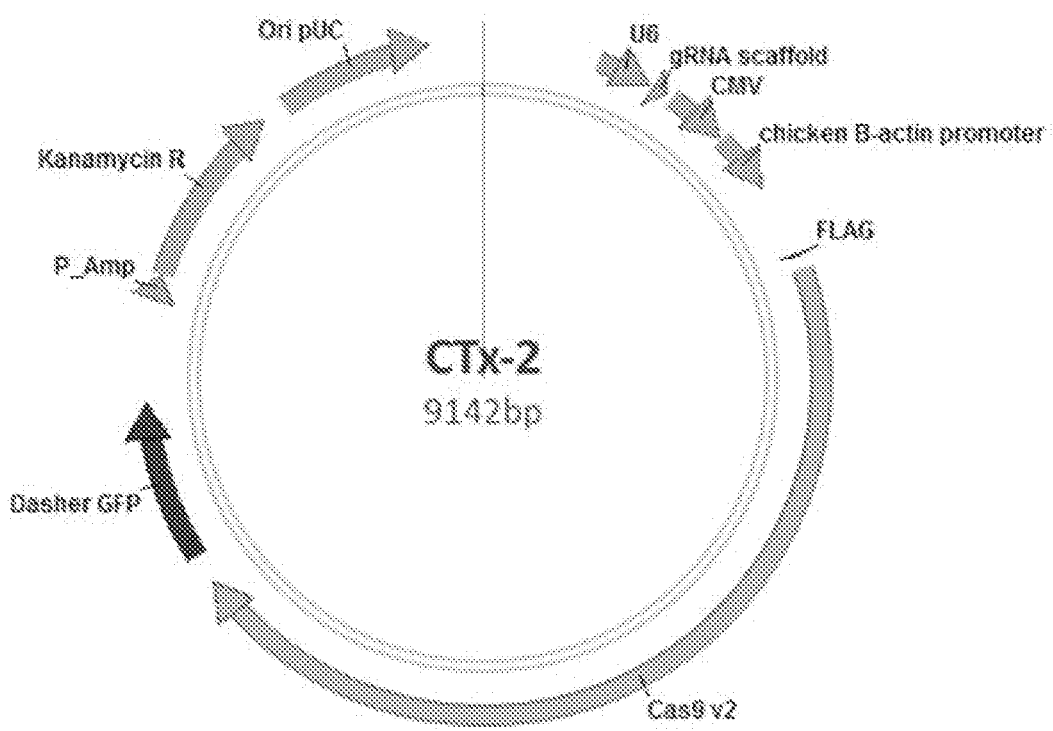
FIG. 1B is a plasmid (CTx-2) comprising a different codon optimized gene for *S. pyogenes* Cas9 endonuclease. The CTx-2 plasmid also comprises a gRNA scaffold sequence, which includes a 20 bp spacer sequence from the sequences listed in SEQ ID NOs: 1-467,030 of the Sequence Listing or a 19 bp spacer sequence from the sequences listed in SEQ ID NOs: 1,410,430-1,410,472 of the Sequence Listing.
Figure 1C:
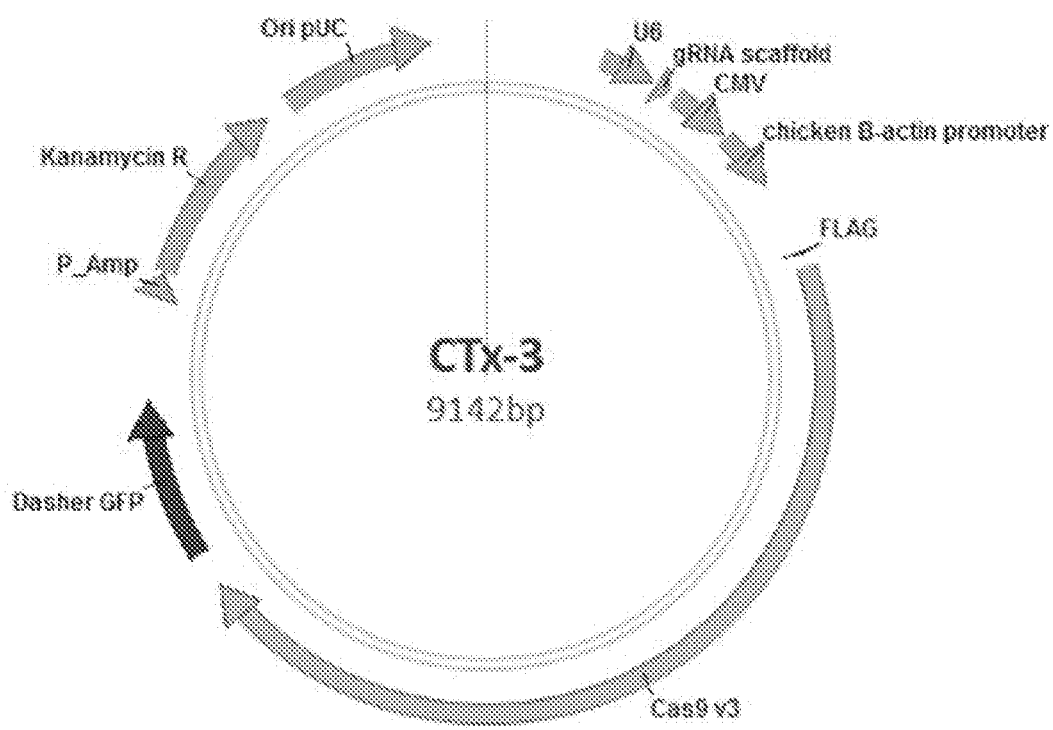
FIG. 1C is a plasmid (CTx-3) comprising yet another different codon optimized gene for *S. pyogenes* Cas9 endonuclease. The CTx-3 plasmid also comprises a gRNA scaffold sequence, which includes a 20 bp spacer sequence from the sequences listed in SEQ ID NOs: 1-467,030 of the Sequence Listing or a 19 bp spacer sequence from the sequences listed in SEQ ID NOs: 1,410,430-1,410,472 of the Sequence Listing.
Figure 2A:
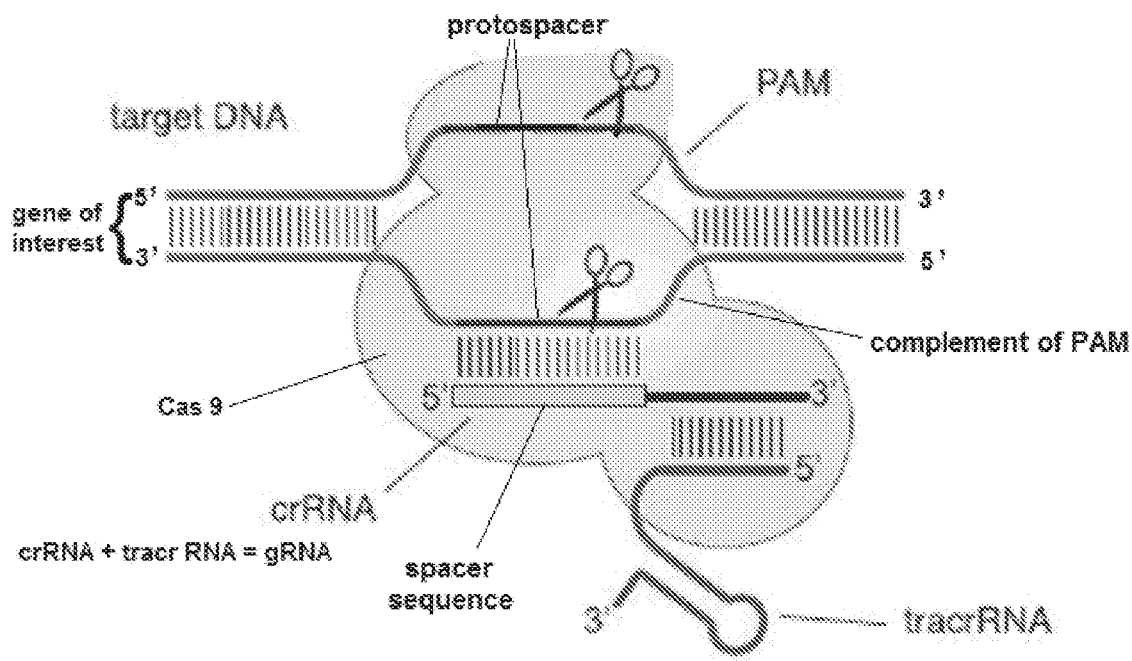
FIG. 2A is a depiction of the type II CRISPR/Cas system.
Figure 2B:
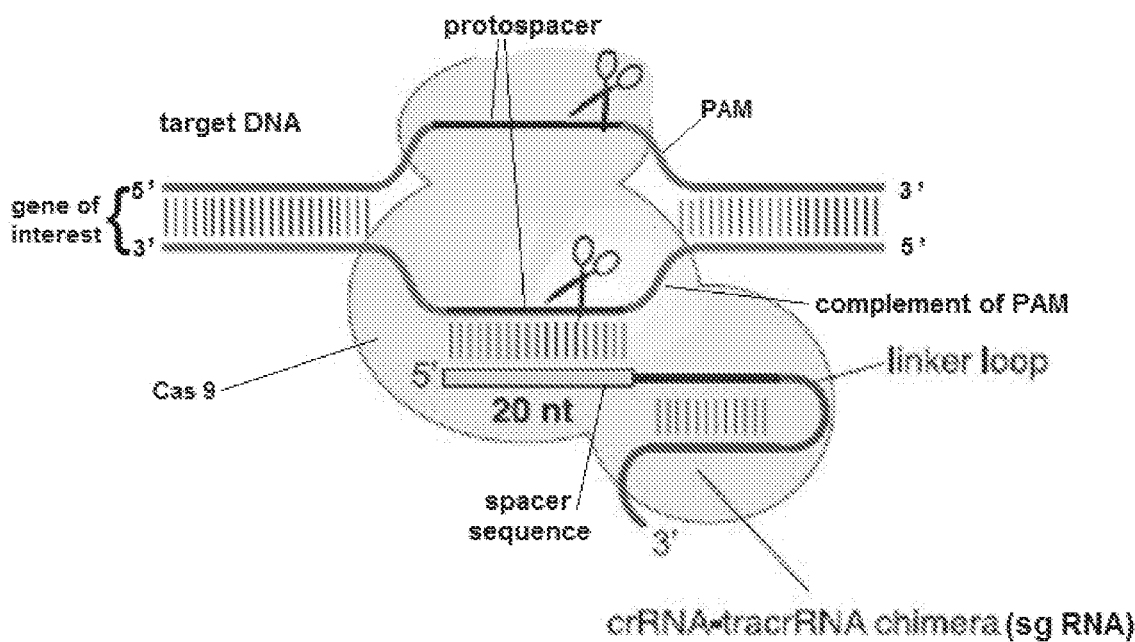
FIG. 2B is a depiction of the type II CRISPR/Cas system.

Exemplary CRISP R/Cas polypeptides include the Cas9 polypeptides in FIG. 1 of Fonfara et al., *Nucleic Acids Research*, 42: 2577-2590 (2014). The CRISPR/Cas gene naming system has undergone extensive rewriting since the Cas genes were discovered. FIG. 5 of Fonfara, supra, provides PAM sequences for the Cas9 polypeptides from various species.

Site-Directed Polypeptides

A site-directed polypeptide is a nuclease used in genome editing to cleave DNA. The site-directed can be administered to a cell or a patient as either: one or more polypeptides, or one or more mRNAs encoding the polypeptide.

In the context of a CRISP R/Cas or CRISPR/Cpf1 system, the site-directed polypeptide can bind to a guide RNA that, in turn, specifies the site in the target DNA to which the polypeptide is directed. In the CRISPR/Cas or CRISPR/Cpf1 systems disclosed herein, the site-directed polypeptide can be an endonuclease, such as a DNA endonuclease.

A site-directed polypeptide can comprise a plurality of nucleic acid-cleaving (i.e., nuclease) domains. Two or more nucleic acid-cleaving domains can be linked together via a linker. For example, the linker can comprise a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, a HNH nuclease domain and a RuvC domain. Herein, the "Cas9" refers to both naturally-occurring and recombinant Cas9s. Cas9 enzymes contemplated herein can comprise a HNH or HNH-like nuclease domain, and/or a RuvC or RuvC-like nuclease domain.

HNH or HNH-like domains comprise a McrA-like fold. HNH or HNH-like domains comprises two antiparallel β-strands and an α-helix. HNH or HNH-like domains comprises a metal binding site (e.g., a divalent cation binding site). HNH or HNH-like domains can cleave one strand of a target nucleic acid (e.g., the complementary strand of the crRNA targeted strand).

RuvC or RuvC-like domains comprise an RNaseH or RNaseH-like fold. RuvC/RNaseH domains are involved in a diverse set of nucleic acid-based functions including acting on both RNA and DNA. The RNaseH domain comprises 5 β-strands surrounded by a plurality of α-helices. RuvC/RNaseH or RuvC/RNaseH-like domains comprise a metal binding site (e.g., a divalent cation binding site). RuvC/RNaseH or RuvC/RNaseH-like domains can cleave one strand of a target nucleic acid (e.g., the non-complementary strand of a double-stranded target DNA).

Site-directed polypeptides can introduce double-strand breaks or single-strand breaks in nucleic acids, e.g., genomic DNA. The double-strand break can stimulate a cell's endogenous DNA-repair pathways (e.g., homology-dependent repair (HDR) or non-homologous end joining (NHEJ) or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that are homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor polynucleotide (or donor or donor sequence) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

The site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from S. pyogenes, US2014/0068797 Sequence ID No. 8 or Sapranauskas et al., Nucleic Acids Res, 39(21): 9275-9282 (2011)], and various other site-directed polypeptides).

The site-directed polypeptide comprises at least 70, 75, 80, 85, 90, 95, 97, 99, or 100% identity to a wild-type site-directed polypeptide (e.g., Cas9 from S. pyogenes, supra) over 10 contiguous amino acids. The site-directed polypeptide can comprise at most: 70, 75, 80, 85, 90, 95, 97, 99, or 100% identity to a wild-type site-directed polypeptide (e.g., Cas9 from S. pyogenes, supra) over 10 contiguous amino acids. The site-directed polypeptide can comprise at least: 70, 75, 80, 85, 90, 95, 97, 99, or 100% identity to a wild-type site-directed polypeptide (e.g., Cas9 from S. pyogenes, supra) over 10 contiguous amino acids in a HNH nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from S. pyogenes, supra) over 10 contiguous amino acids in a HNH nuclease domain of the site-directed polypeptide. The site-directed polypeptide can comprise at least: 70, 75, 80, 85, 90, 95, 97, 99, or 100% identity to a wild-type site-directed polypeptide (e.g., Cas9 from S. pyogenes, supra) over 10 contiguous amino acids in a RuvC nuclease domain of the site-directed polypeptide. The site-directed polypeptide comprises at most: 70, 75, 80, 85, 90, 95, 97, 99, or 100% identity to a wild-type site-directed polypeptide (e.g., Cas9 from S. pyogenes, supra) over 10 contiguous amino acids in a RuvC nuclease domain of the site-directed polypeptide.

The site-directed polypeptide can comprise a modified form of a wild-type exemplary site-directed polypeptide. The modified form of the wild-type exemplary site-directed polypeptide can comprise a mutation that reduces the nucleic acid-cleaving activity of the site-directed polypeptide. The modified form of the wild-type exemplary site-directed polypeptide can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from S. pyogenes, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

The modified form of the site-directed polypeptide can comprise a mutation such that it can induce a single-strand break (SSB) on a target nucleic acid (e.g., by cutting only one of the sugar-phosphate backbones of a double-strand target nucleic acid). The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from S. pyogenes, supra). The mutation can result in one or more of the plurality of nucleic acid-cleaving domains retaining the ability to cleave the complementary strand of the target nucleic acid, but reducing its ability to cleave the non-complementary strand of the target nucleic acid. The mutation can result in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary S. pyogenes Cas9 polypeptide, such as Asp10, His840, Asn854 and Asn856, are mutated to inactivate one or more of the plurality of nucleic acid-cleaving domains (e.g., nuclease domains). The residues to be mutated can correspond to residues Asp10, His840, Asn854 and Asn856 in the wild-type exemplary S. pyogenes Cas9 polypeptide (e.g., as determined by sequence and/or structural alignment). Non-limiting examples of mutations include D10A, H840A, N854A or N856A. One skilled in the art will recognize that mutations other than alanine substitutions can be suitable.

A D10A mutation can be combined with one or more of H840A, N854A, or N856A mutations to produce a site-directed polypeptide substantially lacking DNA cleavage activity. A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity. Site-directed polypeptides that comprise one substantially inactive nuclease domain are referred to as "nickases".

Nickase variants of RNA guided endonucleases, for example Cas9, can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes. Descriptions of various CRISPR/Cas systems for use in gene editing can be found, e.g., in international patent application publication number WO2013/176772, and in *Nature Biotechnology* 32, 347-355 (2014), and references cited therein.

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation converts the mutated amino acid to a natural amino acid (e.g., selenomethionine). The mutation converts the mutated amino acid to amino acid mimics (e.g., phosphomimics). The mutation can be a conservative mutation. For example, the mutation can convert the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

The site-directed polypeptide (e.g., variant, mutated, enzymatically inactive and/or conditionally enzymatically inactive site-directed polypeptide) can target nucleic acid. The site-directed polypeptide (e.g., variant, mutated, enzymatically inactive and/or conditionally enzymatically inactive endoribonuclease) can target DNA. The site directed polypeptide (e.g., variant, mutated, enzymatically inactive and/or conditionally enzymatically inactive endoribonuclease) can target RNA.

The site-directed polypeptide can comprise one or more non-native sequences (e.g., the site-directed polypeptide is a fusion protein).

The site-directed polypeptide can comprise an amino acid sequence comprising at least 15% amino acid identity to a Cas9 from a bacterium (e.g., *S. pyogenes*), a nucleic acid binding domain, and two nucleic acid cleaving domains (i.e., a HNH domain and a RuvC domain).

The site-directed polypeptide can comprise an amino acid sequence comprising at least 15% amino acid identity to a Cas9 from a bacterium (e.g., *S. pyogenes*), and two nucleic acid cleaving domains (i.e., a HNH domain and a RuvC domain).

The site-directed polypeptide can comprise an amino acid sequence comprising at least 15% amino acid identity to a Cas9 from a bacterium (e.g., *S. pyogenes*), and two nucleic acid cleaving domains, wherein one or both of the nucleic acid cleaving domains comprise at least 50% amino acid identity to a nuclease domain from Cas9 from a bacterium (e.g., *S. pyogenes*).

The site-directed polypeptide can comprise an amino acid sequence comprising at least 15% amino acid identity to a Cas9 from a bacterium (e.g., *S. pyogenes*), two nucleic acid cleaving domains (i.e., a HNH domain and a RuvC domain), and non-native sequence (for example, a nuclear localization signal) or a linker linking the site-directed polypeptide to a non-native sequence.

The site-directed polypeptide can comprise an amino acid sequence comprising at least 15% amino acid identity to a Cas9 from a bacterium (e.g., *S. pyogenes*), two nucleic acid cleaving domains (i.e., a HNH domain and a RuvC domain), wherein the site-directed polypeptide comprises a mutation in one or both of the nucleic acid cleaving domains that reduces the cleaving activity of the nuclease domains by at least 50%.

The site-directed polypeptide can comprise an amino acid sequence comprising at least 15% amino acid identity to a Cas9 from a bacterium (e.g., *S. pyogenes*), and two nucleic acid cleaving domains (i.e., a HNH domain and a RuvC domain), wherein one of the nuclease domains comprises a mutation of aspartic acid 10, and/or wherein one of the nuclease domains can comprise a mutation of histidine 840, and wherein the mutation reduces the cleaving activity of the nuclease domain(s) by at least 50%.

The one or more site-directed polypeptides, e.g. DNA endonucleases, can comprise two nickases that together effect one double-strand break at a specific locus in the genome, or four nickases that together effect or cause two double-strand breaks at specific loci in the genome. Alternatively, one site-directed polypeptide, e.g. DNA endonuclease, can effect or cause one double-strand break at a specific locus in the genome.

Genome-Targeting Nucleic Acid

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA can comprise at least a spacer sequence that hybridizes to a target nucleic acid sequence of interest, and a CRISPR repeat sequence. In Type II systems, the gRNA also comprises a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex can bind a site-directed polypeptide, such that the guide RNA and site-direct polypeptide form a complex. The genome-targeting nucleic acid can provide target specificity to the complex by virtue of its association with the site-directed polypeptide. The genome-targeting nucleic acid thus can direct the activity of the site-directed polypeptide.

Exemplary guide RNAs include the spacer sequences in the Sequence Listing, shown with the genome location of their target sequence, which is within or near the dystrophin gene, and the associated Cas9 cut site, wherein the genome location is based on the GRCh38/hg38 human genome assembly.

Each guide RNA can be designed to include a spacer sequence complementary to its genomic target sequence, which is within or near the dystrophin gene. For example, each of the spacer sequences in the Sequence Listing can be put into a single strand guide RNA (sgRNA) (e.g., an RNA chimera) or a crRNA (along with a corresponding tracrRNA). See Jinek et al., Science, 337, 816-821 (2012) and Deltcheva et al., Nature, 471, 602-607 (2011).

The genome-targeting nucleic acid can be a double-molecule guide RNA. The genome-targeting nucleic acid can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

A single-molecule guide RNA (sgRNA) in a Type V system can comprise, in the 5' to 3' direction, a minimum CRISPR repeat sequence and a spacer sequence.

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC), which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 of Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Extension Sequence

In some examples of genome-targeting nucleic acids, a spacer extension sequence can modify activity, provide stability and/or provide a location for modifications of a genome-targeting nucleic acid. A spacer extension sequence can modify on or off target activity or specificity. In some examples, a spacer extension sequence can be provided. The spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. The spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. The spacer extension sequence can be less than 10 nucleotides in length. The spacer extension sequence can be between 10-30 nucleotides in length. The spacer extension sequence can be between 30-70 nucleotides in length.

The spacer extension sequence can comprise another moiety (e.g., a stability control sequence, an endoribonuclease binding sequence, a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid can interact with a target nucleic acid in a sequence-specific manner via hybridization (i.e., base pairing). The nucleotide sequence of the spacer can vary depending on the sequence of the target nucleic acid of interest.

In a CRISPR/Cas system herein, the spacer sequence can be designed to hybridize to a target nucleic acid that is located 5' of a PAM of the Cas9 enzyme used in the system. The spacer can perfectly match the target sequence or can have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. In some examples, the target nucleic acid comprises at most: 5, 10, 15, 16, 17, 18, 19, 20, 21, 22, 23, 24, 25, 30 or more nucleotides. The target nucleic acid sequence can comprise 20 bases immediately 5' of the first nucleotide of the PAM. For example, in a sequence comprising 5'-NNNNNNNNNNNNNNNNNNNNNRG-3' (SEQ ID NO. 1,410,473) the target nucleic acid can comprise the sequence that corresponds to the Ns, wherein N is any nucleotide, and the underlined NRG sequence is the S. pyogenes PAM.

The spacer sequence that hybridizes to the target nucleic acid can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. The spacer sequence can comprise 19 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which can be thought of as a bulge or bulges.

The spacer sequence can be designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

A minimum CRISPR repeat sequence is a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from S. pyogenes).

A minimum CRISPR repeat sequence can comprise nucleotides that can hybridize to a minimum tracrRNA sequence in a cell. The minimum CRISPR repeat sequence and a minimum tracrRNA sequence can form a duplex, i.e. a base-paired double-stranded structure. Together, the minimum CRISPR repeat sequence and the minimum tracrRNA sequence can bind to the site-directed polypeptide. At least a part of the minimum CRISPR repeat sequence can hybridize to the minimum tracrRNA sequence. At least a part of the minimum CRISPR repeat sequence can comprise at least about 30%, about 40%, about 50%, about 60%, about 65%, about 70%, about 75%, about 80%, about 85%, about 90%, about 95%, or 100% complementary to the minimum tracrRNA sequence. At least a part of the minimum CRISPR repeat sequence can comprise at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some examples, the minimum CRISPR repeat sequence is approximately 9 nucleotides in length. The minimum CRISPR repeat sequence can be approximately 12 nucleotides in length.

The minimum CRISPR repeat sequence can be at least about 60% identical to a reference minimum CRISPR repeat sequence (e.g., wild-type crRNA from S. pyogenes) over a stretch of at least 6, 7, or 8 contiguous nucleotides. For example, the minimum CRISPR repeat sequence is at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from S. pyogenes).

A minimum tracrRNA sequence can comprise nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat bind to a site-directed polypeptide. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

Bulges

In some cases, there can be a "bulge" in the duplex between the minimum CRISPR RNA and the minimum tracrRNA. A bulge is an unpaired region of nucleotides within the duplex. A bulge can contribute to the binding of the duplex to the site-directed polypeptide. The bulge can comprise, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge can comprise an unpaired purine (e.g., adenine) on the minimum CRISPR repeat strand of the bulge. In some examples, the bulge can comprise an unpaired 5'-AAGY-3' of the minimum tracrRNA sequence strand of the bulge, where Y comprises a nucleotide that can form a wobble pairing with a nucleotide on the minimum CRISPR repeat strand.

A bulge on the minimum CRISPR repeat side of the duplex can comprise at least 1, 2, 3, 4, or 5 or more unpaired nucleotides. A bulge on the minimum CRISPR repeat side of the duplex can comprise at most 1, 2, 3, 4, or 5 or more unpaired nucleotides. A bulge on the minimum CRISPR repeat side of the duplex can comprise 1 unpaired nucleotide.

A bulge on the minimum tracrRNA sequence side of the duplex can comprise at least 1, 2, 3, 4, 5, 6, 7, 8, 9, or 10 or more unpaired nucleotides. A bulge on the minimum tracrRNA sequence side of the duplex can comprise at most 1, 2, 3, 4, 5, 6, 7, 8, 9, or 10 or more unpaired nucleotides. A bulge on a second side of the duplex (e.g., the minimum tracrRNA sequence side of the duplex) can comprise 4 unpaired nucleotides.

A bulge can comprise at least one wobble pairing. In some examples, a bulge comprises at most one wobble pairing. In some examples, a bulge can comprise at least one purine nucleotide. A bulge can comprise at least 3 purine nucleotides. A bulge sequence can comprise at least 5 purine nucleotides. A bulge sequence can comprise at least one guanine nucleotide. A bulge sequence can comprise at least one adenine nucleotide.

Hairpins

In various examples, one or more hairpins can be located 3' to the minimum tracrRNA in the 3' tracrRNA sequence.

The hairpin can start at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. The hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

The hairpin can comprise at least about 1, 2, 3, 4, 5, 6, 7, 8, 9, 10, 15, or 20 or more consecutive nucleotides. The hairpin can comprise at most about 1, 2, 3, 4, 5, 6, 7, 8, 9, 10, 15, or more consecutive nucleotides.

The hairpin can comprise a CC dinucleotide (i.e., two consecutive cytosine nucleotides).

The hairpin can comprise duplexed nucleotides (e.g., nucleotides in a hairpin, hybridized together). For example, a hairpin can comprise a CC dinucleotide that is hybridized to a GG dinucleotide in a hairpin duplex of the 3' tracrRNA sequence.

One or more of the hairpins can interact with guide RNA-interacting regions of a site-directed polypeptide.

In some examples, there are two or more hairpins, and in other examples there are three or more hairpins.

3' tracrRNA Sequence

A 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

The 3' tracrRNA sequence can have a length from about 6 nucleotides to about 100 nucleotides. For example, the 3' tracrRNA sequence can have a length from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The 3' tracrRNA sequence can have a length of approximately 14 nucleotides.

The 3' tracrRNA sequence can be at least about 60% identical to a reference 3' tracrRNA sequence (e.g., wild type 3' tracrRNA sequence from *S. pyogenes*) over a stretch of at least 6, 7, or 8 contiguous nucleotides. For example, the 3' tracrRNA sequence can be at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from *S. pyogenes*) over a stretch of at least 6, 7, or 8 contiguous nucleotides.

The 3' tracrRNA sequence can comprise more than one duplexed region (e.g., hairpin, hybridized region). The 3' tracrRNA sequence can comprise two duplexed regions.

The 3' tracrRNA sequence can comprise a stem loop structure. The stem loop structure in the 3' tracrRNA can comprise at least 1, 2, 3, 4, 5, 6, 7, 8, 9, 10, 15 or 20 or more nucleotides. The stem loop structure in the 3' tracrRNA can comprise at most 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, or an exon. The stem loop structure can comprise at least about 1, 2, 3, 4, or 5 or more functional moieties. The stem loop structure can comprise at most about 1, 2, 3, 4, or 5 or more functional moieties.

The hairpin in the 3' tracrRNA sequence can comprise a P-domain. In some examples, the P-domain can comprise a double-stranded region in the hairpin.

tracrRNA Extension Sequence

A tracrRNA extension sequence can be provided whether the tracrRNA is in the context of single-molecule guides or double-molecule guides. The tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. The tracrRNA extension sequence can have a length from about 20 to about 5000 or more nucleotides. The tracrRNA extension sequence can have a length of more than 1000 nucleotides. The tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. The tracrRNA extension sequence can have a length of less than 1000 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. The functional moiety can function in a eukaryotic cell. The functional moiety can function in a prokaryotic cell. The functional moiety can function in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, or a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). The tracrRNA extension sequence can comprise a primer binding site or a molecular index (e.g., barcode sequence). The tracrRNA extension sequence can comprise one or more affinity tags.

Single-Molecule Guide Linker Sequence

The linker sequence of a single-molecule guide nucleic acid can have a length from about 3 nucleotides to about 100 nucleotides. In Jinek et al., supra, for example, a simple 4 nucleotide "tetraloop" (-GAAA-) was used, Science, 337 (6096):816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337 (6096):816-821 (2012), but numerous other sequences, including longer sequences can likewise be used.

The linker sequence can comprise a functional moiety. For example, the linker sequence can one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

Genome Engineering Strategies to Correct Cells by Deletion (Excision), Insertion, or Replacement (Deletion and Insertion) of One or More Exons or Aberrant Intronic Splice Acceptor or Donor Sites A step of the ex vivo methods of the present disclosure involves editing/correcting the DMD patient specific iPS cells using genome engineering. Likewise, a step of the in vivo methods of the present disclosure involves editing/correcting the muscle cells in a DMD patient using genome engineering. Similarly, a step in the cellular methods of the present disclosure involves editing/correcting the dystrophin gene in a human cell by genome engineering.

DMD patients exhibit a wide range of mutations in the dystrophin gene. Therefore, different patients will generally require different correction strategies. Any CRISPR endonuclease can be used in the methods of the present disclosure, each CRISPR endonuclease having its own associated PAM, which may or may not be disease specific. For example, gRNA spacer sequences for targeting the dystrophin gene with a CRISPR/Cas9 endonuclease from *S. pyogenes* have been identified in SEQ ID NOs: 1-467,030 and 1,410,430-1,410,472 of the Sequence Listing. gRNA spacer sequences for targeting the dystrophin gene with a CRISPR/Cas9 endonuclease from *S. aureus* have been identified in SEQ ID NOs: 467,031-528,196 of the Sequence Listing. gRNA spacer sequences for targeting the dystrophin gene with a CRISPR/Cas9 endonuclease from *S. thermophilus* have been identified in SEQ ID NOs: 528,197-553,198 of the Sequence Listing. gRNA spacer sequences for targeting the dystrophin gene with a CRISPR/Cas9 endonuclease from *T. denticola* have been identified in SEQ ID NOs: 553,199-563,911 of the Sequence Listing. gRNA spacer sequences for targeting the dystrophin gene with a CRISPR/Cas9 endonuclease from *N. meningitides* have been identified in SEQ ID NOs: 563,912-627,854 and 1,410,400-1,410,402 of the Sequence Listing. gRNA spacer sequences for targeting the dystrophin gene with a CRISPR/Cpf1 endonuclease from *Acidominoccoccus*, Lachnospiraceae and *Franciscella Novicida* have been identified in SEQ ID NOs: 627,855-1,410,399 and 1,410,403-1,410,429 of the Sequence Listing.

One genome engineering strategy involves exon deletion. Targeted deletion of specific exons can be an attractive strategy for treating a large subset of patients with a single therapeutic cocktail. It is predicted that single exon deletions can treat up to 13% of patients, while a multi-exon deletion can treat up to 62% of patients by restoring the dystrophin reading frame. While multi-exon deletions can reach a larger number of patients, for larger deletions the efficiency of deletion greatly decreases with increased size. Therefore, preferred deletions can range from 400 to 350,000 base pairs (bp) in size. For example, deletions can range from 400-1,000; 1,000-5,000; 5,000-10,000, 10,000-25,000; 25,000-50,000, 50,000-100,000; 100,000-200,000; or 200,000-350,000 base pairs in size.

As stated previously, the DMD gene contains 79 exons. Any one or more of the 79 exons, or aberrant intronic splice acceptor or donor sites, can be deleted in order to restore the dystrophin reading frame. The methods provide gRNA pairs that can be used to delete exons 2, 8, 43, 44, 45, 46, 50, 51, 52, 53, 70, 45-53, or 45-55, as these are the regions that are predicted to reach the largest subset of patients (see Tables 1 and 2; Table 2 percentages given are the average reported from the literature).

Different regions of the DMD gene can be repaired by either deletion and/or HDR. Certain combinations of gRNAs that cut within the genomic region of interest can be used to correct mutations in the targeted exon. Coordinates are based on the GRch38/hg38 genomic assembly (Table 1).

TABLE 1

| Targeted Exon(s) | Repair strategy | Genomic Coordinates |
| --- | --- | --- |
| 45-55 | Deletion and/or HDR | Chrx: 31512453-32216916 |
| 45-53 | Deletion and/or HDR | Chrx: 31679586-32216916 |
| 2 | Deletion and/or HDR | Chrx: 32849820-33211282 |
| 8 | Deletion and/or HDR | Chrx: 32697998-32809493 |
| 43 | Deletion and/or HDR | Chrx: 32217063-32310082 |

TABLE 1-continued

| Targeted Exon(s) | Repair strategy | Genomic Coordinates |
| --- | --- | --- |
| 44 | Deletion and/or HDR | Chrx: 31968514-32287529 |
| 45 | Deletion and/or HDR | Chrx: 31932227-32216916 |
| 46 | Deletion and/or HDR | Chrx: 31929745-31968339 |
| 50 | Deletion and/or HDR | Chrx: 31774192-31836718 |
| 51 | Deletion and/or HDR | Chrx: 31729748-31819975 |
| 52 | Deletion and/or HDR | Chrx: 31679586-31773960 |
| 53 | Deletion and/or HDR | Chrx: 31658144-31729631 |
| 70 | HDR | Chrx: 31177970-31180370 |

TABLE 2

| Deleted Exon(s) | % of Mutations | Citation |
| --- | --- | --- |
| 45-55 | 62.1 | Beroud, C., et al., Hum Mutat, 2007. 28(2): p. 196-202. |
| 45-53 | 53.3 | Tuffery-Giraud, S., et al., Hum Mutat, 2009. 30(6): p. 934-45. |
| 2 | 1.9 | Aartsma-Rus, A., et al., Hum Mutat, 2009. 30(3): p. 293-9. |
| 8 | 2.2 | Aartsma-Rus, A., et al., Id. Bladen, C. L., et al., Hum Mutat, 2015. 36(4): p. 395-402. |
| 43 | 5.7 | Aartsma-Rus, A., et al., Id. Bladen, C. L., et al., Id. |
| 44 | 6.7 | Aartsma-Rus, A., et al., Id. Bladen, C. L., et al., Id. |
| 45 | 8.6 | Aartsma-Rus, A., et al., Id. Bladen, C. L., et al., Id. |
| 46 | 4.5 | Aartsma-Rus, A., et al., Id. Bladen, C. L., et al., Id. |
| 50 | 3.9 | Aartsma-Rus, A., et al., Id. Bladen, C. L., et al., Id. |
| 51 | 13.5 | Aartsma-Rus, A., et al., Id. Bladen, C. L., et al., Id. |
| 52 | 3.9 | Aartsma-Rus, A., et al., Id. Bladen, C. L., et al., Id. |
| 53 | 8.9 | Aartsma-Rus, A., et al., Id. Bladen, C. L., et al., Id. |

The methods provide gRNA pairs that delete exon 2 by cutting the gene twice, one gRNA cutting at the 5' end of exon 2 and the other gRNA cutting at the 3' end of exon 2.

The methods provide gRNA pairs that delete exon 8 by cutting the gene twice, one gRNA cutting at the 5' end of exon 8 and the other gRNA cutting at the 3' end of exon 8.

The methods provide gRNA pairs that delete exon 43 by cutting the gene twice, one gRNA cutting at the 5' end of exon 43 and the other gRNA cutting at the 3' end of exon 43.

The methods provide gRNA pairs that delete exon 44 by cutting the gene twice, one gRNA cutting at the 5' end of exon 44 and the other gRNA cutting at the 3' end of exon 44.

The methods provide gRNA pairs that delete exon 45 by cutting the gene twice, one gRNA cutting at the 5' end of exon 45 and the other gRNA cutting at the 3' end of exon 45.

The methods provide gRNA pairs that delete exon 46 by cutting the gene twice, one gRNA cutting at the 5' end of exon 46 and the other gRNA cutting at the 3' end of exon 46.

The methods provide gRNA pairs that delete exon 50 by cutting the gene twice, one gRNA cutting at the 5' end of exon 50 and the other gRNA cutting at the 3' end of exon 50.

The methods provide gRNA pairs that delete exon 51 by cutting the gene twice, one gRNA cutting at the 5' end of exon 51 and the other gRNA cutting at the 3' end of exon 51.

The methods provide gRNA pairs that delete exon 52 by cutting the gene twice, one gRNA cutting at the 5' end of exon 52 and the other gRNA cutting at the 3' end of exon 52.

The methods provide gRNA pairs that delete exon 53 by cutting the gene twice, one gRNA cutting at the 5' end of exon 53 and the other gRNA cutting at the 3' end of exon 53.

The methods provide gRNA pairs that delete exon 70 by cutting the gene twice, one gRNA cutting at the 5' end of exon 70 and the other gRNA cutting at the 3' end of exon 70.

The methods provide gRNA pairs that delete exons 45-53 by cutting the gene twice, one gRNA cutting at the 5' end of exon 45 and the other gRNA cutting at the 3' end of exon 53.

The methods provide gRNA pairs that delete exons 45-55 by cutting the gene twice, one gRNA cutting at the 5' end of exon 45 and the other gRNA cutting at the 3' end of exon 55.

Another genome engineering strategy involves insertion or replacement of one or more exons or aberrant intronic splice acceptor or donor sites by homology directed repair (HDR), which is also known as homologous recombination (HR). Homology directed repair is one strategy for treating patients that have premature stop codons due to small insertions/deletions or point mutations. Rather than making a large genomic deletion that will convert a DMD phenotype to a BMD phenotype, this strategy will restore the entire reading frame and completely reverse the diseased state. This strategy will require a more custom approach based on the location of the patient's premature stop. Most of the dystrophin exons are small (<300 bp). This is advantageous, as HDR efficiencies are inversely related to the size of the donor molecule. Also, it is expected that the donor templates can fit into size constrained adeno-associated virus (AAV) molecules, which have been shown to be an effective means of donor template delivery.

Homology direct repair is a cellular mechanism for repairing double-stranded breaks (DSBs). The most common form is homologous recombination. There are additional pathways for HDR, including single-strand annealing and alternative-HDR. Genome engineering tools allow researchers to manipulate the cellular homologous recombination pathways to create site-specific modifications to the genome. It has been found that cells can repair a double-stranded break using a synthetic donor molecule provided in trans. Therefore, by introducing a double-stranded break near a specific mutation and providing a suitable donor, targeted changes can be made in the genome. Specific cleavage increases the rate of HDR more than 1,000 fold above the rate of 1 in $10^6$ cells receiving a homologous donor alone. The rate of homology directed repair (HDR) at a particular nucleotide is a function of the distance to the cut site, so choosing overlapping or nearest target sites is important. Gene editing offers the advantage over gene addition, as correcting in situ leaves the rest of the genome unperturbed.

Supplied donors for editing by HDR vary markedly but can contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors have been used. These oligonucleotides can range in size from less than 100 nt to over 200 nt, though longer ssDNA can also be generated and used. Double-stranded donors can be used, including PCR amplicons, plasmids, and mini-circles. In general, it has been found that an AAV vector can be a very effective means of delivery of a donor template, though the packaging limits for individual donors is <5 kb. Active transcription of the donor increased HDR three-fold, indicating the inclusion of promoter can increase conversion. Conversely, CpG methylation of the donor decreased gene expression and HDR.

In addition to wildtype endonucleases, such as Cas9, nickase variants exist that can have one or the other nuclease domain inactivated resulting in cutting of only one DNA strand. HDR can be directed from individual Cas nickases or using pairs of nickases that flank the target area. Donors can be single-stranded, nicked, or dsDNA.

The donor DNA can be supplied with the nuclease or independently by a variety of different methods, for example by transfection, nano-particle, micro-injection, or viral transduction. A range of tethering options has been proposed to increase the availability of the donors for HDR. Examples include attaching the donor to the nuclease, attaching to DNA binding proteins that bind nearby, or attaching to proteins that are involved in DNA end binding or repair.

The repair pathway choice can be guided by a number of culture conditions, such as those that influence cell cycling, or by targeting of DNA repair and associated proteins. For example, to increase HDR, key NHEJ molecules can be suppressed, such as KU70, KU80 or DNA ligase IV.

Without a donor present, the ends from a DNA break or ends from different breaks can be joined using the several nonhomologous repair pathways in which the DNA ends are joined with little or no base-pairing at the junction. In addition to canonical NHEJ, there are similar repair mechanisms, such as alt-NHEJ. If there are two breaks, the intervening segment can be deleted or inverted. NHEJ repair pathways can lead to insertions, deletions, or mutations at the joints.

NHEJ was used to insert a 15-kb inducible gene expression cassette into a defined locus in human cell lines after nuclease cleavage. Maresca, M., Lin, V. G., Guo, N. & Yang, Y. Obligate ligation-gated recombination (ObLiGaRe): custom-designed nuclease-mediated targeted integration through nonhomologous end joining. *Genome Res* 23, 539-546 (2013).

In addition to genome editing by NHEJ or HDR, site-specific gene insertions have been conducted that use both the NHEJ pathway and HR. A combination approach can be applicable in certain settings, possibly including intron/exon borders. NHEJ can prove effective for ligation in the intron, while the error-free HDR can be better suited in the coding region.

As stated previously, the DMD gene contains 79 exons. Any one or more of the 79 exons can be repaired in order to correct a mutation and restore the dystrophin reading frame. Some methods provide one gRNA or a pair of gRNAs that can be used to facilitate incorporation of a new sequence from a polynucleotide donor template to insert or replace a sequence in exon 70, as data shows that exon 70 can be prone to the most premature stop codons in the dystrophin gene (Tuffery-Giraud, S., et al., Hum Mutat, 2009. 30(6): p. 934-45) (Flanigan, K. M., et al., Hum Mutat, 2009. 30(12): p. 1657-66). In order to make the method applicable to the largest number of patients, the method involves a donor template that can insert or replace the whole exon 70. Alternatively, the methods provide one gRNA or a pair of gRNAs that can be used to facilitate incorporation of a new sequence from a polynucleotide donor template to insert or replace a sequence in exon 2, exon 8, exon 43, exon 44, exon 45, exon 46, exon 50, exon 51, exon 52, exon 53, or exon 70. See Table 1.

In order to ensure that the pre-mRNA is properly processed following HDR, it is important to keep the surrounding splicing signals intact. Splicing donor and acceptors can be generally within 100 base pairs of the neighboring intron. Therefore, in some examples, methods can provide all gRNAs that cut approximately +/−0-3100 bp with respect to the exon's intron junctions.

Some methods provide gRNA pairs that make a deletion by cutting the gene twice, one gRNA cutting at the 5' end of exon 2 and the other gRNA cutting at the 3' end of exon 2 that facilitates incorporation of a new sequence from a polynucleotide donor template to replace a sequence in exon 2.

Alternatively, some methods provide one gRNA from the preceding paragraph to make one double-strand cut that facilitates insertion of a new sequence from a polynucleotide donor template to replace a sequence in exon 2.

Some examples of the methods provide gRNA pairs that make a deletion by cutting the gene twice, one gRNA cutting at the 5' end of exon 8 and the other gRNA cutting at the 3' end of exon 8 that facilitates incorporation of a new sequence from a polynucleotide donor template to replace a sequence in exon 8.

Alternatively, some methods provide one gRNA from the preceding paragraph to make one double-strand cut that facilitates insertion of a new sequence from a polynucleotide donor template to replace a sequence in exon 8.

Some methods provide gRNA pairs that make a deletion by cutting the gene twice, one gRNA cutting at the 5' end of exon 43 and the other gRNA cutting at the 3' end of exon 43 that facilitates incorporation of a new sequence from a polynucleotide donor template to replace a sequence in exon 43.

Alternatively, some methods provide one gRNA from the preceding paragraph to make one double-strand cut that facilitates insertion of a new sequence from a polynucleotide donor template to replace a sequence in exon 43.

Some methods provide gRNA pairs that make a deletion by cutting the gene twice, one gRNA cutting at the 5' end of exon 44 and the other gRNA cutting at the 3' end of exon 44 that facilitates incorporation of a new sequence from a polynucleotide donor template to replace a sequence in exon 44.

Alternatively, some methods provide one gRNA from the preceding paragraph to make one double-strand cut that facilitates insertion of a new sequence from a polynucleotide donor template to replace a sequence in exon 44.

Some methods provide gRNA pairs that make a deletion by cutting the gene twice, one gRNA cutting at the 5' end of exon 45 and the other gRNA cutting at the 3' end of exon 45 that facilitates incorporation of a new sequence from a polynucleotide donor template to replace a sequence in exon 45.

Alternatively, some methods provide one gRNA from the preceding paragraph to make one double-strand cut that facilitates insertion of a new sequence from a polynucleotide donor template to replace a sequence in exon 45.

Some methods provide gRNA pairs that make a deletion by cutting the gene twice, one gRNA cutting at the 5' end of exon 46 and the other gRNA cutting at the 3' end of exon 46 that facilitates incorporation of a new sequence from a polynucleotide donor template to replace a sequence in exon 46.

Alternatively, some methods provide one gRNA from the preceding paragraph to make one double-strand cut that facilitates insertion of a new sequence from a polynucleotide donor template to replace a sequence in exon 46.

Some methods provide gRNA pairs that make a deletion by cutting the gene twice, one gRNA cutting at the 5' end of exon 50 and the other gRNA cutting at the 3' end of exon 50 that facilitates incorporation of a new sequence from a polynucleotide donor template to replace a sequence in exon 50.

Alternatively, some methods provide one gRNA from the preceding paragraph to make one double-strand cut that facilitates insertion of a new sequence from a polynucleotide donor template to replace a sequence in exon 50.

Some methods provide gRNA pairs that make a deletion by cutting the gene twice, one gRNA cutting at the 5' end of exon 51 and the other gRNA cutting at the 3' end of exon 51 that facilitates incorporation of a new sequence from a polynucleotide donor template to replace a sequence in exon 51.

Alternatively, some methods provide one gRNA from the preceding paragraph to make one double-strand cut that facilitates insertion of a new sequence from a polynucleotide donor template to replace a sequence in exon 51.

Some methods provide gRNA pairs that make a deletion by cutting the gene twice, one gRNA cutting at the 5' end of exon 52 and the other gRNA cutting at the 3' end of exon 52 that facilitates incorporation of a new sequence from a polynucleotide donor template to replace a sequence in exon 52.

Alternatively, some methods provide one gRNA from the preceding paragraph to make one double-strand cut that facilitates insertion of a new sequence from a polynucleotide donor template to replace a sequence in exon 52.

Some methods provide gRNA pairs that make a deletion by cutting the gene twice, one gRNA cutting at the 5' end of exon 53 and the other gRNA cutting at the 3' end of exon 53 that facilitates incorporation of a new sequence from a polynucleotide donor template to replace a sequence in exon 53.

Alternatively, some methods provide one gRNA from the preceding paragraph to make one double-strand cut that facilitates insertion of a new sequence from a polynucleotide donor template to replace a sequence in exon 53.

Some methods provide gRNA pairs that make a deletion by cutting the gene twice, one gRNA cutting at the 5' end of exon 70 and the other gRNA cutting at the 3' end of exon 70 that facilitates incorporation of a new sequence from a polynucleotide donor template to replace a sequence in exon 70.

Alternatively, some methods provide one gRNA from the preceding paragraph to make one double-strand cut that facilitates insertion of a new sequence from a polynucleotide donor template to replace a sequence in exon 70.

In addition to single exon replacements by homology directed repair, we also describe methods for conducting a partial cDNA knock-in of mutational hotspots found in the DMD gene. For example, a treatment that repairs exons 45-55 can treat up to 62% of patients. Rather than deleting or replacing exons 45-55 as described herein, another treatment option replaces entire genomic region for exons 45-55—which, including introns, spans >350,000 bp—with a cDNA containing only the coding region of exons 45-55, which spans approximate 1800 bp. The replacement could be effected using a homology directed repair approach. By excluding the intergenic regions, the cDNA for exons 45-55 can more easily be accommodated (than the entire genomic region) along with homology arms into any donor vector described in the section of this application titled Nucleic Acids Encoding System Components. In this approach, two gRNAs and Cas9 or Cpf1 that remove the genomic region from exon 45-55 can be delivered along with a donor construct to replace the deleted region with the desired cDNA knock-in.

The cDNA knock-in approach can be used to replace any series of exons.

The cDNA knock-in sequence can be optimized to contain synthetic intron sequences. Synthetic introns which are smaller than naturally occurring introns can be added between the exons in the donor construct to ensure proper expression and processing of the DMD locus.

Illustrative modifications within the dystrophin gene include deletions, insertions, or replacements within or proximal to the dystrophin loci referred to above, such as within the region of less than 3 kb, less than 2 kb, less than 1 kb, less than 0.5 kb upstream or downstream of the specific exon. Given the relatively wide variations of mutations in the dystrophin gene, it will be appreciated that numerous variations of the deletions, insertions, or replacements referenced above (including without limitation larger as well as smaller deletions), would be expected to result in restoration of the dystrophin reading frame and restoration of the dystrophin protein activity.

Such variants can include deletions, insertions, or replacements that are larger in the 5' and/or 3' direction than the specific exon in question, or smaller in either direction. Accordingly, by "near" or "proximal" with respect to specific exon deletions, insertions or replacements, it is intended that the SSB or DSB locus associated with a desired deletion, insertion, or replacement boundary (also referred to herein as an endpoint) can be within a region that is less than about 3 kb from the reference locus noted. The SSB or DSB locus can be more proximal and within 2 kb, within 1 kb, within 0.5 kb, or within 0.1 kb. In the case of small deletions, the desired endpoint can be at or "adjacent to" the reference locus, by which it is intended that the endpoint can be within 100 bp, within 50 bp, within 25 bp, or less than about 10 bp to 5 bp from the reference locus.

One advantage for patients with DMD of replicating or mimicking the product produced by exon skipping and/or restoring the reading frame is that it is already known to be both safe and associated with the amelioration of DMD. Other examples comprising larger or smaller deletions/insertions/replacements can be expected to provide the same benefit, as long as the dystrophin reading frame is restored. Thus, it can be expected that many variations of the deletions, insertions, and replacements described and illustrated herein can be effective for ameliorating DMD.

Target Sequence Selection

Shifts in the location of the 5' boundary and/or the 3' boundary relative to particular reference loci can be used to facilitate or enhance particular applications of gene editing, which depend in part on the endonuclease system selected for the editing, as further described and illustrated herein.

In a first nonlimiting example of such target sequence selection, many endonuclease systems have rules or criteria that can guide the initial selection of potential target sites for cleavage, such as the requirement of a PAM sequence motif in a particular position adjacent to the DNA cleavage sites in the case of CRISPR Type II or Type V endonucleases.

In another nonlimiting example of target sequence selection or optimization, the frequency of "off-target" activity for a particular combination of target sequence and gene editing endonuclease (i.e. the frequency of DSBs occurring at sites other than the selected target sequence) can be assessed relative to the frequency of on-target activity. In some cases, cells that have been correctly edited at the desired locus can have a selective advantage relative to other cells. Illustrative, but nonlimiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the correction. In some cases, cells can be edited two or more times in order to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

Whether any selective advantage is applicable or any directed selection is to be applied in a particular case, target sequence selection can also be guided by consideration of off-target frequencies in order to enhance the effectiveness of the application and/or reduce the potential for undesired alterations at sites other than the desired target. As described further and illustrated herein and in the art, the occurrence of off-target activity can be influenced by a number of factors including similarities and dissimilarities between the target site and various off target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical inducers). Many such inducers cause DSBs to occur indiscriminately in the genome, and DSBs can be regularly induced and repaired in normal cells. During repair, the original sequence can be reconstructed with complete fidelity, however, in some cases, small insertions or deletions (referred to as "indels") are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can comprise as few as ten basepairs or less, can also be used to bring about desired deletions. For example, a single DSB can be introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which may or may not be desired given the particular circumstances.

The examples provided herein further illustrate the selection of various target regions for the creation of DSBs designed to induce disruptions, deletions, or replacements that result in restoration of the dystrophin reading frame, as well as the selection of specific target sequences within such regions that are designed to minimize off-target events relative to on-target events.

Nucleic Acid Modifications

In some cases, polynucleotides introduced into cells can comprise one or more modifications that can be used, individually or in combination, for example, to enhance activity, stability or specificity, alter delivery, reduce innate immune responses in host cells, or for other enhancements, as further described herein and known in the art.

In certain examples, modified polynucleotides can be used in the CRISPR/Cas9/Cpf1 system, in which case the guide RNAs (either single-molecule guides or double-molecule guides) and/or a DNA or an RNA encoding a Cas or Cpf1 endonuclease introduced into a cell can be modified, as described and illustrated below. Such modified polynucleotides can be used in the CRISPR/Cas9/Cpf1 system to edit any one or more genomic loci.

Using the CRISPR/Cas9/Cpf1 system for purposes of nonlimiting illustrations of such uses, modifications of guide RNAs can be used to enhance the formation or stability of the CRISPR/Cas9/Cpf1 genome editing complex comprising guide RNAs, which can be single-molecule guides or double-molecule, and a Cas or Cpf1 endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in aspects in which a Cas or Cpf1 endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of CRISPR/Cas9/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC), which avoids the use of gels such as PAGE) tends to become more challenging as polynucleotide lengths increase significantly beyond a hundred or so nucleotides. One approach that can be used for generating chemically-modified RNAs of greater length is to produce two or more molecules that are ligated together. Much longer RNAs, such as those encoding a Cas9 endonuclease, are more readily generated enzymatically. While fewer types of modifications are available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar, in some aspects a 2'-O-alkyl, 2'-O-alkyl-O-alkyl, or 2'-fluoro-modified nucleotide. In some aspects, RNA modifications can comprise 2'-fluoro, 2'-amino or 2' O-methyl modifications on the ribose of pyrimidines, abasic residues, or an inverted base at the 3' end of the RNA. Such modifications can be routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly CH2-NH—O—CH2, CH, ~N(CH3)~O~CH2 (known as a methylene(methylimino) or MMI backbone), CH2-O—N(CH3)-CH2, CH2-N(CH3)-N(CH3)-CH2 and O—N(CH3)-CH2-CH2 backbones, wherein the native phosphodiester backbone is represented as O—P—O—

CH,); amide backbones [see De Mesmaeker et al., Acc. Chem. Res., 28:366-374 (1995)]; morpholino backbone structures (see Summerton and Weller, U.S. Pat. No. 5,034, 506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad. Sci., 97: 9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH2 component parts; see U.S. Pat. Nos. 5,034,506; 5,166,315; 5,185, 444; 5,214,134; 5,216,141; 5,235,033; 5,264,562; 5,264, 564; 5,405,938; 5,434,257; 5,466,677; 5,470,967; 5,489, 677; 5,541,307; 5,561,225; 5,596,086; 5,602,240; 5,610, 289; 5,602,240; 5,608,046; 5,610,289; 5,618,704; 5,623, 070; 5,663,312; 5,633,360; 5,677,437; and 5,677,439, each of which is herein incorporated by reference.

One or more substituted sugar moieties can also be included, e.g., one of the following at the 2' position: OH, SH, SCH3, F, OCN, OCH3 OCH3, OCH3O(CH2)n CH3, O(CH2)n NH2, or O(CH2)n CH3, where n is from 1 to about 10; C1 to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-O-CH2CH2OCH3, also known as 2'-O-(2-methoxyethyl)) (Martin et al, Helv. Chim. Acta, 1995, 78, 486). Other modifications include 2'-methoxy (2'-O-CH3), 2'-propoxy (2'-OCH2 CH2CH3) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some examples, both a sugar and an internucleoside linkage, i.e., the backbone, of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone. The nucleobases can be retained and bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719, 262. Further teaching of PNA compounds can be found in Nielsen et al, Science, 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are aspects of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and US Patent Application Publication 2003/0158403.

Thus, the term "modified" refers to a non-natural sugar, phosphate, or base that is incorporated into a guide RNA, an endonuclease, or both a guide RNA and an endonuclease. It is not necessary for all positions in a given oligonucleotide to be uniformly modified, and in fact more than one of the aforementioned modifications can be incorporated in a single oligonucleotide, or even in a single nucleoside within an oligonucleotide.

The guide RNAs and/or mRNA (or DNA) encoding an endonuclease can be chemically linked to one or more moieties or conjugates that enhance the activity, cellular distribution, or cellular uptake of the oligonucleotide. Such moieties comprise, but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med. Chem. Let., 4: 1053-1060 (1994)]; a thioether, e.g., hexyl-S-tritylthiol [Manoharan et al, Ann. N. Y. Acad. Sci., 660: 306-309 (1992) and Manoharan et al., Bioorg. Med. Chem. Let., 3: 2765-2770 (1993)]; a thiocholesterol [Oberhauser et al., Nucl. Acids Res., 20: 533-538 (1992)]; an aliphatic chain, e.g., dodecandiol or undecyl residues [Kabanov et al., FEBS Lett., 259: 327-330 (1990) and Svinarchuk et al., Biochimie, 75: 49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36: 3651-3654 (1995) and Shea et al., Nucl. Acids Res., 18: 3777-3783 (1990)]; a polyamine or a polyethylene glycol chain [Mancharan et al., Nucleosides & Nucleotides, 14: 969-973 (1995)]; adamantane acetic acid [Manoharan et al., Tetrahedron Lett., 36: 3651-3654 (1995)]; a palmityl moiety [(Mishra et al., Biochim. Biophys. Acta, 1264: 229-237 (1995)]; or an octadecylamine or hexylamino-carbonyl-t oxycholesterol moiety [Crooke et al., J. Pharmacol. Exp. Ther., 277: 923-937 (1996)]. See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21(10):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups, such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6(4): 440-468 (2013); Kanasty et al., Molecular Therapy 20(3): 513-524 (2012); Burnett et al., Biotechnol J. 6(9):1130-46 (2011); Judge and MacLachlan, Hum Gene Ther 19(2):111-24 (2008); and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2: 77-96 (2011); Gaglione and Messere, Mini Rev Med Chem, 10(7):578-95 (2010); Chernolovskaya et al, Curr Opin Mol Ther., 12(2):158-67 (2010); Deleavey et al., Curr Protoc Nucleic Acid Chem Chapter 16:Unit 16.3 (2009); Behlke, Oligonucleotides 18(4):305-19 (2008); Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013), and references cited therein.

Codon-Optimization

A polynucleotide encoding a site-directed polypeptide can be codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid guides the site-directed polypeptide to a target nucleic acid.

RNPs

The site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP).

Nucleic Acids Encoding System Components

The present disclosure provides a nucleic acid comprising a nucleotide sequence encoding a genome-targeting nucleic acid of the disclosure, a site-directed polypeptide of the disclosure, and/or any nucleic acid or proteinaceous molecule necessary to carry out the aspects of the methods of the disclosure.

The nucleic acid encoding a genome-targeting nucleic acid of the disclosure, a site-directed polypeptide of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3, which are described in FIGS. 1A to 1C. Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., *Molecular Therapy—Nucleic Acids* 3, e161 (2014) doi:10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

The nucleic acid encoding a genome-targeting nucleic acid of the disclosure and/or a site-directed polypeptide can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. A variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Delivery

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

Polynucleotides, such as guide RNA, sgRNA, and mRNA encoding an endonuclease, can be delivered to a cell or a patient by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs can also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

As stated previously, the site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP).

RNA is capable of forming specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

The endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be combined in a 1:1 molar ratio. Alternatively, the endonuclease, crRNA and tracrRNA can be generally combined in a 1:1:1 molar ratio. However, a wide range of molar ratios can be used to produce a RNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, international patent application publication number WO 01/83692. See Table 3.

TABLE 3

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |

TABLE 3-continued

| AAV Serotype | Genbank Accession No. |
| --- | --- |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others. See Table 4.

TABLE 4

| Tissue/Cell Type | Serotype |
| --- | --- |
| Liver | AAV8, AAV3, AAV5, AAV9 |
| Skeletal muscle | AAV1, AAV7, AAV6, AAV8, AAV9 |
| Central nervous system | AAV5, AAV1, AAV4 |
| RPE | AAV5, AAV4 |
| Photoreceptor cells | AAV5 |
| Lung | AAV9 |
| Heart | AAV8 |
| Pancreas | AAV8 |
| Kidney | AAV2 |

Genetically Modified Cells

The term "genetically modified cell" refers to a cell that comprises at least one genetic modification introduced by genome editing (e.g., using the CRISPR/Cas system). In some ex vivo examples herein, the genetically modified cell can be a genetically modified progenitor cell. In some in vivo examples herein, the genetically modified cell can be a genetically modified muscle cell or genetically modified muscle pre-cursor cell. A genetically modified cell comprising an exogenous genome-targeting nucleic acid and/or an exogenous nucleic acid encoding a genome-targeting nucleic acid is contemplated herein.

The term "control treated population" describes a population of cells that has been treated with identical media, viral induction, nucleic acid sequences, temperature, confluency, flask size, pH, etc., with the exception of the addition of the genome editing components. Any method known in the art can be used to measure restoration of the dystrophin reading frame, for example, Western Blot analysis of the dystrophin protein or quantifying dystrophin mRNA.

The term "isolated cell" refers to a cell that has been removed from an organism in which it was originally found, or a descendant of such a cell. Optionally, the cell can be cultured in vitro, e.g., under defined conditions or in the presence of other cells. Optionally, the cell can be later introduced into a second organism or re-introduced into the organism from which it (or the cell from which it is descended) was isolated.

The term "isolated population" with respect to an isolated population of cells refers to a population of cells that has been removed and separated from a mixed or heterogeneous population of cells. In some cases, the isolated population can be a substantially pure population of cells, as compared to the heterogeneous population from which the cells were isolated or enriched. In some cases, the isolated population can be an isolated population of human progenitor cells, e.g., a substantially pure population of human progenitor cells, as compared to a heterogeneous population of cells comprising human progenitor cells and cells from which the human progenitor cells were derived.

The term "substantially enhanced," with respect to a particular cell population, refers to a population of cells in which the occurrence of a particular type of cell is increased relative to pre-existing or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating DMD.

The term "substantially enriched" with respect to a particular cell population, refers to a population of cells that is at least about 10%, about 20%, about 30%, about 40%, about 50%, about 60%, about 70% or more with respect to the cells making up a total cell population.

The term "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of progenitor cells, refers to a population of cells that contain fewer than about 20%, about 15%, about 10%, about 9%, about 8%, about 7%, about 6%, about 5%, about 4%, about 3%, about 2%, about 1%, or less than 1%, of cells that are not progenitor cells as defined by the terms herein.

Differentiation of Corrected iPSCs into Pax7+ Muscle Progenitor Cells

Another step of the ex vivo methods of the present disclosure involves differentiating the corrected iPSCs into Pax7+ muscle progenitor cells. The differentiating step can be performed according to any method known in the art. For example, the differentiating step can comprise contacting the genome-edited iPSC with specific media formulations, including small molecule drugs, to differentiate it into a Pax7+ muscle progenitor cell, as shown in Chal, Oginuma et al. 2015. Alternatively, iPSCs, myogenic progenitors, and cells of other lineages can be differentiated into muscle using any one of a number of established methods that involve transgene over expression, serum withdrawal, and/or small molecule drugs, as shown in the methods of Tapscott, Davis et al. 1988, Langen, Schols et al. 2003, Fujita, Endo et al. 2010, Xu, Tabebordbar et al. 2013, Shoji, Woltjen et al. 2015.

Implanting Pax7+ Muscle Progenitor Cells into Patients

Another step of the ex vivo methods of the invention involves implanting the Pax7+ muscle progenitor cells into patients. This implanting step can be accomplished using any method of implantation known in the art. For example, the genetically modified cells can be injected directly in the patient's muscle.

Pharmaceutically Acceptable Carriers

The ex vivo methods of administering progenitor cells to a subject contemplated herein involve the use of therapeutic compositions comprising progenitor cells.

Therapeutic compositions can contain a physiologically tolerable carrier together with the cell composition, and optionally at least one additional bioactive agent as described herein, dissolved or dispersed therein as an active ingredient. In some cases, the therapeutic composition is not substantially immunogenic when administered to a mammal or human patient for therapeutic purposes, unless so desired.

In general, the progenitor cells described herein can be administered as a suspension with a pharmaceutically acceptable carrier. One of skill in the art can recognize that a pharmaceutically acceptable carrier to be used in a cell composition can not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

Administration & Efficacy

The terms "administering," "introducing" and "transplanting" are used interchangeably in the context of the placement of cells, e.g., progenitor cells, into a subject, by a method or route that results in at least partial localization of the introduced cells at a desired site, such as a site of injury or repair, such that a desired effect(s) is produced. The cells e.g., progenitor cells, or their differentiated progeny, can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e., long-term engraftment. For example, in some aspects described herein, an effective amount of myogenic progenitor cells is administered via a systemic route of administration, such as an intraperitoneal or intravenous route.

The terms "individual", "subject," "host" and "patient" are used interchangeably herein and refer to any subject for whom diagnosis, treatment or therapy is desired. In some aspects, the subject is a mammal. In some aspects, the subject is a human being.

When provided prophylactically, progenitor cells described herein can be administered to a subject in advance of any symptom of DMD, e.g., prior to the development of muscle wasting. Accordingly, the prophylactic administration of a muscle progenitor cell population can serve to prevent DMD.

When provided therapeutically, muscle progenitor cells can be provided at (or after) the onset of a symptom or indication of DMD, e.g., upon the onset of muscle wasting.

The muscle progenitor cell population being administered according to the methods described herein can comprise allogeneic muscle progenitor cells obtained from one or more donors. "Allogeneic" refers to a muscle progenitor cell or biological samples comprising muscle progenitor cells obtained from one or more different donors of the same species, where the genes at one or more loci are not identical. For example, a muscle progenitor cell population being administered to a subject can be derived from one more unrelated donor subjects, or from one or more non-identical siblings. In some cases, syngeneic muscle progenitor cell populations can be used, such as those obtained from genetically identical animals, or from identical twins. The muscle progenitor cells can be autologous cells; that is, the muscle progenitor cells are obtained or isolated from a subject and administered to the same subject, i.e., the donor and recipient are the same.

The term "effective amount" refers to the amount of a population of progenitor cells or their progeny needed to prevent or alleviate at least one or more signs or symptoms of DMD, and relates to a sufficient amount of a composition to provide the desired effect, e.g., to treat a subject having DMD. The term "therapeutically effective amount" therefore refers to an amount of progenitor cells or a composition comprising progenitor cells that is sufficient to promote a particular effect when administered to a typical subject, such as one who has or is at risk for DMD. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of progenitor cells comprises at least $10^2$ progenitor cells, at least $5 \times 10^2$ progenitor cells, at least $10^3$ progenitor cells, at least $5 \times 10^3$ progenitor cells, at least $10^4$ progenitor cells, at least $5 \times 10^4$ progenitor cells, at least $10^5$ progenitor cells, at least $2 \times 10^5$ progenitor cells, at least $3 \times 10^5$ progenitor cells, at least $4 \times 10^5$ progenitor cells, at least $5 \times 10^5$ progenitor cells, at least $6 \times 10^5$ progenitor cells, at least $7 \times 10^5$ progenitor cells, at least $8 \times 10^5$ progenitor cells, at least $9 \times 10^5$ progenitor cells, at least $1 \times 10^6$ progenitor cells, at least $2 \times 10^6$ progenitor cells, at least $3 \times 10^6$ progenitor cells, at least $4 \times 10^6$ progenitor cells, at least $5 \times 10^6$ progenitor cells, at least $6 \times 10^6$ progenitor cells, at least $7 \times 10^6$ progenitor cells, at least $8 \times 10^6$ progenitor cells, at least $9 \times 10^6$ progenitor cells, or multiples thereof. The progenitor cells can be derived from one or more donors, or can be obtained from an autologous source. In some examples described herein, the progenitor cells can be expanded in culture prior to administration to a subject in need thereof.

Modest and incremental increases in the levels of functional dystrophin expressed in cells of patients having DMD can be beneficial for ameliorating one or more symptoms of the disease, for increasing long-term survival, and/or for reducing side effects associated with other treatments. Upon administration of such cells to human patients, the presence of muscle progenitors that are producing increased levels of functional dystrophin is beneficial. In some cases, effective treatment of a subject gives rise to at least about 3%, 5%, or 7% functional dystrophin relative to total dystrophin in the treated subject. In some examples, functional dystrophin will be at least about 10% of total dystrophin. In some examples, functional dystrophin will be at least about 20% to 30% of total dystrophin. Similarly, the introduction of even relatively limited subpopulations of cells having significantly elevated levels of functional dystrophin can be beneficial in various patients because in some situations normalized cells will have a selective advantage relative to diseased cells. However, even modest levels of muscle progenitors with elevated levels of functional dystrophin can be beneficial for ameliorating one or more aspects of DMD in patients. In some examples, about 10%, about 20%, about 30%, about 40%, about 50%, about 60%, about 70%, about 80%, about 90% or more of the muscle progenitors in patients to whom such cells are administered are producing increased levels of functional dystrophin.

"Administered" refers to the delivery of a progenitor cell composition into a subject by a method or route that results in at least partial localization of the cell composition at a desired site. A cell composition can be administered by any appropriate route that results in effective treatment in the subject, i.e. administration results in delivery to a desired location in the subject where at least a portion of the composition delivered, i.e. at least $1 \times 10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

The cells are administered systemically. The phrases "systemic administration," "administered systemically", "peripheral administration" and "administered peripherally" refer to the administration of a population of progenitor cells other than directly into a target site, tissue, or organ, such that it enters, instead, the subject's circulatory system and, thus, is subject to metabolism and other like processes.

The efficacy of a treatment comprising a composition for the treatment of DMD can be determined by the skilled clinician. However, a treatment is considered "effective treatment," if any one or all of the signs or symptoms of, as but one example, levels of functional dystrophin are altered in a beneficial manner (e.g., increased by at least 10%), or other clinically accepted symptoms or markers of disease are improved or ameliorated. Efficacy can also be measured by failure of an individual to worsen as assessed by hospitalization or need for medical interventions (e.g., reduced muscle wasting, or progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

The treatment according to the present disclosure can ameliorate one or more symptoms associated with DMD by increasing the amount of functional dystrophin in the individual. Early signs typically associated with DMD, include for example, delayed walking, enlarged calf muscle (due to scar tissue), and falling frequently. As the disease progresses, children become wheel chair bound due to muscle wasting and pain. The disease becomes life threatening due to heart and/or respiratory complications.

Kits

The present disclosure provides kits for carrying out the methods described herein. A kit can include one or more of a genome-targeting nucleic acid, a polynucleotide encoding a genome-targeting nucleic acid, a site-directed polypeptide, a polynucleotide encoding a site-directed polypeptide, and/or any nucleic acid or proteinaceous molecule necessary to carry out the aspects of the methods described herein, or any combination thereof.

A kit can comprise: (1) a vector comprising a nucleotide sequence encoding a genome-targeting nucleic acid, and (2) the site directed polypeptide or a vector comprising a nucleotide sequence encoding the site-directed polypeptide, and (3) a reagent for reconstitution and/or dilution of the vector(s) and or polypeptide.

A kit can comprise: (1) a vector comprising (i) a nucleotide sequence encoding a genome-targeting nucleic acid, and (ii) a nucleotide sequence encoding the site-directed polypeptide and (2) a reagent for reconstitution and/or dilution of the vector.

In some of the kits, the kit can comprise a single-molecule guide genome-targeting nucleic acid. In any of the above kits, the kit can comprise a double-molecule genome-targeting nucleic acid. In any of the kits, the kit can comprise two or more double-molecule guides or single-molecule guides. The kits can comprise a vector that encodes the nucleic acid targeting nucleic acid.

In any of the kits, the kit can further comprise a polynucleotide to be inserted to effect the desired genetic modification.

Components of a kit can be in separate containers, or combined in a single container.

Any kit can further comprise one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the endonuclease, or improve the specificity of targeting.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

Guide RNA Formulation

Guide RNAs of the present disclosure can be formulated with pharmaceutically acceptable excipients such as carriers, solvents, stabilizers, adjuvants, diluents, etc., depending upon the particular mode of administration and dosage form. Guide RNA compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Other Possible Therapeutic Approaches

Gene editing can be conducted using nucleases engineered to target specific sequences. To date there are four major types of nucleases: meganucleases and their derivatives, zinc finger nucleases (ZFNs), transcription activator like effector nucleases (TALENs), and CRISPR-Cas9 nuclease systems. The nuclease platforms vary in difficulty of design, targeting density and mode of action, particularly as the specificity of ZFNs and TALENs is through protein-DNA interactions, while RNA-DNA interactions primarily guide Cas9. Cas9 cleavage also requires an adjacent motif, the PAM, which differs between different CRISPR systems. Cas9 from *Streptococcus pyogenes* cleaves using a NGG PAM, CRISPR from *Neisseria meningitidis* can cleave at sites with PAMs including NNNNGATT, NNNNNGTTT and NNNNGCTT. A number of other Cas9 orthologs target protospacer adjacent to alternative PAMs.

CRISPR endonucleases, such as Cas9, can be used in the methods of the present disclosure. However, the teachings described herein, such as therapeutic target sites, could be applied to other forms of endonucleases, such as ZFNs, TALENs, HEs, or MegaTALs, or using combinations of nucleases. However, in order to apply the teachings of the present disclosure to such endonucleases, one would need to, among other things, engineer proteins directed to the specific target sites.

Additional binding domains can be fused to the Cas9 protein to increase specificity. The target sites of these constructs would map to the identified gRNA specified site, but would require additional binding motifs, such as for a zinc finger domain. In the case of Mega-TAL, a meganuclease can be fused to a TALE DNA-binding domain. The meganuclease domain can increase specificity and provide the cleavage. Similarly, inactivated or dead Cas9 (dCas9) can be fused to a cleavage domain and require the sgRNA/Cas9 target site and adjacent binding site for the fused DNA-binding domain. This likely would require some protein engineering of the dCas9, in addition to the catalytic inactivation, to decrease binding without the additional binding site Zinc Finger Nucleases Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., *Proc Natl Acad Sci USA* 96(6):2758-63 (1999); Dreier B et al., *J Mol Biol.* 303(4):489-502 (2000); Liu Q et al., *J Biol Chem.* 277(6):3850-6 (2002); Dreier et al., *J Biol Chem* 280(42): 35588-97 (2005); and Dreier et al., *J Biol Chem.* 276(31): 29466-78 (2001).

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single basepair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefited from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, *Science* 326(5959):1509-12 (2009); Mak et al., *Science* 335(6069):716-9 (2012); and Moscou et al., *Science* 326(5959):1501 (2009). The use of TALENs based on the "Golden Gate" platform, or cloning scheme, has been described by multiple groups; see, e.g., Cermak et al., *Nucleic Acids Res.* 39(12):e82 (2011); Li et al., *Nucleic Acids Res.* 39(14):6315-25 (2011); Weber et al., *PLoS One.* 6(2):e16765 (2011); Wang et al., *J Genet Genomics* 41(6): 339-47, Epub 2014 May 17 (2014); and Cermak T et al., *Methods Mol Biol.* 1239:133-59 (2015).

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including LAGLIDADG (SEQ ID NO. 1,410,474), GIY-YIG, His-Cis box, H—N—H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology 24(8): 663-80 (2014); Belfort and Bonocora, *Methods Mol* Biol. 1123:1-26 (2014); Hafez and Hausner, Genome 55(8):553-69 (2012); and references cited therein.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., *NAR* 42: 2591-2601 (2014); Kleinstiver et al., G3 4:1155-65 (2014); and Boissel and Scharenberg, *Methods Mol. Biol.* 1239: 171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., *NAR* 42, 8816-29 (2014). It is anticipated that other combinations of existing nuclease-based approaches will evolve and be useful in achieving the targeted genome modifications described herein.

dCas9-FokI or dCpf1-Fok1 and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., *Nature Biotech* 32: 569-76 (2014); and Guilinger et al., *Nature Biotech.* 32: 577-82 (2014). Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

Methods and Compositions of the Invention

Accordingly, the present disclosure relates in particular to the following non-limiting inventions: In a first method, Method 1, the present disclosure provides a method for editing a dystrophin gene in a human cell by genome editing, the method comprising the step of: introducing into the human cell one or more deoxyribonucleic acid (DNA) endonucleases to effect one or more single-strand breaks (SSBs) or double-strand breaks (DSBs) within or near the dystrophin gene that results in a permanent deletion, insertion, or replacement of one or more exons or aberrant intronic splice acceptor or donor sites within or near the dystrophin gene and results in restoration of the dystrophin reading frame and restoration of the dystrophin protein activity.

In another method, Method 2, the present disclosure provides a method for editing a dystrophin gene in a human cell by genome editing, as provided in Method 1, wherein the human cell is a muscle cell or muscle precursor cell.

In another method, Method 3, the present disclosure provides an ex vivo method for treating a patient with Duchenne Muscular Dystrophy (DMD), the method comprising the steps of: i) creating a DMD patient specific induced pluripotent stem cell (iPSC); ii) editing within or near a dystrophin gene of the iPSC; iii) differentiating the genome-edited iPSC into a Pax7+ muscle progenitor cell; and iv) implanting the Pax7+ muscle progenitor cell into the patient.

In another method, Method 4, the present disclosure provides an ex vivo method for treating a patient with DMD, as provided in Method 3, wherein the creating step comprises: a) isolating a somatic cell from the patient; and b) introducing a set of pluripotency-associated genes into the somatic cell to induce the somatic cell to become a pluripotent stem cell.

In another method, Method 5, the present disclosure provides an ex vivo method for treating a patient with DMD, as provided in Method 4, wherein the somatic cell is a fibroblast.

In another method, Method 6, the present disclosure provides an ex vivo method for treating a patient with DMD, as provided in Methods 4 and 5, wherein the set of pluripotency-associated genes is one or more of the genes selected from the group consisting of OCT4, SOX2, KLF4, Lin28, NANOG and cMYC.

In another method, Method 7, the present disclosure provides an ex vivo method for treating a patient with DMD, as provided in any one of Methods 3-6, wherein the editing step comprises introducing into the iPSC one or more deoxyribonucleic acid (DNA) endonucleases to effect one or more single-strand breaks (SSBs) or double-strand breaks (DSBs) within or near the dystrophin gene that results in a permanent deletion, insertion, or replacement of one or more exons or aberrant intronic splice acceptor or donor sites within or near the dystrophin gene and results in restoration of the dystrophin reading frame and restoration of the dystrophin protein activity.

In another method, Method 8, the present disclosure provides an ex vivo method for treating a patient with DMD, as provided in any one of Methods 3-7, wherein the differentiating step comprises one or more of the following to differentiate the genome-edited iPSC into a Pax7+ muscle progenitor cell: contacting the genome-edited iPSC with specific media formulations, including small molecule drugs; transgene overexpression; or serum withdrawal.

In another method, Method 9, the present disclosure provides an ex vivo method for treating a patient with DMD, as provided in any one of Methods 3-8, wherein the implanting step comprises implanting the Pax7+ muscle progenitor cell into the patient by local injection into the desired muscle.

In another method, Method 10, the present disclosure provides an in vivo method for treating a patient with DMD, the method comprising the step of editing a dystrophin gene in a cell of the patient.

In another method, Method 11, the present disclosure provides an in vivo method for treating a patient with DMD, as provided in Method 10, wherein the editing step comprises introducing into the cell of the patient one or more deoxyribonucleic acid (DNA) endonucleases to effect one or more single-strand breaks (SSBs) or double-strand breaks (DSBs) within or near the dystrophin gene that results in a permanent deletion, insertion, or replacement of one or more exons or aberrant intronic splice acceptor or donor sites within or near the dystrophin gene and results in restoration of the dystrophin reading frame and restoration of the dystrophin protein activity.

In another method, Method 12, the present disclosure provides an in vivo method for treating a patient with DMD, as provided in Method 11, wherein the cell is a muscle cell or muscle precursor cell.

In another method, Method 13, the present disclosure provides an in vivo method for treating a patient with DMD, as provided in any one of Methods 1, 7, and 11, wherein the one or more DNA endonucleases is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, a codon-optimized thereof, modified version thereof, and combinations thereof.

In another method, Method 14, the present disclosure provides a method as provided in Method 13, wherein the method comprises introducing into the cell one or more polynucleotides encoding the one or more DNA endonucleases.

In another method, Method 15, the present disclosure provides a method as provided in Method 13, wherein the method comprises introducing into the cell one or more ribonucleic acids (RNAs) encoding the one or more DNA endonucleases.

In another method, Method 16, the present disclosure provides a method as provided in Methods 14 and 15, wherein the one or more polynucleotides or one or more RNAs is one or more modified polynucleotides or one or more modified RNAs.

In another method, Method 17, the present disclosure provides a method as provided in Method 13, wherein the one or more DNA endonuclease is one or more proteins or polypeptides.

In another method, Method 18, the present disclosure provides a method as provided in any one of Methods 1-17, wherein the method further comprises introducing into the cell one or more guide ribonucleic acids (gRNAs).

In another method, Method 19, the present disclosure provides a method as provided in Method 18, wherein the one or more gRNAs are single-molecule guide RNA (sgRNAs).

In another method, Method 20, the present disclosure provides a method as provided in Methods 18 and 19, wherein the one or more gRNAs or one or more sgRNAs is one or more modified gRNAs or one or more modified sgRNAs.

In another method, Method 21, the present disclosure provides a method as provided in any one of Methods 18-20, wherein the one or more DNA endonucleases is pre-complexed with one or more gRNAs or one or more sgRNAs.

In another method, Method 22, the present disclosure provides a method as provided in any one of Methods 1-21, wherein the method further comprises introducing into the cell a polynucleotide donor template comprising at least a portion of the wild-type dystrophin gene or cDNA.

In another method, Method 23, the present disclosure provides a method as provided in Method 22, wherein the at least a portion of the wild-type dystrophin gene or cDNA includes at least a part of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA.

In another method, Method 24, the present disclosure provides a method as provided in Method 22, wherein the at least a portion of the wild-type dystrophin gene or cDNA includes exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA.

In another method, Method 25, the present disclosure provides a method as provided in any one of Methods 22-24, wherein the donor template is a single or double stranded polynucleotide.

In another method, Method 26, the present disclosure provides a method as provided in any one of Methods 1, 7, and 11, wherein the method further comprises introducing into the cell one or more guide ribonucleic acid (gRNAs), and wherein the one or more DNA endonucleases is one or more Cas9 or Cpf1 endonucleases that effect a pair of single-strand breaks (SSBs) or double-strand breaks (DSBs), the first SSB or DSB break at a 5' locus and the second SSB or DSB break at a 3' locus, that results in a permanent deletion or replacement of one or more exons or aberrant intronic splice acceptor or donor sites between the 5' locus and the 3' locus within or near the dystrophin gene and results in restoration of the dystrophin reading frame and restoration of the dystrophin protein activity.

In another method, Method 27, the present disclosure provides a method as provided in Method 26, wherein one gRNA creates a pair of SSBs or DSBs.

In another method, Method 28, the present disclosure provides a method as provided in Method 26, wherein one gRNA comprises a spacer sequence that is complementary to either the 5' locus, the 3' locus, or a segment between the 5' locus and 3' locus.

In another method, Method 29, the present disclosure provides a method as provided in Method 26, wherein the method comprises a first gRNA and a second gRNA, wherein the first gRNA comprises a spacer sequence that is complementary to a segment of the 5' locus and the second gRNA comprises a spacer sequence that is complementary to a segment of the 3' locus.

In another method, Method 30, the present disclosure provides a method as provided in Methods 26-29, wherein the one or more gRNAs are one or more single-molecule guide RNAs (sgRNAs).

In another method, Method 31, the present disclosure provides a method as provided in Methods 26-30, wherein the one or more gRNAs or one or more sgRNAs are one or more modified gRNAs or one or more modified sgRNAs.

In another method, Method 32, the present disclosure provides a method as provided in any one of Methods 26-31, wherein the one or more DNA endonucleases is pre-complexed with one or more gRNAs or one or more sgRNAs.

In another method, Method 33, the present disclosure provides a method as provided in any one of Methods 26-32, wherein there is a deletion of the chromosomal DNA between the 5' locus and the 3' locus.

In another method, Method 34, the present disclosure provides a method as provided in any one of Methods 26-33, wherein the deletion is a single exon deletion.

In another method, Method 35, the present disclosure provides a method as provided in Method 34, wherein the single exon deletion is a deletion of exon 2, exon 8, exon 43, exon 44, exon 45, exon 46, exon 50, exon 51, exon 52, or exon 53.

In another method, Method 36, the present disclosure provides a method as provided in Methods 34 or 35, wherein the 5' locus is proximal to a 5' boundary of a single exon selected from the group consisting of exon 2, exon 8, exon 43, exon 44, exon 45, exon 46, exon 50, exon 51, exon 52, and exon 53.

In another method, Method 37, the present disclosure provides a method as provided in any one of Methods 34-36, wherein the 3' locus is proximal to a 3' boundary of a single exon selected from the group consisting of exon 2, exon 8, exon 43, exon 44, exon 45, exon 46, exon 50, exon 51, exon 52, and exon 53.

In another method, Method 38, the present disclosure provides a method as provided in any one of Methods 34-37, wherein the 5' locus is proximal to a 5' boundary and the 3' locus is proximal to the 3' boundary of a single exon selected from the group consisting of exon 2, exon 8, exon 43, exon 44, exon 45, exon 46, exon 50, exon 51, exon 52, and exon 53.

In another method, Method 39, the present disclosure provides a method as provided in any one of Methods 36-38, wherein proximal to the boundary of the exon includes the surrounding splice donors and acceptors of the neighboring intron.

In another method, Method 40, the present disclosure provides a method as provided in any one of Methods 26-33, wherein the deletion is a multi-exon deletion.

In another method, Method 41, the present disclosure provides a method as provided in Method 40, wherein the multi-exon deletion is a deletion of exons 45-53 or exons 45-55.

In another method, Method 42, the present disclosure provides a method as provided in any one of Methods 40-41, wherein the 5' locus is proximal to a 5' boundary of multiple exons selected from the group consisting of exons 45-53 and exons 45-55.

In another method, Method 43, the present disclosure provides a method as provided in any one of Methods 40-42, wherein the 3' locus is proximal to a 3' boundary of multiple exons selected from the group consisting of exons 45-53 and exons 45-55.

In another method, Method 44, the present disclosure provides a method as provided in any one of Methods 40-43, wherein the 5' locus is proximal to a 5' boundary and a 3' locus is proximal to the 3' boundary of multiple exons selected from the group consisting of exons 45-53 and exons 45-55.

In another method, Method 45, the present disclosure provides a method as provided in any one of Methods 42-44, wherein proximal to the boundary of the exon includes the surrounding splice donors and acceptors of the neighboring intron.

In another method, Method 46, the present disclosure provides a method as provided in any one of Methods 26-32, wherein there is a replacement of the chromosomal DNA between the 5' locus and the 3' locus.

In another method, Method 47, the present disclosure provides a method as provided in any one of Methods 26-32 and 46, wherein the replacement is a single exon replacement.

In another method, Method 48, the present disclosure provides a method as provided in any one of Methods 26-32 and 46-47, wherein the single exon replacement is a replacement of exon 2, exon 8, exon 43, exon 44, exon 45, exon 46, exon 50, exon 51, exon 52, exon 53, or exon 70.

In another method, Method 49, the present disclosure provides a method as provided in any one of Methods 47-48, wherein the 5' locus is proximal to a 5' boundary of a single exon selected from the group consisting of exon 2, exon 8, exon 43, exon 44, exon 45, exon 46, exon 50, exon 51, exon 52, exon 53, or exon 70.

In another method, Method 50, the present disclosure provides a method as provided in any one of Methods 47-49, wherein the 3' locus is proximal to a 3' boundary of a single exon selected from the group consisting of exon 2, exon 8, exon 43, exon 44, exon 45, exon 46, exon 50, exon 51, exon 52, exon 53, or exon 70.

In another method, Method 51, the present disclosure provides a method as provided in any one of Methods 47-50, wherein the 5' locus is proximal to a 5' boundary and a 3' locus is proximal to the 3' boundary of a single exon selected from the group consisting of exon 2, exon 8, exon 43, exon 44, exon 45, exon 46, exon 50, exon 51, exon 52, exon 53, or exon 70.

In another method, Method 52, the present disclosure provides a method as provided in any one of Methods 49-51, wherein proximal to the boundary of the exon includes the surrounding splice donors and acceptors of the neighboring intron or neighboring exon.

In another method, Method 53, the present disclosure provides a method as provided in any one of Methods 26-32 or 46, wherein the replacement is a multi-exon replacement.

In another method, Method 54, the present disclosure provides a method as provided in any one of Method 53, wherein the multi-exon replacement is a replacement of exons 45-53 or exons 45-55.

In another method, Method 55, the present disclosure provides a method as provided in any one of Methods 53-54, wherein the 5' locus is proximal to a 5' boundary of multiple exons selected from the group consisting of exons 45-53 and exons 45-55.

In another method, Method 56, the present disclosure provides a method as provided in any one of Methods 53-55, wherein the 3' locus is proximal to a 3' boundary of multiple exons selected from the group consisting of exons 45-53 and exons 45-55.

In another method, Method 57, the present disclosure provides a method as provided in any one of Methods 53-56, wherein the 5' locus is proximal to a 5' boundary and a 3' locus is proximal to the 3' boundary of multiple exons selected from the group consisting of exons 45-53 and exons 45-55.

In another method, Method 58, the present disclosure provides a method as provided in any one of Methods 55-57, wherein proximal to the boundary of the exon includes the surrounding splice donors and acceptors of the neighboring intron.

In another method, Method 59, the present disclosure provides a method as provided in any one of Methods 46-58, wherein the method further comprises introducing into the cell a polynucleotide donor template comprising at least a portion of the wild-type dystrophin gene or cDNA, and the replacement is by homology directed repair (HDR).

In another method, Method 60, the present disclosure provides a method as provided in any one of Method 59, wherein the at least a portion of the wild-type dystrophin gene or cDNA includes at least a part of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA.

In another method, Method 61, the present disclosure provides a method as provided in any one of Method 59, wherein the at least a portion of the wild-type dystrophin gene or cDNA includes exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA.

In another method, Method 62, the present disclosure provides a method as provided in any one of Methods 1, 7, or 11, wherein the method further comprises introducing into the cell one guide ribonucleic acid (gRNA) and a polynucleotide donor template comprising at least a portion of the wild-type dystrophin gene, and wherein the one or more DNA endonucleases is one or more Cas9 or Cpf1 endonucleases that effect one single-strand break (SSB) or double-strand break (DSB) at a locus within or near the dystrophin gene that facilitates insertion of a new sequence from the polynucleotide donor template into the chromosomal DNA at the locus that results in permanent insertion or correction of one or more exons or aberrant intronic splice acceptor or donor sites within or near the dystrophin gene and results in restoration of the dystrophin reading frame and restoration of the dystrophin protein activity, and wherein the gRNA comprises a spacer sequence that is complementary to a segment of the locus.

In another method, Method 63, the present disclosure provides a method as provided in any one of Methods 1, 7, or 11, wherein the method further comprises introducing into the cell one or more guide ribonucleic acid (gRNAs) and a polynucleotide donor template comprising at least a portion of the wild-type dystrophin gene, and wherein the one or more DNA endonucleases is one or more Cas9 or Cpf1 endonucleases that effect a pair of single-strand breaks (SSBs) or double-strand breaks (DSBs), the first at a 5' locus and the second at a 3' locus, within or near the dystrophin gene that facilitates insertion of a new sequence from the polynucleotide donor template into the chromosomal DNA between the 5' locus and the 3' locus that results in a permanent insertion or correction of one or more exons or aberrant intronic splice acceptor or donor sites between the 5' locus and the 3' locus within or near the dystrophin gene and results in restoration of the dystrophin reading frame and restoration of the dystrophin protein activity.

In another method, Method 64, the present disclosure provides a method as provided in Method 63, wherein one gRNA creates a pair of SSBs or DSBs.

In another method, Method 65, the present disclosure provides a method as provided in Method 63, wherein one gRNA comprises a spacer sequence that is complementary to either the 5' locus, the 3' locus, or a segment between the 5' locus and the 3' locus.

In another method, Method 66, the present disclosure provides a method as provided in Method 63, wherein the method comprises a first gRNA and a second gRNA, wherein the first gRNA comprises a spacer sequence that is complementary to a segment of the 5' locus and the second gRNA comprises a spacer sequence that is complementary to a segment of the 3' locus.

In another method, Method 67, the present disclosure provides a method as provided in Methods 62 or 63, wherein the one or more gRNAs are one or more single-molecule guide RNAs (sgRNAs).

In another method, Method 68, the present disclosure provides a method as provided in Methods 62-63 or 67, wherein the one or more gRNAs or one or more sgRNAs are one or more modified gRNAs or one or more modified sgRNAs.

In another method, Method 69, the present disclosure provides a method as provided in any one of Methods 62-63 or 67-68, wherein the one or more DNA endonucleases is pre-complexed with one or more gRNAs or one or more sgRNAs.

In another method, Method 70, the present disclosure provides a method as provided in any one of Methods 62-69, wherein the insertion is a single exon insertion In another method, Method 71, the present disclosure provides a method as provided in Method 70, wherein the single exon insertion is an insertion of exon 2, exon 8, exon 43, exon 44, exon 45, exon 46, exon 50, exon 51, exon 52, exon 53 or exon 70.

In another method, Method 72, the present disclosure provides a method as provided in any one of Methods 70-71, wherein the locus, 5' locus, or 3' locus is proximal to a boundary of a single exon selected from the group consisting of exon 2, exon 8, exon 43, exon 44, exon 45, exon 46, exon 50, exon 51, exon 52, exon 53 and exon 70.

In another method, Method 73, the present disclosure provides a method as provided in Method 72, wherein proximal to the boundary of the exon includes the surrounding splice donors and acceptors of the neighboring intron or neighboring exon.

In another method, Method 74, the present disclosure provides a method as provided in any one of Methods 62-69, wherein the insertion is a multi-exon insertion.

In another method, Method 75, the present disclosure provides a method as provided in Method 74, wherein the multi-exon insertion is an insertion of exons 45-53 or exons 45-55.

In another method, Method 76, the present disclosure provides a method as provided in any one of Methods 74-75, wherein the locus, 5' locus, or 3' locus is proximal to a boundary of multiple-exons selected from the group consisting of exons 45-53 or exons 45-55.

In another method, Method 77, the present disclosure provides a method as provided in Method 76, wherein proximal to the boundary of the exon includes the surrounding splice donors and acceptors of the neighboring intron.

In another method, Method 78, the present disclosure provides a method as provided in any one of Methods 62 or 63, wherein the at least a portion of the wild-type dystrophin gene or cDNA includes at least a part of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA.

In another method, Method 79, the present disclosure provides a method as provided in any one of Methods 62 or 63, wherein the at least a portion of the wild-type dystrophin gene or cDNA includes exon 1, exon 2, exon 3, exon 4, exon 5, exon 6,
exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, exon 67, exon 68, exon 69, exon 70, exon 71, exon 72, exon 73, exon 74, exon 75, exon 76, exon 77, exon 78, exon 79, intronic regions, synthetic intronic regions, fragments, combinations thereof, or the entire dystrophin gene or cDNA.

In another method, Method 80, the present disclosure provides a method as provided in any one of Methods 62-79, wherein the insertion is by homology directed repair (HDR).

In another method, Method 81, the present disclosure provides a method as provided in any one of Methods 62-80, wherein the donor template is a single or double stranded polynucleotide.

In another method, Method 82, the present disclosure provides a method as provided in any one of Methods 26-81, wherein the Cas9 or Cpf1 mRNA, gRNA, and donor template are each formulated into separate lipid nanoparticles or all co-formulated into a lipid nanoparticle.

In another method, Method 83, the present disclosure provides a method as provided in any one of Methods 26-81, wherein the Cas9 or Cpf1 mRNA is formulated into a lipid nanoparticle, and both the gRNA and donor template are delivered to the cell by an adeno-associated virus (AAV) vector.

In another method, Method 84, the present disclosure provides a method as provided in any one of Methods 26-81, wherein the Cas9 or Cpf1 mRNA is formulated into a lipid nanoparticle, and the gRNA is delivered to the cell by electroporation and donor template is delivered to the cell by an adeno-associated virus (AAV) vector.

In another method, Method 85, the present disclosure provides a method as provided in any one of Methods 1-84, wherein the dystrophin gene is located on Chromosome X: 31,117,228-33,344,609 (Genome Reference Consortium—GRCh38/hg38).

In a first composition, Composition 1, the present disclosure provides one or more guide ribonucleic acids (gRNAs) for editing a dystrophin gene in a cell from a patient with Duchenne Muscular Dystrophy (DMD), the one or more gRNAs comprising a spacer sequence selected from the group consisting of the nucleic acid sequences in SEQ ID Nos: 1-1,410,472 of the Sequence Listing.

In another composition, Composition 2, the present disclosure provides the one or more gRNAs of Composition 1, wherein the one or more gRNAs are one or more single-molecule guide RNAs (sgRNAs).

In another composition, Composition 3, the present disclosure provides the one or more gRNAs or sgRNAs of Compositions 1 or 2, wherein the one or more gRNAs or one or more sgRNAs is one or more modified gRNAs or one or more modified sgRNAs.

Definitions

The term "comprising" or "comprises" is used in reference to compositions, methods, and respective component(s) thereof, that are essential to the invention, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the aspect.

The singular forms "a," "an," and "the" include plural references, unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

EXAMPLES

The invention will be more fully understood by reference to the following examples, which provide illustrative non-limiting aspects of the invention.

The examples describe the use of the CRISPR system as an illustrative genome editing technique to create defined therapeutic genomic deletions, insertions, or replacements, collectively termed "genomic modifications" herein, in the dystrophin gene (DMD gene) that lead to permanent deletion or correction of problematic exons from the genomic locus that restore the dystrophin reading frame and restore the dystrophin protein activity.

Single gRNAs spanning different regions of the DMD gene were selected and tested for cutting efficiencies (Table 5). gRNAs were targeted to exons, introns, and the splice acceptors of multiple areas of interest in the DMD gene. The naming convention for all gRNAs discussed in the Examples is: # (corresponding to the gRNA)—NN (Cas protein: SP—*S. pyogenes*, SA—*S. aureus*, NM—*N. meningitides*, ST—*S. thermophiles*, TD—*T. denticola*, Cpf1)—NN## (SA—Splice acceptor, E—Exon, I—Intron).

TABLE 5

| gRNA Name | gRNA sequence | SEQ ID NO: |
|---|---|---|
| 1-NM-SA51 | AGTCTGAGTAGGAGCTAAAATATT | 1410400 |
| 2-NM-SA44 | CTTGATCCATATGCTTTTACCTGC | 1410401 |
| 3-NM-SA52 | ATATTTGTTCTTACAGGCAACAAT | 1410402 |
| 1-ST-SA53 | CTGATTCTGAATTCTTTCAA | 534494 |
| 2-ST-SA53 | TTTTCCTTTTATTCTAGTTG | 534495 |
| 3-ST-SA46 | TTCTTTTGTTCTTCTAGCCT | 537307 |
| 4-ST-SA46 | GTTCTTCTAGCCTGGAGAAA | 537308 |
| 5-ST-SA50 | ATCTTCTAACTTCCTCTTTA | 536097 |
| 6-ST-SA43 | TGTTTTAAAATTTTTATATT | 541322 |
| 1-SA-SA51 | TGAGTAGGAGCTAAAATATT | 485512 |
| 2-SA-SA45 | TTGGTATCTTACAGGAACTC | 490807 |
| 3-SA-SA53 | TGATTCTGAATTCTTTCAAC | 482860 |
| 4-SA-SA53 | TTTCCTTTTATTCTAGTTGA | 482861 |
| 5-SA-SA46 | TTCTTCTAGCCTGGAGAAAG | 489814 |
| 6-SA-SA43 | GTTTTAAAATTTTTATATTA | 499467 |
| 7-SA-SA55 | TCTGAACATTTGGTCCTTTG | 481421 |
| 8-SA-SA55 | AACATTTGGTCCTTTGCAGG | 481420 |
| 1-Cpf1-SA51 | TGCAAAAACCCAAAATATTTTAG | 1410403 |
| 2-Cpf1-SA51 | GCAAAAACCCAAAATATTTTAGC | 1410404 |
| 3-Cpf1-SA51 | CAAAAACCCAAAATATTTTAGCT | 1410405 |
| 4-Cpf1-SA45 | CCGCTGCCCAATGCCATCCTGGA | 1410406 |
| 5-Cpf1-SA45 | TGTTTTGCCTTTTTGGTATCTTA | 1410407 |
| 6-Cpf1-SA45 | GTTTTGCCTTTTTGGTATCTTAC | 1410408 |
| 7-Cpf1-SA45 | TTTTGCCTTTTTGGTATCTTACA | 1410409 |
| 8-Cpf1-SA45 | GCCTTTTTGGTATCTTACAGGAA | 1410410 |
| 9-Cpf1-SA45 | CCTTTTTGGTATCTTACAGGAAC | 1410411 |
| 10-Cpf1-SA45 | TGGTATCTTACAGGAACTCCAGG | 1410412 |
| 11-Cpf1-SA53 | TTTTTCCTTTTATTCTAGTTGAA | 1410413 |
| 12-Cpf1-SA53 | TCCTTTTATTCTAGTTGAAAGAA | 1410414 |
| 13-Cpf1-SA53 | CCTTTTATTCTAGTTGAAAGAAT | 1410415 |
| 14-Cpf1-SA44 | TCAACAGATCTGTCAAATCGCCT | 1410416 |
| 15-Cpf1-SA44 | TCTTGATCCATATGCTTTTACCT | 1410417 |
| 16-Cpf1-SA44 | CTTGATCCATATGCTTTTACCTG | 1410418 |
| 17-Cpf1-SA44 | TTGATCCATATGCTTTTACCTGC | 1410419 |
| 18-Cpf1-SA46 | GTTCTTCTAGCCTGGAGAAAGAA | 1410420 |
| 19-Cpf1-SA46 | TTCTTCTAGCCTGGAGAAAGAAG | 1410421 |
| 20-Cpf1-SA46 | ATTCTTCTTTCTCCAGGCTAGAA | 1410422 |
| 21-Cpf1-SA46 | TTCTTCTTTCTCCAGGCTAGAAG | 1410423 |
| 22-Cpf1-SA43 | TTGTAGACTATCTTTTATATTCT | 1410424 |
| 23-Cpf1-SA43 | TACTGTTTTAAAATTTTTATATT | 1410425 |
| 24-Cpf1-SA43 | ACTGTTTTAAAATTTTTATATTA | 1410426 |
| 25-Cpf1-SA43 | CTGTTTTAAAATTTTTATATTAC | 1410427 |
| 26-Cpf1-SA43 | AAAATTTTTATATTACAGAATAT | 1410428 |
| 27-Cpf1-SA43 | AAATTTTTATATTACAGAATATA | 1410429 |
| 1-SP-SA51 | AAAATATTTTAGCTCCTACT | 145442 |
| 2-SP-SA51 | TGCAAAAACCCAAAATATTT | 145443 |
| 3-SP-SA45 | TGGTATCTTACAGGAACTCC | 186216 |
| 4-SP-SA45 | TTGGTATCTTACAGGAACTC | 186217 |
| 5-SP-SA45 | TGCCATCCTGGAGTTCCTGT | 186218 |
| 6-SP-SA45 | TTGCCTTTTTGGTATCTTAC | 186219 |
| 7-SP-SA45 | TTTGCCTTTTTGGTATCTTA | 186220 |
| 8-SP-SA53 | TGATTCTGAATTCTTTCAAC | 125451 |
| 9-SP-SA53 | TTTCCTTTTATTCTAGTTGA | 125452 |
| 10-SP-SA53 | AATTCTTTCAACTAGAATAA | 125453 |
| 11-SP-SA53 | ATTTATTTTCCTTTTATTC | 125455 |
| 12-SP-SA53 | ATTCTTTCAACTAGAATAAA | 125454 |
| 13-SP-SA44 | AGATCTGTCAAATCGCCTGC | 237600 |
| 14-SP-SA44 | CAGATCTGTCAAATCGCCTG | 237599 |
| 15-SP-SA44 | GTCAAATCGCCTGCAGGTAA | 237602 |
| 16-SP-SA44 | GATCCATATGCTTTTACCTG | 237603 |
| 17-SP-SA44 | ATCCATATGCTTTTACCTGC | 237601 |

TABLE 5-continued

| gRNA Name | gRNA sequence | SEQ ID NO: |
|---|---|---|
| 18-SP-SA46 | TTGTTCTTCTAGCCTGGAGA | 178873 |
| 19-SP-SA46 | ATTCTTTTGTTCTTCTAGCC | 178869 |
| 20-SP-SA46 | TTCTTCTAGCCTGGAGAAAG | 178875 |
| 21-SP-SA46 | TTCTTCTTTCTCCAGGCTAG | 178870 |
| 22-SP-SA46 | TCTTTTGTTCTTCTAGCCTG | 178871 |
| 23-SP-SA46 | AAGATATTCTTTTGTTCTTC | 178868 |
| 24-SP-SA46 | TTATTCTTCTTTCTCCAGGC | 178872 |
| 25-SP-SA46 | AATTTTATTCTTCTTTCTCC | 178874 |
| 26-SP-SA46 | CAATTTTATTCTTCTTTCTC | 178876 |
| 27-SP-SA52 | AATCCTGCATTGTTGCCTGT | 136213 |
| 28-SP-SA52 | TAAGGGATATTTGTTCTTAC | 136214 |
| 29-SP-SA52 | CTAAGGGATATTTGTTCTTA | 136215 |
| 30-SP-SA50 | ATGCTTTTCTGTTAAAGAGG | 155685 |
| 31-SP-SA50 | TGTATGCTTTTCTGTTAAAG | 155687 |
| 32-SP-SA50 | TCTTCTAACTTCCTCTTTAA | 155686 |
| 33-SP-SA50 | ATGTGTATGCTTTTCTGTTA | 155689 |
| 34-SP-SA50 | TTTTCTGTTAAAGAGGAAGT | 155684 |
| 35-SP-SA50 | GTGTATGCTTTTCTGTTAAA | 155688 |
| 36-SP-SA43 | TTTTATATTACAGAATATAA | 252291 |
| 37-SP-SA43 | GTTTTAAAATTTTTATATTA | 252292 |
| 38-SP-SA55 | CTGAACATTTGGTCCTTTGC | 114755 |
| 39-SP-SA55 | CATTTGGTCCTTTGCAGGGT | 114751 |
| 40-SP-SA55 | CTCGCTCACTCACCCTGCAA | 114753 |
| 41-SP-SA55 | TCTGAACATTTGGTCCTTTG | 114756 |
| 42-SP-SA55 | TGGTCCTTTGCAGGGTGAGT | 114750 |
| 43-SP-SA55 | TCTCGCTCACTCACCCTGCA | 114752 |
| 44-SP-SA55 | TGAACATTTGGTCCTTTGCA | 114754 |
| 1-SP-E51 | CCTACTCAGACTGTTACTC | 1410430 |
| 2-SP-E51 | ACTCTGGTGACACAACCTG | 1410431 |
| 3-SP-E51 | ACACAACCTGTGGTTACTA | 1410432 |
| 4-SP-E51 | ATGTTGGAGGTACCTGCTC | 1410433 |
| 5-SP-E51 | TGCTCTGGCAGATTTCAAC | 1410434 |
| 6-SP-E51 | GCTCTGGCAGATTTCAACC | 1410435 |
| 7-SP-E51 | GGCAGATTTCAACCGGGCT | 1410436 |
| 8-SP-E51 | TTGGACAGAACTTACCGAC | 1410437 |
| 9-SP-E51 | CATCTCGTTGATATCCTCA | 1410438 |
| 10-SP-E51 | GGTAAGTTCTGTCCAAGCC | 1410439 |
| 11-SP-E51 | GGTTGAAATCTGCCAGAGC | 1410440 |
| 12-SP-E51 | GCAGGTACCTCCAACATCA | 1410441 |
| 13-SP-E51 | GGCATTTCTAGTTTGGAGA | 1410442 |
| 14-SP-E51 | CAGTTTCCTTAGTAACCAC | 1410443 |
| 15-SP-E51 | CCAGAGTAACAGTCTGAGT | 1410444 |
| 16-SP-E45 | GGTATCTTACAGGAACTCC | 1410445 |
| 17-SP-E45 | TCTTACAGGAACTCCAGGA | 1410446 |
| 18-SP-E45 | AGGAACTCCAGGATGGCAT | 1410447 |
| 19-SP-E45 | GGAACTCCAGGATGGCATT | 1410448 |
| 20-SP-E45 | CCAGGATGGCATTGGGCAG | 1410449 |
| 21-SP-E45 | TCAGAACATTGAATGCAAC | 1410450 |
| 22-SP-E45 | AGAACATTGAATGCAACTG | 1410451 |
| 23-SP-E45 | ACAGATGCCAGTATTCTAC | 1410452 |
| 24-SP-E45 | ATTGGGAAGCCTGAATCTG | 1410453 |
| 25-SP-E45 | GGGAAGCCTGAATCTGCGG | 1410454 |
| 26-SP-E45 | AGCCTGAATCTGCGGTGGC | 1410455 |
| 27-SP-E45 | CTCCTGCCACCGCAGATTC | 1410456 |
| 28-SP-E45 | CCGCTGCCCAATGCCATCC | 1410457 |
| 29-SP-E53 | ACAAGAACACCTTCAGAAC | 1410458 |
| 30-SP-E53 | AGAACACCTTCAGAACCGG | 1410459 |
| 31-SP-E53 | GTTAAAGGATTCAACACAA | 1410460 |
| 32-SP-E53 | ACACAATGGCTGGAAGCTA | 1410461 |
| 33-SP-E53 | GCTGAGCAGGTCTTAGGAC | 1410462 |
| 34-SP-E53 | CAGAGCCAAGCTTGAGTCA | 1410463 |
| 35-SP-E53 | GCCAAGCTTGAGTCATGGA | 1410464 |
| 36-SP-E53 | ACAAGAACACCTTCAGAAC | 1410465 |
| 37-SP-E53 | AGAACACCTTCAGAACCGG | 1410466 |
| 38-SP-E53 | GTTAAAGGATTCAACACAA | 1410467 |
| 39-SP-E53 | ACACAATGGCTGGAAGCTA | 1410468 |
| 40-SP-E53 | AAGAAGCTGAGCAGGTCTT | 1410469 |
| 41-SP-E53 | GCTGAGCAGGTCTTAGGAC | 1410470 |
| 42-SP-E53 | CAGAGCCAAGCTTGAGTCA | 1410471 |
| 43-SP-E53 | GCCAAGCTTGAGTCATGGA | 1410472 |
| 1-SP-I52 | ACAGTGGTTTAAGTAATCCG | 136258 |
| 2-SP-I52 | GGAGACATTCCGGAGTACCT | 136257 |
| 3-SP-I52 | TTTGGAGAGCATCAGATTAC | 136337 |
| 4-SP-I52 | GTTTGGTGATTCTTACGGAC | 136306 |
| 5-SP-I52 | TCTGTGTGACGTCAAAATTA | 136275 |
| 6-SP-I52 | ATATGATGTTCTACCACATG | 136406 |
| 1-SP-I53 | GCCCACCCTACTACGGCATA | 136093 |

TABLE 5-continued

| gRNA Name | gRNA sequence | SEQ ID NO: |
|---|---|---|
| 2-SP-I53 | CTGTACCTTATGCCGTAGTA | 136089 |
| 3-SP-I53 | ACTGTACCTTATGCCGTAGT | 136090 |
| 4-SP-I53 | TACCTTATGCCGTAGTAGGG | 136087 |
| 5-SP-I53 | ACCTTATGCCGTAGTAGGGT | 136086 |
| 6-SP-I53 | TGCACAGCGTCTAGTCAGAT | 136079 |
| 1-SP-I44 | CATCGCATAGTTTAGTATAT | 237710 |
| 2-SP-I44 | CTTAGGTAAACATACAGCCC | 237749 |
| 3-SP-I44 | ACTCCTTTCAGTTGATGAAC | 237661 |
| 4-SP-I44 | ATTTTAGATTGGAATACTGC | 237724 |
| 5-SP-I44 | GCCTCAGTCTCTTTTATGAC | 237740 |
| 6-SP-I44 | CTGCCTGTTCATCAACTGAA | 237664 |
| 1-SP-I45 | AATATTAGAGCACGGTGCTA | 237546 |
| 2-SP-I45 | CTCTATACAAATGCCAACGC | 237393 |
| 3-SP-I45 | CAGATAAACCAGCTCCGTCC | 237535 |
| 4-SP-I45 | AGGGAAGCATCGTAACAGCA | 237521 |
| 5-SP-I45 | ACTTGCATGCACACCAGCGT | 237394 |
| 6-SP-I45 | AGAGTTTGCCTGGACGGAGC | 237533 |
| 7-SP-I45 | TTAGTGATCGTGGATACGAG | 186301 |
| 8-SP-I45 | TTTGGGTTTCTTAGTGATCG | 186298 |
| 9-SP-I45 | AAAAACTGGAGCTAACCGAG | 186263 |
| 10-SP-I45 | CATTCAGATTTAAATACGGT | 186375 |
| 11-SP-I45 | AAAACTGGAGCTAACCGAGA | 186262 |
| 12-SP-I45 | TTTGTAAGCTTGTCAGCTAG | 186274 |
| 1-SP-I46 | CAACTGCAGCAGCACGCATT | 186065 |
| 2-SP-I46 | CCACCTATTATGTGGATGAT | 186030 |
| 3-SP-I46 | ATATACTTGTGGCTAGTTAG | 186135 |
| 4-SP-I46 | CCCATCATCCACATAATAGG | 186025 |
| 5-SP-I46 | CCATTAAACTTGTACCTCTT | 186083 |
| 6-SP-I46 | CCACCCATCATCCACATAAT | 186027 |
| 1-SP-I54 | GCTGGGGACCGTTATCTATT | 121156 |
| 2-SP-I54 | GCACATTCACGTATTACTGC | 121149 |
| 3-SP-I54 | TTTAGTTGAACGCCAGTAGA | 121051 |
| 4-SP-I54 | CACATTCACGTATTACTGCT | 121150 |
| 5-SP-I54 | ACATTCACGTATTACTGCTG | 121151 |
| 6-SP-I54 | CGTGAATGTGCTAGTTTTAC | 121147 |
| 1-SP-I55 | TAGCTCCCTATTATATCACG | 120796 |
| 2-SP-I55 | GCCAAGTCCGTGAGTTTAGT | 120916 |
| 3-SP-I55 | CCTATTATATCACGTGGTTC | 120798 |
| 4-SP-I55 | CCTGAACCACGTGATATAAT | 120794 |
| 5-SP-I55 | CTGAACCACGTGATATAATA | 120793 |
| 6-SP-I55 | TTCTCATTTGATACATCCCC | 120802 |
| 49-SP-I50 | CATTGGCTTTGATTTCCCTA | 145522 |
| 51-SP-I51 | ACAGTTGCCTAAGAACTGGT | 145360 |
| 53-SP-I55 | GCCTTCTTTATCCCCTATCG | 91033 |
| 44-SP-E70 | ACTGGCAGGTAGCCCATTCG | 13562 |
| 45-SP-E70 | TTTGCGAAGCATCCCCGAAT | 13563 |
| 46-SP-E70 | TTTTGCGAAGCATCCCCGAA | 13564 |
| 47-SP-E70 | CACTGGCAGGTAGCCCATTC | 13561 |
| 48-SP-E70 | GCACTGGCAGGTAGCCCATT | 13560 |
| 54-SP-E55 | AGGATGCTACCCGTAAGGAA | 114709 |
| 55-SP-E55 | CCTTACGGGTAGCATCCTGT | 114716 |
| 56-SP-E55 | AACAACTGCCAATGTCCTAC | 114717 |
| 57-SP-E55 | ATTACTGCAACAGTTCCCCC | 114738 |
| 58-SP-E55 | GCAACAGTTCCCCCTGGACC | 114736 |
| 59-SP-E55 | TTCTAGGAGCCTTTCCTTAC | 114710 |
| 60-SP-E55 | AGGCTCCTAGAAGACTCCAA | 114700 |
| 61-SP-E55 | GGTAGCATCCTGTAGGACAT | 114719 |
| 62-SP-E55 | ACCTGGAAAAGTTTCTTGCC | 114728 |
| 63-SP-E55 | GCCAGGCAAGAAACTTTTCC | 114730 |

All tested gRNAs can be used for an HDR/correction based editing approach. Single gRNAs targeting the splice acceptors can be used to induce exon skipping to restore the reading frame of the DMD gene. Selected pairs of gRNAs can be used to make deletions in the DMD gene that restore the reading frame. Selected pairs of gRNAs can be used to make deletions that simulate patient mutations and can be used to generate model DMD mutant lines.

Various Cas orthologs were evaluated for cutting. SP, NM, ST, SA, and Cpf1 gRNAs were delivered as RNA, expressed from the U6 promoter in plasmids, or expressed from the U6 promoter in lentivirus. The corresponding Cas protein was either knocked into the cell line of interest and constitutively expressed, delivered as mRNA, or delivered as protein. The activity of the gRNAs in all the above mentioned formats were evaluated using TIDE analysis or next generation sequencing in HEK293T cells, K562 cells, or induced pluripotent stem cells (iPSCs).

Overall, it was determined that most gRNAs tested induced cutting. However, the amount of cutting was highly dependent on the Cas protein tested. It was found that, generally, SP Cas9 gRNAs induce the highest levels of cutting with SA Cas9 gRNAs inducing the second highest level of cutting. Generally, it is beneficial to select gRNAs for therapeutic application that have the highest cutting efficiency possible. However, for an iPSC based therapy, the cutting efficiency is not as important. iPSCs are highly proliferative and make it simple to isolate a clonal population of cells with the desired edit, even when the editing efficiency is less than 10%.

Introduction of the defined therapeutic modifications described above represents a novel therapeutic strategy for the potential amelioration of DMD, as further described and illustrated herein.

Example 1—CRISPR/SPCas9 Target Sites for the Dystrophin Gene

Regions of the dystrophin gene were scanned for target sites. Each area was scanned for a protospacer adjacent motif (PAM) having the sequence NRG. gRNA 20 bp spacer sequences corresponding to the PAM were identified, as shown in SEQ ID NOs: 1-467,030. gRNA 19 bp spacer sequences corresponding to the PAM were identified, as shown in SEQ ID NOs: 1,410,430-1,410,472 of the Sequence Listing.

Example 2—CRISPR/SACas9 Target Sites for the Dystrophin Gene

Regions of the dystrophin gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 467,031-528,196 of the Sequence Listing.

Example 3—CRISPR/STCas9 Target Sites for the Dystrophin Gene

Regions of the dystrophin gene were scanned for target sites. Each area was scanned for a protospacer adjacent motif (PAM) having the sequence NNAGAAW. gRNA 24 bp spacer sequences corresponding to the PAM were identified, as shown in SEQ ID NOs: 528,197-553,198 of the Sequence Listing.

Example 4—CRISPR/TDCas9 Target Sites for the Dystrophin Gene

Regions of the dystrophin gene were scanned for target sites. Each area was scanned for a protospacer adjacent motif (PAM) having the sequence NAAAAC. gRNA 24 bp spacer sequences corresponding to the PAM were identified, as shown in SEQ ID NOs: 553,199-563,911 of the Sequence Listing.

Example 5—CRISPR/NMCas9 Target Sites for the Dystrophin Gene

Regions of the dystrophin gene were scanned for target sites. Each area was scanned for a protospacer adjacent motif (PAM) having the sequence NNNNGHTT. gRNA 24 bp spacer sequences corresponding to the PAM were identified, as shown in SEQ ID NOs: 563,912-627,854 and 1,410,400-1,410,402 of the Sequence Listing.

Example 6—CRISPR/Cpf1 Target Sites for the Dystrophin Gene

Regions of the dystrophin gene were scanned for target sites. Each area was scanned for a protospacer adjacent motif (PAM) having the sequence YTN. gRNA 20-24 bp spacer sequences corresponding to the PAM were identified, as shown in SEQ ID NOs: 627,855-1,410,399 and 1,410, 403-1,410,429 of the Sequence Listing.

Example 7—Illustrative Genome Editing Strategies Targeting Exon 2

Several methods provide gRNA pairs that delete exon 2 by cutting the gene twice, one gRNA cutting at the 5' end of exon 2 and the other gRNA cutting at the 3' end of exon 2.

Example 8—Illustrative Genome Editing Strategies Targeting Exon 8

Several methods provide gRNA pairs that delete exon 8 by cutting the gene twice, one gRNA cutting at the 5' end of exon 8 and the other gRNA cutting at the 3' end of exon 8.

Example 9—Illustrative Genome Editing Strategies Targeting Exon 43

Several methods provide gRNA pairs that delete exon 43 by cutting the gene twice, one gRNA cutting at the 5' end of exon 43 and the other gRNA cutting at the 3' end of exon 43.

Example 10—Illustrative Genome Editing Strategies Targeting Exon 44

Several methods provide gRNA pairs that delete exon 44 by cutting the gene twice, one gRNA cutting at the 5' end of exon 44 and the other gRNA cutting at the 3' end of exon 44.

Example 11—Illustrative Genome Editing Strategies Targeting Exon 45

Several methods provide gRNA pairs that delete exon 45 by cutting the gene twice, one gRNA cutting at the 5' end of exon 45 and the other gRNA cutting at the 3' end of exon 45.

Example 12—Illustrative Genome Editing Strategies Targeting Exon 46

Several methods provide gRNA pairs that delete exon 46 by cutting the gene twice, one gRNA cutting at the 5' end of exon 46 and the other gRNA cutting at the 3' end of exon 46.

Example 13—Illustrative Genome Editing Strategies Targeting Exon 50

Several methods provide gRNA pairs that delete exon 50 by cutting the gene twice, one gRNA cutting at the 5' end of exon 50 and the other gRNA cutting at the 3' end of exon 50.

Example 14—Illustrative Genome Editing Strategies Targeting Exon 51

Several methods provide gRNA pairs that delete exon 51 by cutting the gene twice, one gRNA cutting at the 5' end of exon 51 and the other gRNA cutting at the 3' end of exon 51.

Example 15—Illustrative Genome Editing Strategies Targeting Exon 52

Several methods provide gRNA pairs that delete exon 52 by cutting the gene twice, one gRNA cutting at the 5' end of exon 52 and the other gRNA cutting at the 3' end of exon 52.

Example 16—Illustrative Genome Editing Strategies Targeting Exon 53

Several methods provide gRNA pairs that delete exon 53 by cutting the gene twice, one gRNA cutting at the 5' end of exon 53 and the other gRNA cutting at the 3' end of exon 53.

Example 17—Illustrative Genome Editing Strategies Targeting Exon 70

Several methods provide gRNA pairs that delete exon 70 by cutting the gene twice, one gRNA cutting at the 5' end of exon 70 and the other gRNA cutting at the 3' end of exon 70.

Example 18—Illustrative Genome Editing Strategies Targeting Exons 45-53

Several methods provide gRNA pairs that delete exons 45-53 by cutting the gene twice, one gRNA cutting at the 5' end of exon 45 and the other gRNA cutting at the 3' end of exon 53.

Example 19—Illustrative Genome Editing Strategies Targeting Exons 45-55

Several methods provide gRNA pairs that delete exons 45-55 by cutting the gene twice, one gRNA cutting at the 5' end of exon 45 and the other gRNA cutting at the 3' end of exon 55.

Example 20—Bioinformatics Analysis of the Guide Strands

Candidate guides were screened and selected in a multi-step process that involved both theoretical binding and experimentally assessed activity. By way of illustration, candidate guides having sequences that match a particular on-target site, such as a site within or near the dystrophin gene, with adjacent PAM can be assessed for their potential to cleave at off-target sites having similar sequences, using one or more of a variety of bioinformatics tools available for assessing off-target binding, as described and illustrated in more detail below, in order to assess the likelihood of effects at chromosomal positions other than those intended. Candidates predicted to have relatively lower potential for off-target activity can then be assessed experimentally to measure their on-target activity, and then off-target activities at various sites. Preferred guides have sufficiently high on-target activity to achieve desired levels of gene editing at the selected locus, and relatively lower off-target activity to reduce the likelihood of alterations at other chromosomal loci. The ratio of on-target to off-target activity is often referred to as the "specificity" of a guide.

For initial screening of predicted off-target activities, there are a number of bioinformatics tools known and publicly available that can be used to predict the most likely off-target sites; and since binding to target sites in the CRISPR/Cas9 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr.bme.gatech.edu) compiles such similarities. Other bioinformatics tools include, but are not limited to, GUIDO, autoCOSMID, and CCtop.

Bioinformatics were used to minimize off-target cleavage in order to reduce the detrimental effects of mutations and chromosomal rearrangements. Studies on CRISPR/Cas9 systems suggested the possibility of high off-target activity due to nonspecific hybridization of the guide strand to DNA sequences with base pair mismatches and/or bulges, particularly at positions distal from the PAM region. Therefore, it is important to have a bioinformatics tool that can identify potential off-target sites that have insertions and/or deletions between the RNA guide strand and genomic sequences, in addition to base-pair mismatches. The bioinformatics-based tool, COSMID (CRISPR Off-target Sites with Mismatches, Insertions and Deletions) was therefore used to search genomes for potential CRISPR off-target sites (available on the web at crispr.bme.gatech.edu). COSMID output ranked lists of the potential off-target sites based on the number and location of mismatches, allowing more informed choice of target sites, and avoiding the use of sites with more likely off-target cleavage.

Additional bioinformatics pipelines were employed that weigh the estimated on- and/or off-target activity of gRNA targeting sites in a region. Other features that can be used to predict activity include information about the cell type in question, DNA accessibility, chromatin state, transcription factor binding sites, transcription factor binding data, and other CHIP-seq data. Additional factors are weighed that predict editing efficiency, such as relative positions and directions of pairs of gRNAs, local sequence features and micro-homologies.

Example 21—Testing of Preferred Guides in Cells for On-Target Activity

The gRNAs predicted to have the lowest off-target activity will then be tested for on-target activity in epithelial cells derived from a human embryonic kidney, HEK 293 Ts, by transient transfection and evaluated for indel frequency using TIDE or next generation sequencing. TIDE is a web tool to rapidly assess genome editing by CRISPR-Cas9 of a target locus determined by a guide RNA (gRNA or sgRNA). Based on the quantitative sequence trace data from two standard capillary sequencing reactions, the TIDE software quantifies the editing efficacy and identifies the predominant types of insertions and deletions (indels) in the DNA of a targeted cell pool. See Brinkman et al, Nucl. Acids Res. (2014) for a detailed explanation and examples. Next-generation sequencing (NGS), also known as high-throughput sequencing, is the catch-all term used to describe a number of different modern sequencing technologies including: Illumina (Solexa) sequencing, Roche 454 sequencing, Ion torrent: Proton/PGM sequencing, and SOLiD sequencing. These recent technologies allow one to sequence DNA and RNA much more quickly and cheaply than the previously used Sanger sequencing, and as such have revolutionized the study of genomics and molecular biology. HEK 293 Ts are a good model system for gene correction in iPSCs because both cell types are known to have loose chromatin structures.

Chromatin is organizing by coiling into discrete structures called nucleosomes. This coiling influences accessibility of the genomic material to transcriptional machinery. Regions of the genome that are open are termed euchromatin, while regions of tight coiling are called heterochromatin. It is a well accepted paradigm that stem cells have a generally loose chromatin conformation and as cells differentiate into more specialized cell types, certain regions of the genome become closed forming heterochromatin (Sims, R. J. and D. Reinberg (2009). "Stem cells: Escaping fates with open states." Nature 460(7257): 802-803).

Example 22—Testing in Relevant Model Cell Lines

Once all of the guide RNAs are evaluated individually and effective gRNAs are identified, all permutations of pairs of gRNAs will be tested in relevant model cell lines for their ability to modify the DNA sequence of the dystrophin gene that would be predicted to restore the dystrophin reading frame. Myoblast and iPSC cell lines with modifications similar or identical to those found in patient samples were generated. The cells are treated with the different individual and pairwise combinations of gRNAs and a donor DNA template, if and as applicable. Samples can then be evaluated for restoration of dystrophin expression using one or more biological methods known to those skilled in the art, for example, an enzyme-linked immunosorbent assay (ELISA) that specifically recognizes the C terminus of the dystrophin protein (note that truncated proteins do not contain an intact C terminus). The pairs of gRNAs that restore dystrophin expression can then be further evaluated by an additional biologic technique, such as Western blot to confirm expression of the appropriate size of dystrophin protein.

Example 23—Testing Different Approaches for HDR Gene Editing

After testing the gRNAs for both on-target activity and off-target activity, exon correction and knock-in strategies will be tested for HDR gene editing.

For the exon correction approach, donor DNA template will be provided as a short single-stranded oligonucleotide, a short double-stranded oligonucleotide (PAM sequence intact/PAM sequence mutated), a long single-stranded DNA molecule (PAM sequence intact/PAM sequence mutated) or a long double-stranded DNA molecule (PAM sequence intact/PAM sequence mutated). In addition, the donor DNA template will be delivered by AAV.

For the DNA knock-in approach, a single-stranded or double-stranded DNA having homologous arms to the Xp21.2 locus can include 40 nt or more of a first target exon (the first coding exon) of the dystrophin gene, the complete coding DNA sequence (CDS) of the dystrophin gene and 3'UTR of the dystrophin gene, and at least 40 nt of the following intron. The single-stranded or double-stranded DNA having homologous arms to the Xp21.2 locus can include 80 nt or more of a first target exon (the first coding exon) of the dystrophin gene, the complete coding DNA sequence (CDS) of the dystrophin gene and 3'UTR of the dystrophin gene, and at least 80 nt of the following intron. The single-stranded or double-stranded DNA having homologous arms to the Xp21.2 locus can include 100 nt or more of a first target exon (the first coding exon) of the dystrophin gene, the complete coding DNA sequence (CDS) of the dystrophin gene and 3'UTR of the dystrophin gene, and at least 100 nt of the following intron. The single-stranded or double-stranded DNA having homologous arms to the Xp21.2 locus can include 150 nt or more of the first target exon (the first coding exon) of the dystrophin gene, the complete coding DNA sequence (CDS) of the dystrophin gene and 3'UTR of the dystrophin gene, and at least 150 nt of the following intron. The single-stranded or double-stranded DNA having homologous arms to the Xp21.2 locus can include 300 nt or more of the first target exon (the first coding exon) of the dystrophin gene, the complete coding DNA sequence (CDS) of the dystrophin gene and 3'UTR of the dystrophin gene, and at least 300 nt of the following intron. The single-stranded or double-stranded DNA having homologous arms to the Xp21.2 locus can include 400 nt or more of the first target exon (the first coding exon) of the dystrophin gene, the complete CDS of the dystrophin gene and 3'UTR of the dystrophin gene, and at least 400 nt of the following intron. Alternatively, the DNA template will be delivered by AAV.

For the cDNA knock-in approach, a single-stranded or double-stranded cDNA can include 40 nt or more of a single exon target of the dystrophin gene. The single-stranded or double-stranded cDNA can include 80 nt or more of a single exon target of the dystrophin gene. The single-stranded or double-stranded cDNA can include 100 nt or more of a single exon target of the dystrophin gene. The single-stranded or double-stranded cDNA can include 150 nt or more of a single exon target of the dystrophin gene. The single-stranded or double-stranded cDNA can include 300 nt or more of a single exon target of the dystrophin gene. The single-stranded or double-stranded cDNA can include 400 nt or more of a single exon target of the dystrophin gene. Alternatively, the DNA template will be delivered by AAV.

For the cDNA knock-in approach, a single-stranded or double-stranded cDNA can include 40 nt or more of a multiple exon target of the dystrophin gene. The single-stranded or double-stranded cDNA can include 80 nt or more of a multiple exon target of the dystrophin gene. The single-stranded or double-stranded cDNA can include 100 nt or more of a multiple exon target of the dystrophin gene. The single-stranded or double-stranded cDNA can include 150 nt or more of a multiple exon target of the dystrophin gene. The single-stranded or double-stranded cDNA can include 300 nt or more of a multiple exon target of the dystrophin gene. The single-stranded or double-stranded cDNA can include 400 nt or more of a multiple exon target of the dystrophin gene. Alternatively, the DNA template will be delivered by AAV.

Example 24—Re-Assessment of Lead CRISPR-Cas9/DNA Donor Combinations

After testing the different strategies for HDR gene editing, the lead CRISPR-Cas9/DNA donor combinations will be re-assessed in therapeutically relevant cells for efficiency of deletion, recombination, and off-target specificity. Cas9 mRNA or RNP will be formulated into lipid nanoparticles for delivery, sgRNAs will be formulated into nanoparticles or delivered as AAV, and donor DNA will be formulated into nanoparticles or delivered as AAV.

Example 25—In Vivo Testing in Relevant Animal Model

After the CRISPR-Cas9/DNA donor combinations have been re-assessed, the lead formulations will be tested in vivo in a therapeutically relevant mouse model.

Culture in human cells allows direct testing on the human target and the background human genome, as described above.

Preclinical efficacy and safety evaluations can be observed through engraftment of modified mouse or human cells in a therapeutically relevant mouse model. The modified cells can be observed in the months after engraftment.

Figure 3A:
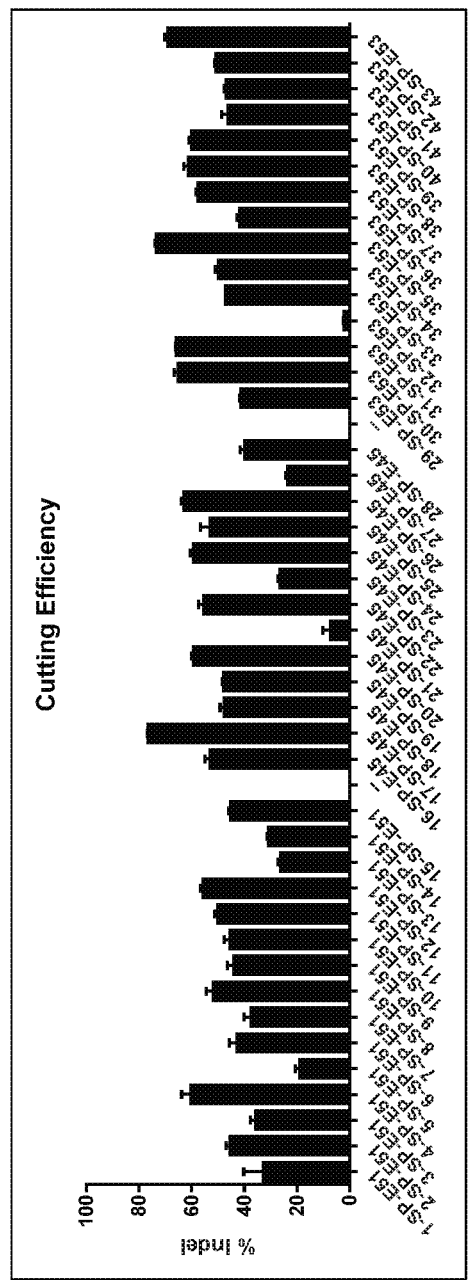
FIG. 3A describes the cutting efficiency of *S. pyogenes* gRNAs in HEK293 Ts targeting Exons 45, 51, and 53 of the dystrophin gene.
Figure 3B:
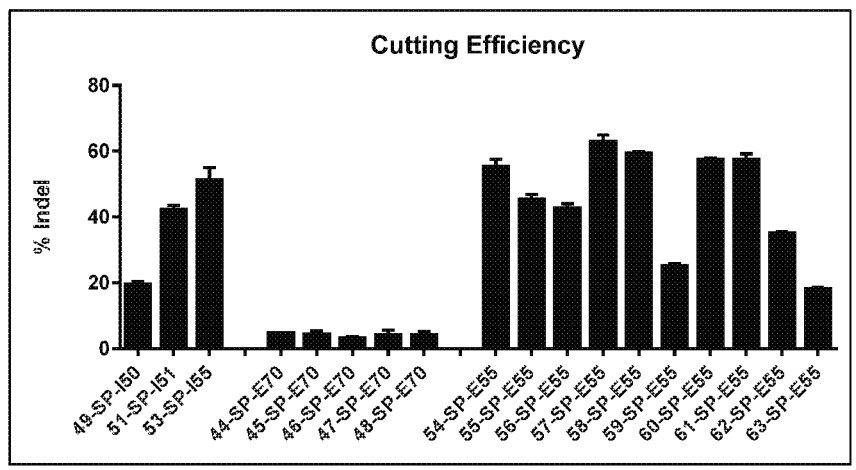
FIG. 3B describes the cutting efficiency of *S. pyogenes* gRNAs in HEK293 Ts targeting Exons 55 and 70 of the dystrophin gene.

Example 26—Cutting Efficiency of S. pyogenes gRNAs Targeting Exons 45, 51, 53, 55, and 70 in the DMD Gene S. pyogenes (SP) gRNAs were tested that target Exons 45, 51, 53, 55, and 70 in the DMD gene (FIGS. 3A-3B). Each of Exons 45, 51, 53, 55, and 70 may be edited using an HDR/correction based approach.

The SP gRNAs were cloned into plasmids that co-express the SP Cas protein. The plasmids were transfected into HEK293T cells using lipofectamine 2000. Cells were harvested 48 hours post transfection, the genomic DNA was isolated, and cutting efficiency was evaluated using TIDE analysis. Data was compiled from one experiment containing 3-4 replicates (N=3 to 4). Data was plotted as mean and SEM.

The data from FIGS. 3A-3B indicate that most gRNAs cut with efficiencies greater than 50% in HEK293T cells.

Example 27—Cutting Efficiency of gRNAs Targeting the Splice Acceptor of Exons 43, 44, 45, 46, 50, 51, 52, 53, and 55 in the DMD Gene A viable option for treating DMD is to induce exon skipping to restore the reading frame of the DMD gene. To induce exon skipping, the gene editing approach must remove the AG sequence just upstream of the exon that is recognized by endogenous splicing machinery. When a single gRNA induces a double stranded break, the cell will repair the break. Some fraction of the time, the endogenous repair machinery will make a mistake and either insert or delete bases adjacent to the cut site. The gRNAs that mutate the AG sequence are likely to induce exon skipping at this site as the splicing machinery will no longer be able to recognize this site as a splice acceptor site and will skip to the next splice acceptor of the neighboring exon.

Figure 4B:
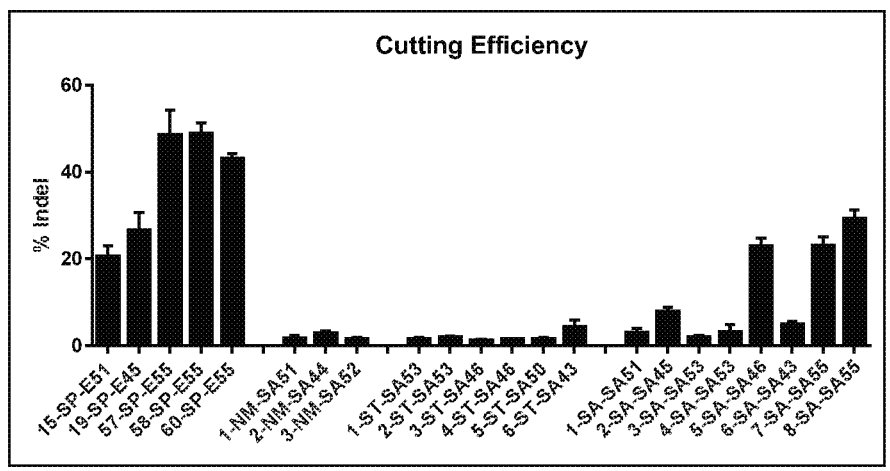
FIG. 4B describes the cutting efficiency of *N. meningitides, S. thermophiles*, and *S. aureus* gRNAs in HEK293 Ts targeting the splice acceptor of Exons 43, 44, 45, 46, 50, 51, 52, 53 and 55 of the dystrophin gene.

S. pyogenes (SP), S. aureus (SA), S. thermophiles (ST), N. Meningitidis (NM), and Cpf1 gRNAs were designed and tested that target the splice acceptor of Exons 43, 44, 45, 46, 50, 51, 52, 53, and 55 in the DMD gene (FIGS. 4A, 4B, and 4C).

SP gRNAs were designed to target the splice acceptor of nine exons in the DMD gene. The gRNAs were ordered as split RNA gRNAs from Integrated DNA Technologies (IDT). The split gRNAs were annealed to the tracRNA per manufacturer's instructions. The annealed split gRNAs were then transfected into HEK293T cells that stably express the SP Cas9 protein cells using RNAiMax. Cells were harvested 48 hours post transfection, the genomic DNA was isolated, and cutting efficiency was evaluated using TIDE analysis (FIG. 4A). Data was compiled between two independent experiments each containing 3 replicates (N=2 to 6). Data was plotted as mean and SEM.

NM, ST, and SA gRNAs were designed to target the splice acceptor of nine exons. The gRNAs were cloned into plasmids that co-express the Cas protein of interest along with the corresponding gRNA. The plasmids were transfected into HEK293T cells using lipofectamine 2000. Cells were harvested 48 hours post transfection, the genomic DNA was isolated, and cutting efficiency was evaluated using TIDE analysis (FIG. 4B). Data was compiled between 2-4 independent experiments each containing 3 replicates (N=6 to 12). Data was plotted as mean and SEM.

Cpf1 gRNAs were designed to target the splice acceptor of nine exons in the DMD gene. The gRNAs were cloned into plasmids that express the gRNA. HEK293T were co-transfected with the gRNA plasmid of interest and a second plasmid expressing Cpf1 using lipofectamine 2000. Cells were harvested 48 hours post transfection, the genomic DNA was isolated, and cutting efficiency was evaluated using TIDE analysis (FIG. 4C). Data was compiled between two independent experiments each containing 3 replicates (N=3 to 6). Data was plotted as mean and SEM.

Example 28—Cutting Efficiencies and Splice Acceptor Knock-Out Efficiencies of gRNAs Targeting Exons 43, 44, 45, 46, 50, 51, 52, 53, and 55 in the DMD Gene Many of the splice acceptor targeting gRNAs cut efficiently at the desired splice site. To evaluate if the gRNA effectively knocked out the desired AG sequence, PCR amplicons around the cut site were submitted for next generation sequencing. The indel percentage reads where the splice acceptor site was removed were quantified (FIGS. 5A-B and FIG. 6). A number of promising gRNAs were identified including, but not limited to: 8-SA-SA55, 3-SP-SA45, 31-SP-SA50, and 40-SP-SA55 that remove the splice acceptor site in a large proportion of the reads.

S. pyogenes gRNAs were designed to target the splice acceptor of nine exons in the DMD gene. The gRNAs were ordered as split RNA gRNAs from IDT. The split gRNAs were annealed to the tracRNA per manufacturer's instructions. The annealed split gRNAs were transfected into HEK293T cells that stably express the S. pyogenes Cas9 protein cells using RNAiMax. Cells were harvested 48 hours post transfection, the genomic DNA was isolated, and the desired 100-250 bp PCR amplicons surrounding the desired splice acceptors were submitted for next generation sequencing. Data was compiled between two independent experiments each containing 3 replicates (N=6). Averages were presented as population averages (FIGS. 5A-B).

N. meningitides (NM), S. thermophiles (ST), and S. aureus (SA) gRNAs were designed to target the splice acceptor of nine exons. The gRNAs were cloned into plasmids that co-expresses the Cas protein of interest along with the corresponding gRNA. The plasmids were transfected into HEK293T cells using lipofectamine 2000. Cells were harvested 48 hours post transfection, the genomic DNA was isolated, and the desired 100-250 bp PCR amplicons surrounding the desired splice acceptors were submitted for next generation sequencing. Data was compiled between two independent experiments each containing 3 replicates (N=6). Averages were presented as population averages (FIG. 6).

Example 29—Cutting Efficiency of gRNAs Targeting the Regions Surrounding Exons 44, 45, 52, and 54 of the DMD Gene To effectively evaluate editing approaches, it is important to access patient cell lines for in-vitro testing. However, patient material may be difficult to access and there can be large patient-to-patient variation between samples. Therefore, it was important to create DMD mutant cell lines that mimic common patient mutations. This allows the researcher to test the efficacy of a repair strategy in the same background to ensure that variations in editing efficiency are not patient specific. To address this, a variety of gRNAs were designed that can be paired to create common deletions found in DMD patients (Δ52, Δ44, Δ45, and Δ54). The resulting cell lines can be corrected using either an HDR or exon skipping approach. It is important to note, that these gRNAs can be used for either the creation of the model line or an HDR based correction of mutations of interest.

Figure 7A:
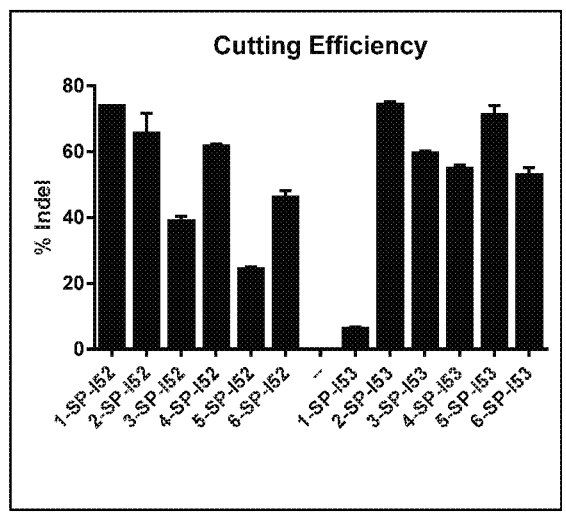
FIG. 7A describes the cutting efficiency of *S. pyogenes* gRNAs in HEK293T cells where the gRNAs target the regions surrounding Exon 52 of the dystrophin gene.
Figure 7B:
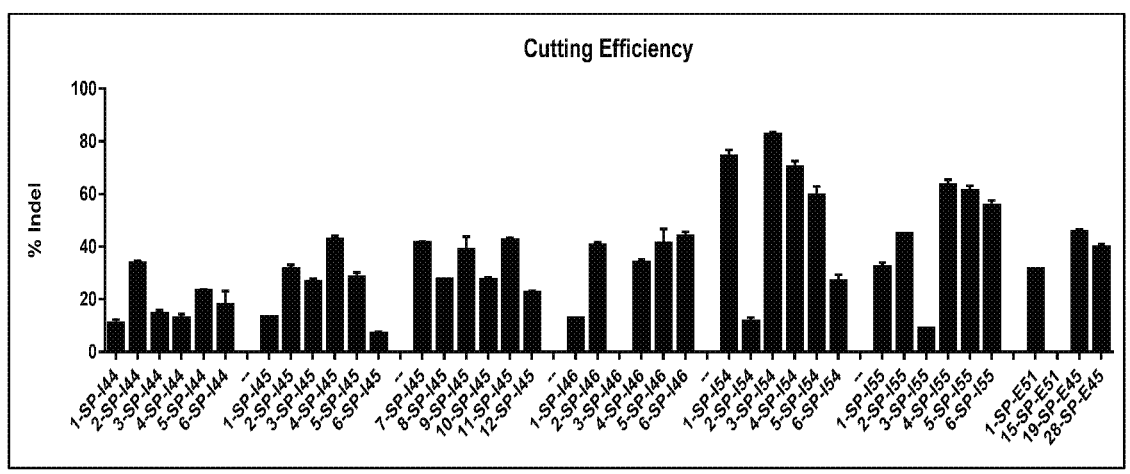
FIG. 7B describes the cutting efficiency of *S. pyogenes* gRNAs in HEK293T cells where the gRNAs target the regions surrounding Exons 44, 45, and 54 of the dystrophin gene.
Figure 8A:
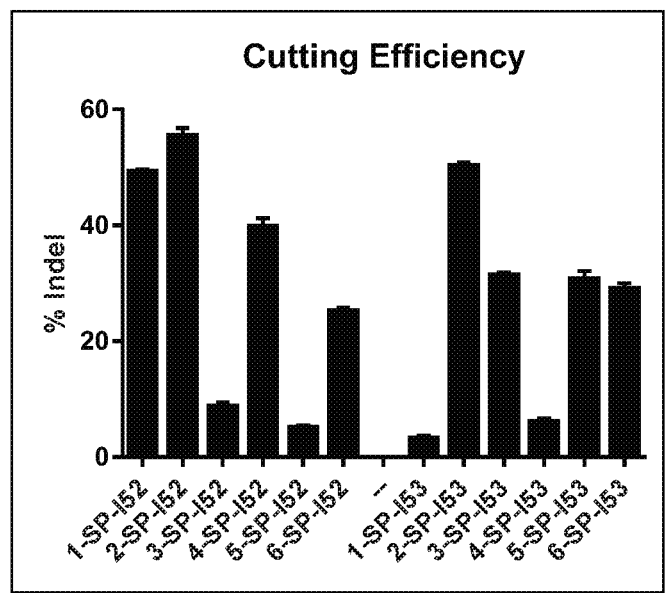
FIG. 8A describes the cutting efficiency of *S. pyogenes* gRNAs in iPSCs where the gRNAs target the regions surrounding Exon 52 of the dystrophin gene.
Figure 8B:
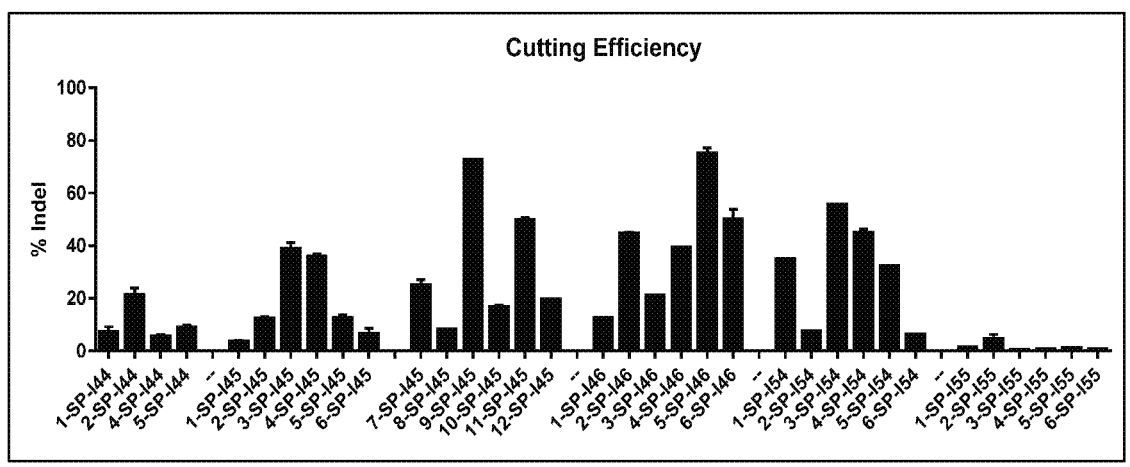
FIG. 8B describes the cutting efficiency of *S. pyogenes* gRNAs in iPSCs where the gRNAs target the regions surrounding Exons 44, 45, and 54 of the dystrophin gene.

The region (100 bp-1 kb upstream and downstream of the exon of interest) was screened using gRNA design software. The best 6 gRNAs based on fewest predicted off target effects were selected on each side of the exon of interest (such as Exons 44, 45, 52, and 54 of the DMD gene). The gRNAs were first evaluated in HEK293 Ts for cutting efficiency (FIGS. 7A-7B) and confirmed for cutting efficiency in iPSC (FIGS. 8A-8B).

Single S. pyogenes gRNAs around exons 44, 45, 52, and 54 were selected. The gRNAs were ordered as split gRNA from IDT. Split gRNAs were annealed to the tracer sequence using manufacturer's instructions.

The annealed gRNAs were transfected into HEK293T that stably express the SP Cas9 protein cells using RNAiMax. Cells were harvested 48 hours post transfection, the genomic DNA was isolated, and cutting efficiency was evaluated using TIDE analysis (FIGS. 7A-7B). Data was compiled from one experiment each containing 3 replicates (N=1 to 3). Data was plotted as mean and SEM.

The annealed gRNAs were also subsequently complexed with Cas9 protein to form a ribonucleoprotein complex (RNP). The RNPs were transfected into iPSCs (DiPS 1016SevA) using RNAiMax. Cells were harvested 48 hours post transfection, the genomic DNA was isolated, and cutting efficiency was evaluated using TIDE analysis (FIG. 8A-8B). Data was compiled from one experiment containing 3 replicates (N=1 to 3). Data was plotted as mean and SEM.

Single S. pyogenes gRNAs around exons 44, 45, 52, and 54 were selected. The gRNAs were ordered as split gRNA from IDT. Split gRNAs were annealed to the tracer sequence using manufacturer's instructions. The gRNAs were transfected into HEK293T that stably express the SP Cas9 protein cells using RNAiMax. The same gRNAs were also complexed with Cas9 protein to form a ribonucleoprotein complex (RNP). The RNPs were transfected into iPSCs (DiPS 1016SevA) using RNAiMax. Cells were harvested 48 hours post transfection, the genomic DNA was isolated, and cutting was evaluated using TIDE analysis. Data was compiled from multiple experiments. Only average values were plotted.

Figure 9:
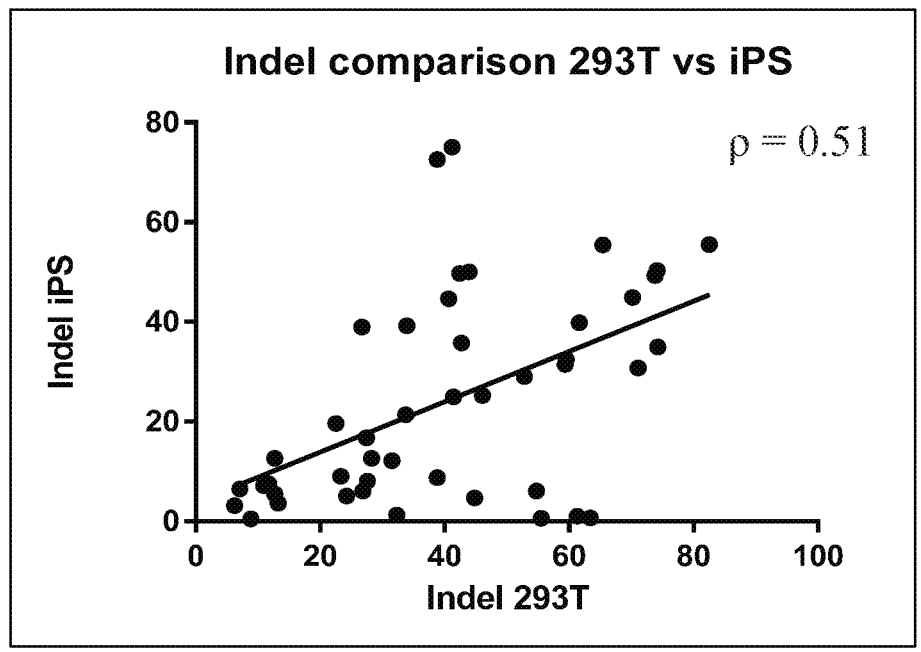
FIG. 9 describes the cutting efficiency comparison of *S. pyogenes* gRNAs in HEK293T cells and iPSCs where the gRNAs target the regions surrounding Exons 44, 45, 52, and 54 of the dystrophin gene.

There was a high correlation between editing efficiency in HEK293T cells and iPSCs with a Pearson correlation coefficient of 0.51 overall. As such, screening in HEK293T cells was considered to be a good surrogate for our therapeutic cell line of interest—iPSCs (FIG. 9).

Example 30—Clonal Analysis of Clonal Deletion Events gRNAs with cutting efficiencies over 20% in iPSCs were identified in each intron of interest except for intron 55. Single gRNAs were selected with the best cutting efficiencies to make the desired deletions.

Figure 10A:
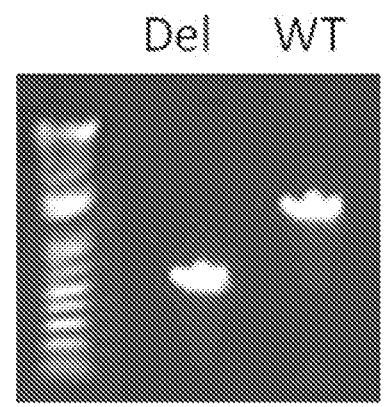

Two pairs of gRNAs were used to create clonal Δ52 cell lines (1-SP-I52+2-SP-I53 and 2-SP-I52+2-SP-I53). Out of 261 total clones screened, 57 had the desired deletion as accessed by PCR analysis (FIGS. 10A, 10C).

To confirm the presence of the expected Δ52 deletion, genomic DNA from each clone of interest was harvested. PCR primers flanking the deletion were designed. Since the deletion was small (<900 bp), a single pair of primers could be used to detect the deletion. This would result in a smaller deletion band (~500 bp) or a wild-type (WT) band (~1000 bp). A representative gel of the deletion (del) or wild type (WT) product is shown in FIG. 10A.

The deletion even was confirmed in seven clones by submitting the deletion PCR product for Sanger sequencing (7/7 clones had the predicted deletion event with small insertions and deletions (FIGS. 11A-B). The deletion bands from seven clones (PCRs generated in FIG. 8A) were gel prepped and submitted for Sanger sequencing. Two clones created using gRNA 1-SP-I52 and 2-SP-I53 were sequenced and aligned to the predicted deletion product (assuming that S. pyogenes Cas9 cuts 3BP from the 3' end of the gRNA (FIG. 11A). Five clones created using gRNA 2-SP-I52 and 2-SP-I53 were sequenced and aligned to the predicted deletion product (assuming that S. pyogenes Cas9 cuts 3BP from the 3' end of the gRNA (FIG. 11B).

Figure 10B:
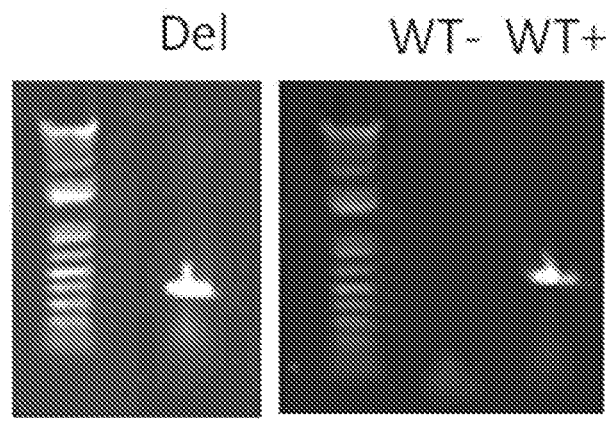

Similarly, two pairs of gRNAs were used to create clonal Δ44 cell lines (2-SP-I44+3-SP-I45 and 2-SP-I44+4-SP-I45). Out of 256 total clones screened, 16 had the desired deletion as accessed by PCR analysis (FIGS. 10B, 10C).

To confirm the presence of the expected Δ44 deletion, genomic DNA from each clone of interest was harvested. Since the Δ44 gRNAs produce a larger deletion compared to the Δ52 gRNAs, two pairs of PCR primers were designed to either detect a deletion band or WT band. The expected deletion band was ~400 bp and the expected WT band was ~500 bp. A representative gel of the deletion (del), wild type product (WT+), and a negative sample amplified with the wild type primers (WT−) is shown in FIG. 10B.

Example 31—Lentiviral Screen

To identify a large spectrum of pairs of gRNAs able to induce Exon51 skipping, we conducted a large scale lentiviral screen. Intron 51 and Intron 52 genomic sequence were submitted for analysis using a gRNA design software. The resulting list of gRNAs were narrowed to about 3000 left and 3000 right gRNAs adjacent to the Exon 51 splice acceptor. The list was narrowed based on uniqueness of sequence (only gRNAs without a perfect match somewhere else in the genome were screened) and minimal predicted off targets. A left gRNA paired with a right gRNA should induce Exon 51 skipping. The 6000 gRNAs were cloned into a lentiviral vector that expressed each gRNA of interest from the U6 promoter and confers puromycin resistance. K562 cells were transduced with the virus at an MOI 2 and selected with puromycin to obtain a population of cells that were expressing a gRNA of interest. These cells were then nucleofected with Cas9 mRNA to induce a transient period of cutting. After 7 days, the cells were pelleted and the genomic DNA was extracted. The genomic DNA was enriched for the region of interest around Exon 51 using hybrid capture. The enriched DNA was submitted for next generation sequencing (FIGS. 19A-19VV).

Example 32—In Vitro Transcribed (IVT) gRNA Screen

To identify a large spectrum of pairs of gRNAs able to induce Exon 45 skipping, an in vitro transcribed (IVT) gRNA screen was conducted. Intron 45 and Intron 46 genomic sequence was submitted for analysis using a gRNA design software. The resulting list of gRNAs were narrowed to a list of about 100 left and about 100 right gRNAs based on uniqueness of sequence (only gRNAs without a perfect match somewhere else in the genome were screened) and minimal predicted off targets. This set of gRNAs were in vitro transcribed, and transfected using messenger Max into HEK293T cells that stably express Cas9. Cells were harvested 48 hours post transfection, the genomic DNA was

Example 33—Partial cDNA Knockin Between Exons 45-55 of the DMD Gene

Figure 13A:
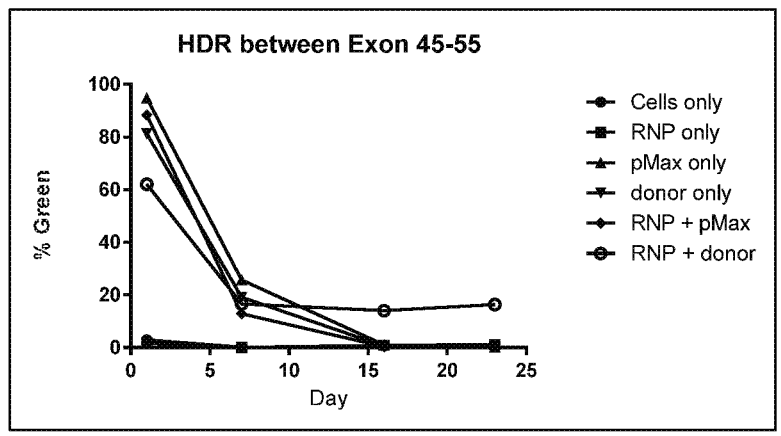
FIG. 13A describes the homology directed repair (HDR) between Exon 45-55 of the dystrophin gene.
Figure 13B:
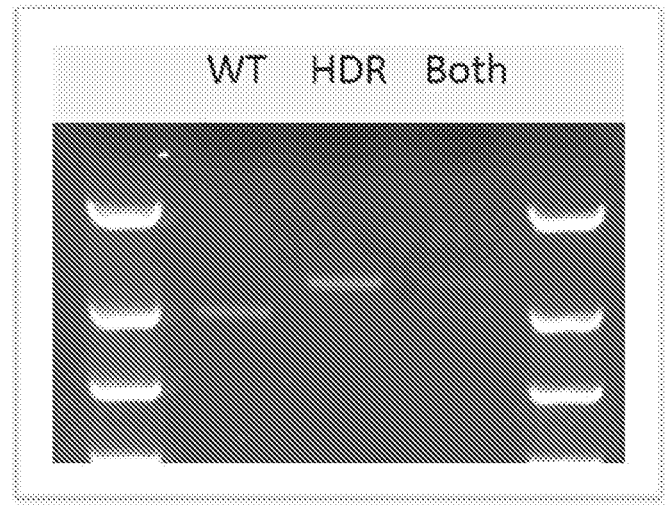
FIG. 13B depicts the PCR confirmation of HDR at the Exon 45-55 locus of the dystrophin gene.

Another approach for correcting the DMD gene is a partial cDNA knock-in. As proof of principle, a study was conducted to replace the region Exon 45-55 of the DMD gene (which could treat up to 62% of DMD patients). The cDNA for Exon 45-55 is 3.2 kb. Two solid phase synthesized gRNAs [one in Exon 45 (SEQ ID NO. 1410449) and a second in Exon 55 (SEQ ID NO 114738)] from Trilink were used for cutting. The two trilink gRNAs were complexed with Cas9 protein and nucleofected into iPSCs along with a plasmid donor. The plasmid donor was designed to have a 3.2 kb cassette (same size as the desired cDNA knock-in) that constitutively expressed GFP with 1 kb homology arms on each side to induce integration into the Exon 45 to 55 site. The cells were tracked over 23 days. All experimental conditions were nucleofected with high efficiency (over 60%); however, only GFP expression from cells that received the donor and gRNA stabilized over time, indicating that HDR occurred in about 16 percent of cells (FIG. 13A). The genomic DNA from these samples was isolated and tested for site specific integration of the donor construct. Samples were amplified with primers specific to the WT allele or the desired knock-in allele. As expected, both the WT and knock-in allele could be detected (FIG. 13B).

Example 34—Internally Deleted Yet Functional Dystrophin Protein

As proof of concept, it was demonstrated that we can edit in iPSC, isolate a clonal population of edited cells, and differentiate those cells down the myogenic lineage to produce an internally deleted yet functional dystrophin protein.

One attractive method for correcting the DMD gene is to create a 445-55 deletion. This deletion maintains the DMD reading frame and can restore expression of dystrophin in about 62% of DMD patients. To create the desired 445-55 deletion, two published SP gRNAs (CR6: SEQ ID NO: 1,410,475 and CR36: SEQ ID NO: 91033) were cloned into plasmids that also express SP Cas9 T2A orange florescent protein (OFP).

| gRNA | gRNA sequence | PAM |
|---|---|---|
| CR6 | GGGGCTCCACCCTCACGAGT | GGG |
| CR36 | GCCTTCTTTATCCCCTATCG | AGG |

These two plasmids were co transfected into iPSCs using Mirus LT1 transfection reagent. Two days later the cells expressing Cas9 as indicated by OFP expression were isolated using florescence activated cell sorting (FACS). The cells were seeded at a low density and allowed to grow for 7-10 days until single cell clones appeared in the dishes. The clones were picked manually under a microscope and transferred into 96 well plates. Once the cells reached confluence, the samples were passaged 1:2 and genomic DNA was isolated from the remaining cells.

To identify clones with the desired deletion, a three primer PCR assay was designed (FIGS. 14A and 14B). The assay allows for detection of a wild type (WT) and deletion band in the same PCR reaction. Using this assay, we identified 26/100 clones that had the editing event (FIG. 14C).

Figure 15:
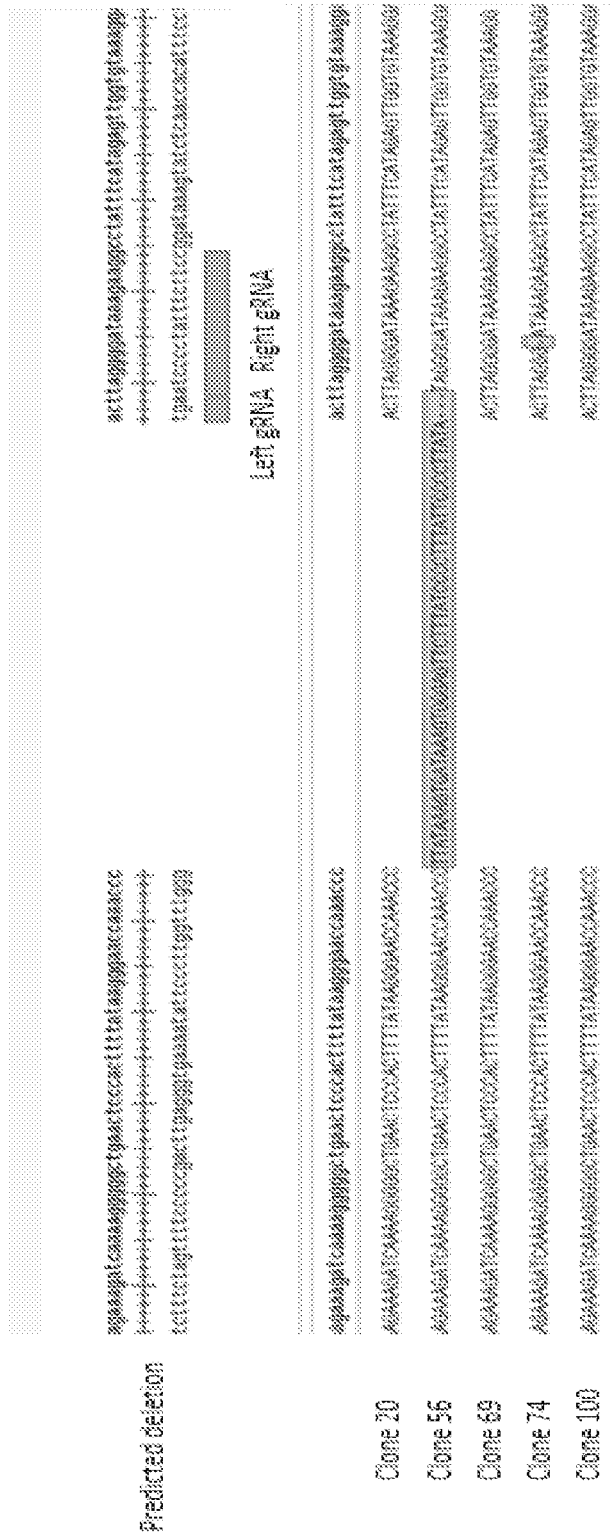
FIG. 15 describes 5 clones that have the desired 445-55 deletion. SEQ ID NO: 1420002 corresponds to clone 20. SEQ ID NO: 1420003 corresponds to clone 56. SEQ ID NO: 1420004 corresponds to clone 69. SEQ ID NO: 1420005 corresponds to clone 74. SEQ ID NO: 1420006 corresponds to clone 100.

To further validate that the clones had the desired 445-55 deletion, 5 clones were submitted for Sanger sequencing. All five were confirmed to have the desired deletion event. One clone had an insertion, and one a single base pair deletion. The other three clones contained perfect deletion events (FIG. 15).

Figure 16A:
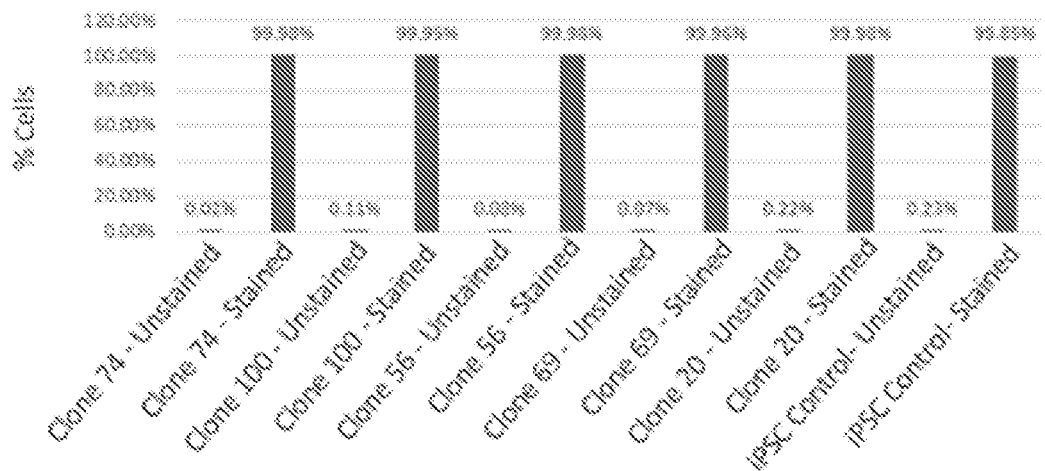
FIGS. 16A-B describes the SSEA-4 Staining and TRA-160 Staining results of the 5 clones that have the desired 445-55 deletion.
Figure 16B:
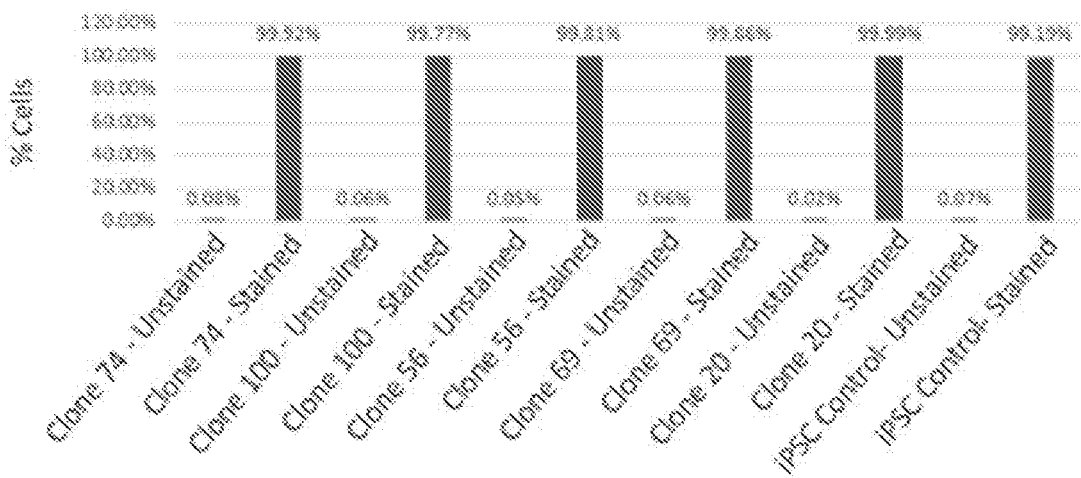

All five clones that were sequenced, were also submitted for karyotyping, and found karyotypically normal. Furthermore, all clones maintained pluripotency and stained over 99% positive for both SSEA-4 and TRA-160 (FIGS. 16A-B).

Figure 17:
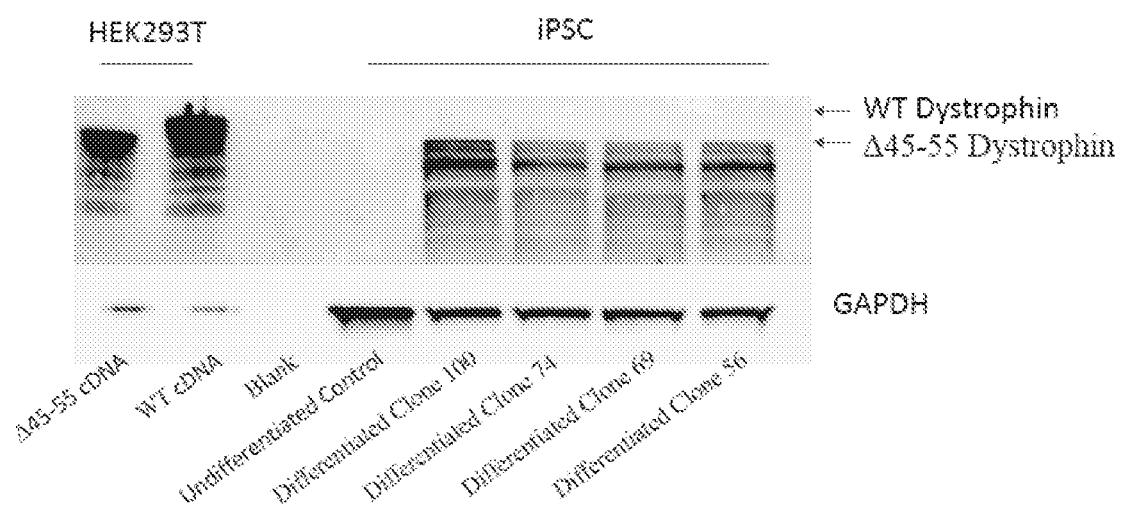
FIG. 17 depicts the expression of an internally deleted dystrophin protein for all 5 edited clones.
Figure 18:
FIG. 18 depicts myosin heavy chain staining of differentiated clone 56.

Four of the clones were then differentiated into mytotubes using the published Chal et. al protocol. [Chal et. al (2015) Differentiation of Pluripotent stem cells to muscle fiber to model Duchenne Muscular Dystrophy. Nature Biotechnology] to induce expression of dystrophin. Samples were harvested for Western blot and immuno-histo-chemistry. All five edited clones induced expression of an internally deleted dystrophin protein (FIG. 17). The sizes were compared to protein isolated from HEK293T cells transfected with control cDNA plasmids that express either the WT dystrophin protein or the 445-55 dystrophin protein. The differentiated cells phenotypically produced myotubes as demonstrated by myosin heavy chain staining. Representative image of differentiated Clone 56 is shown in FIG. 18.

Note Regarding Illustrative Aspects

While the present disclosure provides descriptions of various specific aspects for the purpose of illustrating various aspects of the present invention and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11369692B2). An electronic copy of the "Sequence Listing" will also be available from the USPTO upon request and payment of the fee set forth in 37 CFR 1.19(b)(3).

What is claimed is:

1. A single-molecule guide RNA (sgRNA) comprising in the 5' to 3' direction, a spacer sequence, a minimum CRISPR repeat sequence and a tracrRNA sequence, wherein the spacer sequence consists of an RNA sequence encoded by SEQ ID NO: 1410444, and wherein the sgRNA is capable of removing an AG sequence upstream of Exon 51 in the DMD gene when administered to a cell with a Cas9 protein or a nucleic acid encoding a Cas9 protein.

2. The sgRNA of claim 1, wherein the sgRNA comprises an RNA modification.

3. The sgRNA of claim 1, wherein the sgRNA is complexed with a Cas9 protein.

* * * * *

UNITED STATES PATENT AND TRADEMARK OFFICE
CERTIFICATE OF CORRECTION

| | |
|---|---|
| PATENT NO. | : 11,369,692 B2 |
| APPLICATION NO. | : 15/763328 |
| DATED | : June 28, 2022 |
| INVENTOR(S) | : Kabadi et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 692 days.

Signed and Sealed this
Eleventh Day of February, 2025

Coke Morgan Stewart
*Acting Director of the United States Patent and Trademark Office*